(12) United States Patent
Rice

(10) Patent No.: US 11,104,957 B2
(45) Date of Patent: *Aug. 31, 2021

(54) COMPOSITIONS AND METHODS FOR TREATING CANCERS

(71) Applicant: Aptose Biosciences, Inc., Toronto (CA)

(72) Inventor: William G. Rice, Del Mar, CA (US)

(73) Assignee: Aptose Biosciences, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/926,220

(22) Filed: Mar. 20, 2018

(65) Prior Publication Data

US 2019/0062842 A1  Feb. 28, 2019

Related U.S. Application Data

(63) Continuation of application No. 15/395,664, filed on Dec. 30, 2016, now abandoned, which is a
(Continued)

(51) Int. Cl.
*A61K 31/44* (2006.01)
*C12Q 1/6886* (2018.01)
(Continued)

(52) U.S. Cl.
CPC ........ *C12Q 1/6886* (2013.01); *A61K 31/4745* (2013.01); *A61K 31/706* (2013.01);
(Continued)

(58) Field of Classification Search
CPC .................................................. A61K 31/4745
(Continued)

(56) References Cited

U.S. PATENT DOCUMENTS 3,279,918 A   10/1966   Cassiers
3,297,710 A   1/1967   Silversmith
(Continued)

FOREIGN PATENT DOCUMENTS

CA   1195325   10/1985
CA   2351694   7/1993
(Continued)

OTHER PUBLICATIONS

Delgado et al. "MYC oncogene in myeloid neoplasias," Clin. Transl. Oncol. 2013, vol. 15, pp. 87-94, Published online Aug. 22, 2012 (Year: 2012).*

(Continued)

*Primary Examiner* — Shengjun Wang
(74) *Attorney, Agent, or Firm* — Cooley LLP

(57) ABSTRACT

The present invention relates to compositions and methods for treating of cancer. In some embodiments, the invention relates to the use of agents that can modulate a component in the CDX2-KLF4 signaling pathway to treat myelodysplastic syndromes (MDS), acute myelogenous leukemia (AML), acute lymphocytic leukemia (ALL), adult T-cell leukaemia (ATLL), lymphoma, gastric cancer, multiple myeloma, or combinations thereof, or a condition associated with abnormal activity of the CDX2-KLF4 signaling pathway.

10 Claims, 21 Drawing Sheets

Related U.S. Application Data continuation of application No. 14/506,463, filed on Oct. 3, 2014, now Pat. No. 9,567,643.

(60) Provisional application No. 62/037,868, filed on Aug. 15, 2014, provisional application No. 62/017,505, filed on Jun. 26, 2014, provisional application No. 61/919,023, filed on Dec. 20, 2013, provisional application No. 61/887,285, filed on Oct. 4, 2013.

(51) Int. Cl.
*C07D 471/14* (2006.01)
*A61K 31/4745* (2006.01)
*A61K 45/06* (2006.01)
*A61K 31/706* (2006.01)
*A61K 49/00* (2006.01)

(52) U.S. Cl.
CPC .......... *A61K 45/06* (2013.01); *A61K 49/0004* (2013.01); *C07D 471/14* (2013.01); *C12Q 2600/106* (2013.01); *C12Q 2600/158* (2013.01)

(58) Field of Classification Search
USPC ......................................................... 514/287
See application file for complete search history.

(56) References Cited

U.S. PATENT DOCUMENTS

| | | |
|---|---|---|
| 3,714,181 A | 1/1973 | Lantos |
| 4,089,747 A | 5/1978 | Bruschi |
| 4,423,046 A | 12/1983 | Carlson |
| 4,466,976 A | 8/1984 | Klose et al. |
| 4,585,771 A | 4/1986 | Klose et al. |
| 4,705,855 A | 11/1987 | Desideri et al. |
| 4,720,459 A | 1/1988 | Winkelhake |
| 4,721,670 A | 1/1988 | Osada et al. |
| 4,758,421 A | 7/1988 | Chang et al. |
| 4,762,706 A | 8/1988 | McCormick et al. |
| 4,902,705 A | 2/1990 | Hirota et al. |
| 4,970,226 A | 11/1990 | Sun |
| 5,011,472 A | 4/1991 | Aebischer |
| 5,023,252 A | 6/1991 | Hsieh |
| 5,024,935 A | 6/1991 | McClune |
| 5,047,318 A | 9/1991 | Snyder |
| 5,081,230 A | 1/1992 | Carney |
| 5,161,389 A | 11/1992 | Rockenfeller et al. |
| 5,300,631 A | 4/1994 | Weinberg et al. |
| 5,328,671 A | 7/1994 | Rockenfeller et al. |
| 5,441,716 A | 8/1995 | Rockenfeller et al. |
| 5,443,956 A | 8/1995 | Carney |
| 5,496,702 A | 3/1996 | Bishop |
| 5,501,959 A | 3/1996 | Lancaster et al. |
| 5,514,550 A | 5/1996 | Findlay |
| 5,656,644 A | 8/1997 | Adams |
| 5,686,455 A | 11/1997 | Adams |
| 5,693,589 A | 12/1997 | Goswami |
| 5,700,826 A | 12/1997 | Mjalli et al. |
| 5,753,687 A | 5/1998 | Mjalli |
| 5,809,775 A | 9/1998 | Tarabulski et al. |
| 5,916,891 A | 6/1999 | Adams |
| 5,945,418 A | 8/1999 | Bemis |
| 6,060,216 A | 5/2000 | Ichikawa |
| 6,117,609 A | 9/2000 | Maeda |
| 6,194,441 B1 | 2/2001 | Roberts |
| 6,266,955 B1 | 7/2001 | Liang et al. |
| 6,268,370 B1 | 7/2001 | Adams |
| 6,288,212 B1 | 9/2001 | Hancock |
| 6,521,655 B1 | 2/2003 | Beers |
| 6,589,966 B1 | 7/2003 | Torti et al. |
| 6,852,727 B2 | 2/2005 | Goulet et al. |
| 7,115,645 B2 | 10/2006 | Halfbrodt et al. |
| 7,291,404 B2 | 11/2007 | Aziz et al. |
| 7,364,868 B2 | 4/2008 | Ruppert et al. |
| 7,479,376 B2 | 1/2009 | Waldman et al. |
| 7,695,926 B2 | 4/2010 | Perez et al. |
| 7,718,685 B2 | 5/2010 | Shin et al. |
| 7,785,817 B2 | 8/2010 | Waldman et al. |
| 7,799,528 B2 | 9/2010 | Civin et al. |
| 7,884,120 B2 | 2/2011 | Al-Qawasmeh |
| 7,888,118 B2 | 2/2011 | Shin et al. |
| 7,989,089 B2 | 8/2011 | Wang et al. |
| 8,148,392 B2 | 4/2012 | Huesca et al. |
| 8,394,815 B2 | 3/2013 | Al-Qawasmeh |
| 8,969,372 B2 | 3/2015 | Huesca |
| 8,987,305 B2 | 3/2015 | Al-Qawasmeh |
| 9,567,643 B2 | 2/2017 | Rice |
| 10,080,739 B2 | 9/2018 | Huesca et al. |
| 2002/0119955 A1 | 8/2002 | Doyle et al. |
| 2004/0127527 A1 | 7/2004 | Mistuya et al. |
| 2004/0176601 A1 | 9/2004 | Goulet |
| 2004/0235073 A1 | 11/2004 | Ruppert et al. |
| 2004/0265628 A1 | 12/2004 | Wang et al. |
| 2005/0186442 A1 | 8/2005 | Gros |
| 2005/0195793 A1 | 9/2005 | Dalton et al. |
| 2005/0282285 A1 | 12/2005 | Radhamohan et al. |
| 2007/0105929 A1 | 5/2007 | Al-Qawasmeh |
| 2007/0123553 A1 | 5/2007 | Huesca |
| 2009/0232767 A1 | 9/2009 | Frankel |
| 2010/0168417 A1 | 7/2010 | Huesca et al. |
| 2010/0261174 A1 | 10/2010 | Grande et al. |
| 2010/0311683 A1 | 12/2010 | Beach et al. |
| 2011/0097343 A1 | 4/2011 | Atanackovic et al. |
| 2011/0152337 A1 | 6/2011 | Al-Qawasmeh |
| 2011/0171221 A1 | 7/2011 | Vieweg et al. |
| 2011/0281277 A1 | 11/2011 | Lee |
| 2011/0306602 A1 | 12/2011 | Wabnitz et al. |
| 2012/0100131 A1 | 4/2012 | Takayangi |
| 2012/0172244 A1 | 7/2012 | Buechler et al. |
| 2012/0251509 A1 | 10/2012 | Waldman et al. |
| 2013/0011411 A1 | 1/2013 | Pestell et al. |
| 2013/0034862 A1 | 2/2013 | Fantl et al. |
| 2013/0177632 A1 | 7/2013 | Al-Qawasmeh |
| 2013/0253842 A1 | 9/2013 | Sherwood et al. |
| 2014/0011279 A1 | 1/2014 | Yamanaka et al. |
| 2015/0099775 A1 | 4/2015 | Rice |
| 2015/0104392 A1 | 4/2015 | Rice |
| 2015/0374669 A1 | 12/2015 | Huesca |
| 2017/0335400 A1 | 11/2017 | Rice |
| 2019/0169215 A1 | 6/2019 | Rice et al. |

FOREIGN PATENT DOCUMENTS

| | | |
|---|---|---|
| CN | 1289774 | 9/1999 |
| CN | 1289775 | 9/1999 |
| DE | 3141063 | 10/1985 |
| DE | 3422175 | 12/1985 |
| DE | 10323591 | 12/2004 |
| EP | 0077024 A | 4/1983 |
| EP | 0165588 | 12/1985 |
| EP | 0812829 | 12/1997 |
| EP | 1428831 | 6/2004 |
| JP | 02258017 A | 10/1990 |
| JP | 11199582 A | 7/1999 |
| JP | 2001-506997 | 5/2000 |
| JP | 2000-273088 | 10/2000 |
| JP | 2002-275458 | 9/2002 |
| JP | 2002-364578 A | 12/2002 |
| JP | 2004-528206 A | 9/2004 |
| JP | 2006-503817 A | 2/2006 |
| WO | WO 1993/014081 A1 | 7/1993 |
| WO | WO 1994/011685 A1 | 5/1994 |
| WO | WO 1995/003297 A1 | 2/1995 |
| WO | WO 1996/018626 A1 | 6/1996 |
| WO | WO 1998/027108 A2 | 6/1997 |
| WO | WO 1997/036587 A1 | 10/1997 |
| WO | WO 1998/014081 A1 | 4/1998 |
| WO | WO 1998/027065 A1 | 6/1998 |
| WO | WO 1999/001128 A1 | 1/1999 |
| WO | WO 1999/001205 A1 | 1/1999 |
| WO | WO 1999/002155 A1 | 1/1999 |
| WO | WO 1999/007701 A1 | 2/1999 |
| WO | WO 2000/059541 A1 | 3/2000 |

(56) References Cited

FOREIGN PATENT DOCUMENTS

| | | |
|---|---|---|
| WO | WO 2000/033836 A1 | 6/2000 |
| WO | WO 2000/068206 A1 | 11/2000 |
| WO | WO 2000/068266 A1 | 11/2000 |
| WO | WO 2000/078761 A1 | 12/2000 |
| WO | WO 2001/026467 A1 | 4/2001 |
| WO | WO 2002/024680 A1 | 3/2002 |
| WO | WO 2002/046168 A1 | 6/2002 |
| WO | WO 2002/072576 A1 | 9/2002 |
| WO | WO 2002/083111 A2 | 10/2002 |
| WO | WO 2003/004023 A1 | 1/2003 |
| WO | WO 2003/032984 A1 | 4/2003 |
| WO | WO 2003/066579 A2 | 8/2003 |
| WO | WO 2003/087026 A1 | 10/2003 |
| WO | WO 2004/005264 A2 | 1/2004 |
| WO | WO 2004/016086 A2 | 2/2004 |
| WO | WO 2004/042207 A1 | 5/2004 |
| WO | WO 2005/047266 A1 | 5/2005 |
| WO | WO 2006/012903 A2 | 2/2006 |
| WO | WO 2006/081824 A2 | 8/2006 |
| WO | WO 2006/126177 A2 | 11/2006 |
| WO | WO 2007/000170 A1 | 1/2007 |
| WO | WO 2008/125883 A1 | 10/2008 |
| WO | WO 2010/102393 A1 | 9/2010 |
| WO | WO 2012/006032 A2 | 1/2012 |
| WO | WO 2013/149039 A1 | 10/2013 |
| WO | WO 2015/051302 A1 | 4/2015 |
| WO | WO 2015/051304 A1 | 4/2015 |
| WO | WO 2015/108986 A1 | 7/2015 |
| WO | WO 2019/089511 A1 | 5/2019 |

OTHER PUBLICATIONS

Abdel-Meguid et al., "An Orally Bioavailable HIV-1 Protease Inhibitor Containing an Imidazole-Derived Peptide Bond Replacement: Crystallographic and Pharmacokinetic Analysis." Biochemistry (1994); 33: 11671-11677.

Adams et al., "Pyrimidinylimidazole Inhibitors of p38: Cyclic N-1 Imidazole Substituents Enhance p38 Kinase Inhibition and Oral Activity." Bioorganic and Medicinal Chemistry Letters (2001); 11: 2867-2870.

Alakhov, V. et al., "Block copolymer-based formulation of doxombicin. From cell screen to clinical trials," Colloids and Surfaces B: Biointerfaces, vol. 16 (1999) pp. 113-134.

Allen, C. et al., "Controlling the physical behavior and biological performance of liposome formulations through use of surface grafted poly(ethylene glycol)," Biosciences Reports, vol. 22(2) (2002) pp. 225-250.

Allen, T.M. et al., "Stealth liposomes: an improved sustained release system for 1-beta-D-arabinofuranosylcytosine," Cancer Res., vol. 52 (1992) pp. 2431-2439.

Al-Sarraj, A et al., "Specificity of transcriptional regulation by the zinc finger transcription factors Spl, Sp3, and Egr-1," J Cell Biochem., vol. 94(1) (2005) pp. 153-167.

Andrews, G.K., "Cellular zinc sensors: MTF-1 regulation of gene expression," Biometals, vol. 14 (2001) pp. 223-237.

Antolini et al; Analogues of 4,5-bis(3,5-Dichlorophenyl)-2-Trifluoromethyl-1 H-Imidazole as Potential Antibacterial Agents; Bioorganic and Medicinal Chemistry Letters (1999); 9(7): 1023-1028.

Armesto et al., "A New Site Selective Synthesis of Benzoin Esters, Synthesis of Symmetrically and Unsymmetrically Substituted Benzils." Synthesis (1988); 1988(10): 799-801.

Arroyo et al., "Therapy of Murine Aspergillosis with Amphotericin B in Combination with Rifampin or 5-Fluorocytosine." Antimicrobial Agents and Chemotheraphy (1977); pp. 21-25.

Bhaduri et al., "Potential Antifertility Agents: Syntheses of 2,4,5-Substituted Imidazoles." Indian Journal of Chemistry (1996); 4(9): 419-420.

Bian, et al., "The Convenient Synthesis of Amphiphilic Phenanthroline Derivatives," Synthetic Communications, vol. 33(20) (2003) pp. 3477-3482.

Bian, Z. et al., "Syntheses, spectroscopic and crystal structural studies of novel imidazo[4,5-f]1,10-phenanthroline derivatives and their Eu(III) ternary complexes with dibenzoylmethane," Polyhedron, vol. 21 (2002) pp. 313-319.

Bing et al., "Synthesis of efficient blue and red light emitting phenanthroline derivatives containing both hole and electron transporting properties," Tetrahedron Letters, vol. 45(33) (2004) pp. 6361-6363.

Botana et al., "p-(1 H-Phenanthro[9,1 0-d]imidazo/-2-y/)-Substituted Calix[4]arene, a Deep Cavity for Guest Inclusion." Organic Letters (2004); 6(7): 1091-1094.

Boyd, M.R. et al., "Data Display and Analysis Strategies for the NCI Disease-Oriented In Vitro Antitumor Drug Screen," In Cytotoxic Anticancer Drugs: Models and Discovery and Development, Klimar Academic, Hingham, MA (1992) pp. 11-34.

Bu et al., "A novel approach to synthesis of tricyanovinylthiophene for heterocyclic imidazole nonlinear optical chromophores," Tetrahedron Letters (1996); 37 (41): 7331-7334.

Buss, et al., "Iron Chelators in Cancer Chemotherapy." Curr.Top Med. Chem. (2004); 4(15): 1623-1635.

Cairo, G.et al., "Induction of Ferritin Synthesis by Oxidative Stress," J. Biol. Chem., vol. 270(2) (1995) pp. 700-703.

Cammack et al, "EPR Spectroscopy of Iron," Methods Enzymol., vol. 227, Academic Press, Inc. (1993) pp. 353-384.

Cantley, L.C., "The phosphoinositide 3-kinase pathway," Science, vol. 296 (May 31, 2002) pp. 1655-1657.

CAS Registry No. 309285-51-6, entered Registry file on STN on Dec. 18, 2000.

CAS Registry No. 330449-52-0, entered Registry file on STN on Apr. 6, 2001.

CAS Registry No. 330449-64-4, entered into Registry file in STN on Apr. 6, 2001.

CAS Registry No. 332148-67-1, entered Registry file on STN on Apr. 21, 2001.

CAS Registry No. 404904-57-0, entered Registry file on STN on Apr. 10, 2002.

CAS Registry No. 416872-13-4, entered into Registry file in STN on May 16, 2002.

Chao et al., "Mono-, di- and tetra-nuclear ruthenium(II) complexes containing 2,2'-p-phenylenebis(imidazo[4,5-f]phenanthroline): synthesis, characterization and third-order non-linear optical properties." J. Chem. Soc., Dalton Trans. (2001); 1920-1926.

Chao et al., "Synthesis, electrochemical and spectroscopic properties of ruthenium(II) complexes containing 1,3-bis([1,10]phenanthroline-[5,6-d]imidazol-2-yl)benzene." Polyhedron (2000);19(16-17): 1975-1983.

Chaston, et al., "Examination of the Antiproliferative Activity of Iron Chelators." Clin. Cancer Research (2003); 9(1): 402-414.

Chen et al., "Krüppel-like factor 4 is transactivated by butyrate in colon cancer cells," J. Nutr., vol. 134( 4) (2004) pp. 792-798.

Chen, C., et al., "A possible tumor suppressor role of the KLF5 transcription factor in human breast cancer." Oncogene (2002); 21: 6567-6572.

Chen, J., et al. "Bleomycins: towards better therapeutics." Nat. Rev. Cancer (2005); 5(2): 102-112.

Chen, J.L. et al., "Gut-enriched Krüppel-like factor represses cyclin D1 promoter activity through Sp1 motif," Nucleic Acids Research, vol. 28(15) (2000) pp. 2969-2976.

Chen, X. et al., "Transcriptional Profiling of Krüppel-like Factor 4 Reveals a Function in Cell Cycle Regulation and Epithelial Differentiation," J. Mol. Biol., vol. 326(3) (2003) pp. 665-677.

Chen, X., et al., "Krüppel-like Factor 4 (Gut-enriched Krüppel-like Factor) Inhibits Cell Proliferation by Blocking $G_1/S$ Progression of the Cell Cycle." J. Biol. Chem. (2001); 276(32): 30423-30428.

Chen, Z.Y. et al., "Gut-enriched Krüppel-like Factor Represses Ornithine Decarboxylase Gene Expression and Functions as Checkpoint Regulator in Colonic Cancer Cells," J. Biol. Chem., vol. 277(48) (Nov. 29, 2002) pp. 46831-46839.

Chi, K., "Palladium Catalyst in DMSO for the Oxidation of Tolans to Benzils." Synthetic Communications (1994); 24(15): 2119-2122.

Cohen, S.R. et al, "The McGill Quality of Life Questionnaire: a measure of quality of life appropriate for people with advanced

(56) References Cited

OTHER PUBLICATIONS disease. A preliminary study of validity and acceptability," Palliative Medicine, vol. 9 (1995) pp. 207-219.

Coyle-Rink, J. et al., "Developmental Expression of Wnt Signaling Factors in Mouse Brain," Cancer Biology & Therapy, vol. 1(6) (2002) pp. 640-645.

Crosasso, P. et al., "Preparation, characterization and properties of sterically stabilized paclitaxel-containing liposomes," J. Controlled Release, vol. 63 (2000) pp. 19-30.

Cuenda et al., "Activation of stress-activated protein kinase-3 (SAPK3) by cytokines and cellular stresses is mediated via SAPKK3 (MKK6); comparison of the specificities of SAPK3 and SAPK2 (RK/p38)," The EMBO Journal (1997); 16(2): 295-305.

Cuenda et al., "SB 203580 is a specific inhibitor of a MAP kinase homologue which is stimulated by cellular stresses and interleukin-1." Federation of European Biochemical Societies Letters (1995); 364: 229-233.

Dang, D.T. et al, "Opposing effects of Krüppel-like factor 4 (gut-enriched Krüppel-like factor) and Krüppel-like factor 5 (intestinal-enriched Krüppel-like factor) on the promoter of the Krüppel-like factor 4 gene," Nucleic Acids Res., vol. 30(13) (2002) pp. 2736-2741.

Dang, D.T. et al., "Expression of the gut-enriched Krüppel-like factor (Krüppel-like factor 4) gene in the human colon cancer cell line RKO is dependent on CDX2," Oncogene, vol. 20(35) (2001) pp. 4884-4890.

Dang, D.T., et al., "Decreased expression of the gut-enriched Krüppel-like factor gene in intestinal adenomas of multiple intestinal neoplasia mice and in colonic adenomas of familial adenomatous polyposis patients." FEBS Letters (2000); 476(3): 203-207.

Dang, D.T., et al., "Overexpression of Krüppel-like factor 4 in the human colon cancer cell line RKO leads to reduced tumorigenecity." Oncogene (2003); 22: 3424-3430.

Database WPI; Section Ch. Week 199940, Derwent Publications Ltd., London, GB, Class B02, AN 1999-474062(XP002268773) & JP 11199582 (English abstract) A (Sagami Chem Res Cent), Jul. 27, 1999, 4 pages.

Demirayak et al., "Synthesis of Certain Derivatives of Ethyl a-[(phenanthro[9, I 0-d]imidazol-2-yl)phenoxy]alkanoate", Acta Pharmaceutica Turcica (1989); 31 (1): 19-25.

Diekema et al, "Survey of Infections due to Staphylococcus Species: Frequency of Occurrence and Antimicrobial Susceptibility of Isolates Collected in the United States, Canada, Latin America, Europe, and the Western Pacific Region for the SENTRY Antimicrobial Surveillance Program, 1997-1999." Clinical Infectious Diseases; (2001); 32:S114-132.

Dora, E.K. et al., "Synthesis of Some Fused 2-arylimidazoles and their Derivatives." Journal of Indian Chemical Society (1979); 56(6): 620-624.

Dos Santos, K.A. et al., "pH gradient loading of anthracyclines into cholesterol-free liposomes: enhancing drug loading rates through use of ethanol," Biochim. Biophys. Acta, vol. 1661 (2004) pp. 47-60.

Dos Santos, L.D. et al., "Improved retention of idarubicin after intravenous injection obtained for cholesterol-free liposomes," Biochim Biophys. Acta., vol. 1561 (2002) pp. 188-201.

Downey et al., "Degradation of DNA by 1,-10-phenanthroline." Biochem Biophys Res Commun (1980); 93(1): 264-270.

Drenan et al., "FKBP12-Rapamycin-associated Protein or Mammalian Target of Rapamycin (FRAP/mTOR) Localization in the Endoplasmic Reticulum and the Golgi Apparatus," J. Biol. Chem., vol. 279(1) (Jan. 2, 2004) pp. 772-778.

Drummond, C. et al., "Optimizing liposomes for delivery of chemotherapeutic agents to solid tumors, "Pharmacological Reviews, vol. 51( 4) (1999) pp. 691-743.

Eisenstein, R.S. et al, "Iron Regulatory Proteins, Iron Responsive Elements and Iron Homeostasis." J. Nutr., vol. 128(12) (1998) pp. 2295-2298.

Ekwall, Björn, "Screening of Toxic Compounds in Mammalian Cell Cultures." Annals New York Academy of Sciences (1983); 407(1): 64-77.

Embree, L. et al., "Pharmacokinetic behavior of vincristine sulfate following administration of vincristine sulfate liposome injection," Cancer Chemothr. Pharmacol., vol. 41 (1998) pp. 347-352.

Fields, R.D. et al, "Dual-attribute continuous monitoring of cell proliferation/cytotoxicity," Am. Biotechnol. Lab., vol. 11 (1993) pp. 48-50.

File, T.M., Jr. et al., "Antimicrobial therapy of community-acquired pneumonia," Infect. Dis. Clin. North Am., vol. 18 (2004) pp. 993-1016.

Fischer et al., "Dissociation Constants of the Conjugate Acids of Substituted Benzyl Phenyl Ketones and of Alkyl-substituted Benzophenones." Journal of American Chemical Society (1961); 83: 4208-4210.

Flatmark, T. et al., "Mitochondrial 'Non-Heme Non-FeS Iron' and It's Significance in the Cellular Metabolism of Iron," Proteins ofIron Metabolism, Brown, Aisen, Fielding and Crichton, eds., New York, Grun & Stratton (1976) pp. 349-358.

Foster, K.W., et al., "Increase of GKLF Messenger RNA and Protein Expression during Progression of Breast Cancer." Cancer Res. (2000); 60(22): 6488-6495.

Foster, K.W., et al., "Oncogene expression cloning by retroviral transduction of adenovirus E1A-immortalized rat kidney RK3E cells: transformation of a host with epithelial features by c-MYC and the zinc finger protein GKLF." Cell Growth Differ. (1999); 10(6): 423-434.

Fruman, D.A. et al, "Phosphoinositide kinases," Annu. Rev. Biochem., vol. 67 (1998), pp. 481-507.

Fruman, D.A. et al., "Phosphoinositide binding domains: embracing 3-phosphate," Cell, vol. 97(7)(1999)pp. 817-820.

Gabizon, A .. et al., "Effect of liposome composition and other factors on the targeting of liposomes to experimental tumors: biodistribution and imaging studies," Cancer Res., vol. 50 (1990) pp. 6371-6378.

Gaidenko, T.A. et al., "The PrpC serine threonine phosphatase and PrkC kinase have opposing physiological roles in stationary-phase Bacillus subtilis cells," J. of Bacteriol., vol. 184(22) (2002) pp. 6109-6114.

Gales et al., "Characterization of Pseudomonas aeruginosa Isolates: Occurrence Rates, Antimicrobial Susceptibility Patterns, and Molecular Typing in the Global SENTRY Antimicrobial Surveillance Program, 1997-1999." Clinical Infectious Diseases (2001); 32: S146-155.

Gao, D., et al., "Synthesis and electroluminescence properties of an organic europium complex," Journal of Alloys and Compounds 358(1-2):188-192.

Ghaleb, A.M., et al., "Krüppel-like factors 4 and 5: the yin and yang regulators of cellular proliferation." Cell Research (2005); 15(2): 92-96.

Ghannoum et al., "Susceptibility Testing of Fungi: Current Status of Correlation of In Vitro Data with Clinical Outcome." Journal of Clinical Microbiology (1996); 34: 489-495.

Goto et al., "Improved efficacy with non simultaneous administration of netilmicin and minocycline against methicillin—resistant *Staphylococcus aureus* in in vitro and in vivo models." International Journal of Antimicrobial Agents (1999); 11(1): 39-46.

Gower, J.D. et al, "Determination of Desferrioxamine-Available Iron in Biological Tissues by High-Pressure Liquid Chromatography," Analytical Biochemistry, vol. 180 (1989) pp. 126-130.

Grimmett, M.R., "Imidazoles and their Benzo Derivatives: (iii) Synthesis and Applications, 4.08.1 Ring Synthesis from Non-Heterocyclic Compounds," Comprehensive Heterocyclic Chemistry: The Structure, Reaction, Synthesis and Uses of Heterocyclic Compounds, Katrizky and Rees, eds., vol. 5, Pergamon Press, Oxford (1984) pp. 457-498.

Gross, C. et al, "Identification of the Copper Regulon in *Saccharomyces cerevisiae* by DNA Microarrays," J. Biol. Chem., vol. 275(41) (Oct. 13, 2000) pp. 32310-32316.

Guan, M., et al., "Bright Red Light-Emitting Electroluminescence Devices based on a functionalize Europium Complex." New Journal of Chemistry 27(12): 1731-1734 (2003).

(56) References Cited

OTHER PUBLICATIONS

Guijarro et al., "The Reaction of Active Zinc with Organic Bromides." Journal of American Chemical Society (1999); 21(7): 4155-4157.
Hanai, T. et al., "Prediction of retention factors of phenolic and nitrogen-containing compounds in reversed-phase liquid chromatography based on logP and pKa obtained by computational chemical calculation," Journal of Liquid Chromatography & Related Technologies, vol. 23(3) (2000) pp. 363-385.
Haroon, Z.A. et al., "Loss of metal transcription factor-I suppresses tumor growth through enhanced matrix deposition," FASEB J., vol. 18(11)(2004) pp. 1176-1184.
Heerding et al., "1,4 Disubstituted Imidazoles are Potential Antibacterial Agents Functioning as Inhibitors of Enoyl Acyl Carrier Protein Reductase (FabI)." Biorganic and Medicinal Chemistry Letters (2001); 11: 2061-2065.
Hiort, C. et al., "DNA binding of Δ- and λ-[Ru(phen)$_2$DPPZ]$^{2+}$." J. Am. Chem. Soc., vol. 115 (1993)pp. 3448-3454.
Hoban et al., "Worldwide Prevalence of Antimicrobial Resistance in *Streptococcus pneumoniae*, Haemophilus influenzas, and Moraxella catarrhalis in the SENTRY Antimicrobial Surveillance Program, 1997-1999." Clinical Infectious Diseases (2001); 32:S81-93.
Hollingshead, M. et al., "In Vivo Cultivation of Tumor Cells in Hollow Fibers," Life Sciences, vol. 57(2) (1995) pp. 131-141.
Horig et al., "From bench to clinic and back: Perspective on the 1st IQPC Translational Research conference." Journal of Translational Medicine (2004); 2(1): 44.
Huesca et al., "Adhesion and Virulence Properties of Epidemic Canadian Methicillin-Resistant *Staphylococcus aureus* Strain 1: Identification of Novel Adhesion Functions Associated with Plasmin-Sensitive Surface Protein." The Journal of Infectious Diseases (2002); 185: 1285-1296.
International Preliminary Examination Report for PCTCA0301229, dated Dec. 3, 2004.
International Preliminary Report on Patentability for International Application No. PCT/IB2006/051675, dated Nov. 29, 2007, 6 pages.
International Preliminary Report on Patentability for International Application No. PCT/US2014/059142, dated Apr. 5, 2016, 9 pages.
International Preliminary Report on Patentability for PCT Application No. PCT/US14/59140, dated Apr. 5, 2016, 8 pages.
International Preliminary Report on Patentability, dated May 15, 2006, International Application No. PCT/1B2004/052433, 8 pages.
International Search Report (ISR) of the International Searching Authority, dated Feb. 26, 2004; International Application No. PCT/CA2003/001229.
International search Report for International Application No. PCT/IB2006/051675, dated Jan. 3, 2007, 4 pages.
International Search Report of the International Searching Authority, dated Apr. 4, 2005; International Application No. PCT/182004/052433, 5 pages.
Isikdağ et al., "QSAR of Inhibitory Activities by 2,4,5-Trisubstituted Imidazole Derivatives on Tubifex Worms." Acta Pharmaceutica Turcica (1995); 37(1): 19-24.
Isikdağ et al., "Synthesis and analgesic activities of 2-substituted-1 H-phenantro [9, 10-d] imidazoles," Boll. Chim. Farmaceutico, 138:453-456 (1999).
Ito et al., "Photochemical Reaction of Imidazoles with Unsaturated Nitriles. Chemistry of Encounter Complex and Ion Pair," J. Org. Chem. 44:41-49 (1979).
Iwahi et al., "Virulence of *Escherichia coli* in Ascending Urinary-Tract Infection in Mice." Journal of Medical Microbiology (1982); 15: 303-316.
Janoff, A.S., "Liposomal delivery of drugs, genes and vaccines," Liposomes: Rational Design, Biotechnology Advances, vol. 17 (1999) pp. 511-513.
Kaczynski, J., et al., "Sp1- and Krüppel-like transcription factors." Genome Biology (2003); 4(2): 206.1-206.8.

Kihara, A. et al., "Beclin-phosphatidylinositol 3-kinase complex functions at the trans-Golgi network," EMBO Rep., vol. 2(4) (2001) pp. 330-335.
Kimura et al., "Preparation of 4-(4,5-Diphenyl-IH-imidazol-2-yl) benzaldehyde and Its Practical Synthetic Use in the Synthesis of Unsymmetrically Substituted Imidazoles." New Technologies & Medicine (2002); 3(1):30-34.
Kindermann, B.F., et al., "Identification of Genes Responsive to Intracellular Zinc Depletion in the Human Colon Adenocarcinoma Cell Line HT-29." The Journal of Nutrition (2004); 134 (1): 57-62.
Kindermann, B.F., et al., "Zinc-sensitive genes as potential new target genes of the metal transcription factor-1 (MTF-1)." Biochemistry and Cell Biology (2005); 83(2): 221-229.
King, F.G. et al., "Physiological pharmacokinetic parameters for cis-dichlorodiammineplatinum (II) (DDP) in the mouse," J. Pharmacokinet. Biophar., vol. 20 (1)(1992) pp. 95-99.
Kitano, Y. et al., "Suppression of proliferation of human epidermal keratinocytes by 1,25-dihydroxyvitamin D3," Euro J. Clin. Invest., vol. 21 (1991) pp. 53-58.
Klose et al., "The Suckling Mouse Model of Cholera." Trends in Microbiology (2000); 8: 189-191.
Kozlov, AV. et al., "Intracellular free iron in liver tissue and liver homogenate: Studies with electron paramagnetic resonance on the formation of paramagnetic complexes with desferal and nitric oxide," Free Radical Biology and Medicine, vol. 13 (1992) pp. 9-16.
Krieg, B. and Manecke, G., "Synthesis and Semiconductor Properties of Aryl-substituted Imidazoles." ("Synthese and Halbleitereigenschaften arylsubstitulerter Imidazole.") Z. Naturforsch (1967); 22b: 132-141, and English translation.
Langmade, S.J. et al., "The Transcription Factor MTF-1 Mediates Metal Regulation of the Mouse ZnT1 gene," J. Biol. Chem., vol. 275(44) (Nov. 3, 2000) pp. 34803-34809.
Lantos, "Reaction of Phenanthrenequinone with Ammonium Acetate," J. Org. Chem., 40(11):1641-1642 (1975).
Lee et al., "A Protein Kinase Involved in the Regulation of Inflammatory Cytokine Biosynthesis." Nature (1994); 327: 739-745.
Lewis, J.R., "Miscellaneous alkaloids: Amaryllidaceae, Sceletium, muscarine, imidazole, oxazole, peptide and other miscellaneous alkaloids." Natural Product Reports (1999); 16: 389-416.
Lewis, J.R., "Muscarine, imidazole, oxazole, thiazole and peptide alkaloids, and other miscellaneous alkaloids." Natural Product Reports (1998); 15: 371-395.
Lewis, J.R., "Muscarine, imidazole, oxazole, thiazole and peptide alkaloids, and other miscellaneous alkaloids." Natural Product Reports (1998); 15: 417-437.
Lichtlen, P. et al., "Putting its fingers on stressful situations: the heavy metal-regulatory transcription factor MTF-1," Bioessays, vol. 23(11) (2001) pp. 1010-1017.
Liggins, R.T. et al., "Solid-state characterization of paclitaxel," J. Pharm. Sci., vol. 86 (12) (Dec. 12. 1997) pp. 1458-1563.
Linden, P.K., "Treatment options for vancomycin-resistant enterococcal infections," Drugs, vol. 62 (2002) pp. 425-441.
Liu et al., "Synthesis, Characterization and Antitumor Activity of a Series of Polypyridyl Complexes," Metal Based Drugs, 7(6):343-348 (2000).
Liu, J. et al., "Influence of serum protein on polycarbonate-based copolymer micelles as a delivery system for a hydrophobic anticancer agent," J. Controlled Release, vol. 103 (2005) pp. 481-497.
Liu, J. et al., "Polymer-drug compatibility: a guide to the development of delivery systems for the anticancer agent, ellipticine," J. Pharm. Sci., vol. 93(1) (2004) pp. 132-143.
Lock et al., "Molecular mechanisms of growth inhibition induced by novel aryl-imidazole compounds in human cancer cells" Presented at IBC's 9th Annual World Congress Drug Discovery Technology Meeting (Boston Aug. 8-13, 2004) Abstract.
Lockshin, R.A. et al., "Apoptosis, autophagy and more," Int. J. Biochem. Cell Biol., vol. 36(12) (2004) pp. 2405-2419.
LoGrasso et al., "Kinetic Mechanism for p38 MAP Kinase." Biochemistry (1997); 36: 10422-10427.
Low et al., "Clinical Prevalence, Antimicrobial Susceptibility, and Geographic Resistance Patterns of Enterococci: Results from the SENTRY Antimicrobial Surveillance Program, 1997-1999." Clinical Infectious Diseases (2001); 32: S133-145.

(56) References Cited

OTHER PUBLICATIONS

Lowy, F.D., "*Staphylococcus aureus* infections," N. Engl. J. Med, vol. 339(8) (1998) pp. 520-532.

Lukyanov, A.N. et al., "Polyethylene glycol-diacyllipid micelles demonstrate increased accumulation in subcutaneous tumors, in mice," Phar. Res., vol. 19(10) (2002) pp. 1424-1429.

Mann et al., "1, 10-phenanthroline inhibits glycosylphosphatidylinositol anchoring by preventing phosphoethanolamine addition to glycosylphosphatidylinositol anchor precursors." Biochemistry (2001); 40(5): 1205-1213.

Martini, L.A. et al., "Iron Treatment Downregulates DMTI and IREG1 mRNA Expression in Caco-2 cells," J. Nutr., vol. 132( 4) (2002) pp. 693-696.

McCabe, M.J, Jr., et al., "Chelation of intracellular zinc triggers apoptosis in mature thymocytes." Lab. Invest. (1993); 69(1): 101-110.

McCorkle, R., et al., "Development of a system distress scale," Cancer Nursing, vol. 1 (1978) pp. 373-378.

McLay et al., "The Discovery of RPR 200765A, a p38 MAP Kinase Inhibitor Displaying a Good Oral Anti-Arthritic Efficacy." Bioorganic & Medicinal Chemistry (2001); 9: 537-554.

Medicines in Development for Infectious Diseases 2010, "Biopharmaceutical Research Continues Against Infectious Diseases with 395 Medicines and Vaccines in Testing," 36 pages.

Meijer, A.J. et al., "Regulation and role of autophagy in mammalian cells," Int. J. Biochem. Cell Biol., vol. 36(12) (2004) pp. 2445-2462.

Michie, Hamish R., "The value of animal models in the development of new drugs for the treatment of the sepsis syndrome," Journal for Antimicrobial Chemotherapy (1998); 41 (Sppl. A): 47-49.

Mizumura, Y. et al., "Cisplatin-incorporated polymeric micelles eliminate nephrotoxicity, while maintaining antitumor activity," Japanese Journal of Cancer Research, vol. 92 (2001) pp. 328-336.

Moghimi, S.M. et al., "Real-time evidence of surface modification at polystyrene lattices by poloxamine 908 in the presence of serum: in vivo conversion of macrophage-prone nanoparticles to stealth entities by poloxamine 908," FEBS. Lett., vol. 547 (2003) pp. 177-182.

Moghimi, S.M. et al., "Serum-mediated recognition of liposomes by phagocytic cells of the reticuloendothelial system—The concept of tissue specificity," Adv. Drug Deliv. Rev., vol. 32 (1998) pp. 45-60.

Monks, A. et al., "Feasibility of a High-flux Anticancer Drug Screen Using a Diverse Panel of Cultured Human Tumor Cell Lines," J. Natl. Cancer Inst., vol. 83(11) (Jun. 5, 1991) pp. 757-766.

Moribe, K. et al., "Encapsulation characteristics of nystatin in liposomes: effects of cholesterol and polyethylene glycol derivatives," International Journal of Pharmaceutics, vol. 188 (1999), pp. 193-202.

Moylan et al., "Synthesis and Nonlinear Optical Properties of Donor-Acceptor 875 Substituted Triaryl Azole Derivatives." Chemistry of Materials (1993); 5(10): 1499-1508.

Nakanishi, et al., "Development of the polymer micelle carrier system for doxorubicin," J. Controlled Release, vol. 74 (2001) pp. 295-302.

Narla, G. et al., "KLF6, a Candidate Tumor Suppressor Gene Mutated in Prostate Cancer." Science (2001); 294 (1551): 2563-2566.

Nielson, P. et al., "Non-Transferrin-Bound-Iron in Serum and Low-Molecular-Weight-Iron in the Liver of Dietary Iron-Loaded Rats," In. J. Biochem., vol. 25(2) (1993) pp. 223-232.

Nippon Kagaku Zasshi vol. 92 (1971), pp. 365-370, and English Abstract.

O'Brien, J. et al., "Investigation of the Alamar Blue (resazurin) fluorescent dye for the assessment of mammalian cell cytotoxicity," Eur. J. Biochem., vol. 267 (2000) pp. 5421-5426.

Ohnishi, S., et al., "Downregulation and growth inhibitory effect of epithelial-type Krüppel-like transcription factor KLF4, but not KLF5, in bladder cancer." Biochem. Biophys. Res. Commun. (2003); 308(2): 251-256.

Öllinger, K. et al., "Nutrient Deprivation of Cultured Rat Hepatocytes Increases the Desferrioxamine-available Iron Pool and Augments the Sensitivity to Hydrogen Peroxide," J. Biol. Chem., vol. 272(38) (1997) pp. 23707-23711.

Olynk et al., "Differential Production of TNK by Kupffer cells after phagocytosis of *E. coli* and *C. albicans*." American Journal of Physiology (1994); 10: 1-8.

Pan et al., "DNA-binding proteins as site-specific nucleases," Molecular Microbiology (1994);12(3): 335-342.

Pandya, A.Y., et al., "Nuclear Localization of KLF4 Is Associated with an Aggressive Phenotype in Early-Stage Breast Cancer." Clin. Cancer Res. (2004); 10(8): 2709-2719.

Patel, R., "Clinical impact of vancomycin-resistant enterococci," J. Antimicrob. Chemother., vol. 51(Suppl. S3)(2003) pp. 13-21.

Pechkin, A.A. el. al., Synthesis and Properties of 2-(2-Furyl)-and 2-(2-Thienyl)-1-methylphenanthro[9, 10-d]imidazoles, Russian Journal of Organic Chemistry (Translation of Zhurnal Organicheskoi Khimii), 2002, 38(5):726-730.

Petrat, F. et al., "The Chelatable Iron Pool in Living Cells: A Methodically Defined Quantity," Biol.Chem., vol. 383(3-4) (2002) pp. 489-502.

Pfaller and Yu, "Antifungal Susceptibility Testing." Infectious Disease Clinics of North America (2001); 15: 1227-1245.

Pfaller, et al., "Antifungal Susceptibility Testing: Technical Advances and Potential Clinical Applications." Clinical Infectious Diseases (1997); 24: 776-784.

Pozharskii et al., "Synthesis and Transformations of 2-(2-Furyl)- and 2[β-2-Furyl)Vinyl] Phenanthr [9, 10] Imidazoles," Chem. Het. Comp., 7: 950-952 (1971).

Press Release—Aug. 9, 2004—"Lorus Therapeutics Inc to Present Results of Novel Anticancer Small Molecule Studies," http://www.lorusthera.com/news-events/pressrelease-lorus-therapeutics-inc-present-results-323.php.

Press Release—Aug. 23, 2005—"Lorus Identifies Novel Class of Lead Drug Candidates from Small Molecule Anticancer Program.".

Press Release—May 12, 2004—"Lorus Announces Discovery of Novel Low Molecular Weight Compounds with Anticancer and Antibacterial Activity." BioFinance conference, Toronto, CA, http://www.lorusthera.com/news-events/press-release-lorus-announces-discovery-novel-low-302.php.

Rameh, L.E. et al., "The role of phosphoinositide 3-kinase lipid products in cell function," J. Biol. Chem., vol. 274(13) (1999) pp. 8347-8350.

Richardson, D.R., "Iron chelators as therapeutic agents for the treatment of cancer." Crit. Rev. Oncol. Hematol. (2002); 42(3): 267-281.

Roshal et al., "The Electronic Transitions and Spectra of Hetarylphenanthroimidazole Derivatives," J. Phys. Chem (2003); 77:1709-1714.

Rubinstein, L.V. et al., "Comparison of In Vitro Anticancer-Drug-Screening Data Generated with a Tetrazolium Assay Versus a Protein Assay Against a Diverse Panel of Human Tumor Cell Lines," J. Natl. Cancer Inst., vol. 82 (1990) pp. 1113-1118.

Sarshar et al., "2,4,5-Trisubstituted Imidazoles: Novel Nontoxic Modulators of P-glycoprotein Mediated Multidrug Resistance. Part 1." Biorganic and Medicinal Chemistry Letters (2000); 10: 2599-2601.

Sarshar et al., "Imidazole Libraries on Solid Support." Tetrahedron Letters (1996); 37: 835-838.

Schafer et al., "Failure is an option: learning from unsuccessful proof-of-concept trials." Drug Discovery Today (2008); 13 (21/22): 913-916.

Scialli, R. et al., "Protective effect of liposome encapsulation on paclitaxel developmental toxicity in the rat," Teratology, vol. 56 (1997) pp. 305-310.

Sharma, E. et al., "Activity of paclitaxel liposome formulations against human ovarian tumor xenografts," Int. J. Cancer, vol. 71 (1997) pp. 103-107.

Sherr, C.J. et al., "Inhibitors of mammalian $G_1$ cyclin-dependent kinases," Genes and Development, vol. 9(10)(1995) pp. 1149-1163.

(56) References Cited

OTHER PUBLICATIONS

Shibata et al., "Therapeutic efficacy of J-111, 225, a novel trans-3, 5-disubstituted pyrrolidinylthio-1 methylcarbapenem, against experimental murine systemic infections." Journal of Antimicrobial Chemotherapy (2000); 45: 379-382.
Shie, J.L. et al., "Gut-enriched Krüppel-like factor represses cyclin D1 promoter activity through Spl motif," Nucleic Acids Res., vol. 28(15) (2000) pp. 2969-2976.
Shie, J.L. et al., "Role of gut-enriched Krüppel-like factor in colonic cell growth and differentiation," Am. J. Physiol. Gastrointest. Liver Physiol., vol. 279( 4) (2000) pp. 0806-0814.
Shields, J.M. et al., "Identification and Characterization of a Gene Encoding a Gut enriched Krüppel-like Factor Expressed during Growth Arrest," The Journal of Biological Chemistry, vol. 271(33) (1996) pp. 20009-20017.
Shulman et al., "Action of 1,1 0-phenanthroline transition metal chelates on P388 mouse lymphocytic leukaemic cells," Chem.-Biol. Interacteractions (1977); 16(1): 89-99.
Siegel, T. et al., "Doxorubicin encapsulated in sterically stabilized liposomes for the treatment of a brain tumor model: biodistribution and therapeutic efficacy," J. Neurosurg., vol. 83 (1995) pp. 1029-1037.
Sigman et al.., "Oxygen-dependent cleavage of DNA by the 1,1 0-phenanthroline cuprous complex," J Biol Chem (1979); 254(24 ): 12269-12272.
Simor et al.; "Characterization and proposed nomenclature of epidemic strains of methicillin-resistant *Staphylococcus aureus* in Canada." Canada Communicable Disease Report (1999); 25-12: 105-108.
Sircar et al., "Dyes Derived from Phenanthraquinone. Part III. Phenanthrimidnazoles," J. Chem. Soc., 123:1559-1565 (1923).
Skehan, P. et al., "New Colorimetric Cytotoxicity Assay for Anticancer-Drug Screening," J. Natl. Cancer Inst., vol. 82 (1990) pp. 1107-1112.
Springman et al., "Zinc content and function in human fibroblast collagenase," Biochemistry (1995); 34(48): 15713-15720.
Steck et al., "Reactions of Phenanthraquinone and Retenequinone with Aldehydes and Ammonium Acetate in Acetic Acid Solution." J. Am. Chem. Soc. (1943); 65: 452-456.
Sternberg, S., "The Emerging Fungal Threat." Science (1994); 266: 1632-1634.
Subramaniam, M., et al., "Tissue, cell type, and breast cancer stage-specific expression of a TGF-β inducible early transcription factor gene." J. Cell Biochem. (1998); 68(2): 226-236.
Tanaseichuk et al., "Nitrogen-Containing Heterocyclic Free Radicals. VI. N-Methylindolyldiphenylimidazoles." Uch. Zap., Mord. Univ. (1971 ), No. 81, 95-97 (From: Ref. Zh., Khim. 1972, Abstr. No. 12zh318 D (and English Chemical Abstract No. 43368).
Tanaseichuk et al., Study of Nitrogen-Containing Heterocyclic Free Radicals."Part V. Synthesis of 2-(N-Methylindolyl-3)-4(5)-Phenyl-5(4) p-Phenyl-Substituted Imidazoles." Uch. Zap. Mord. Univ. (1971); 81: 95-97.
Tardi, P.G. et al., "Iposomal doxorubicin," J. Drug Targeting, vol. 4(3) (1996) pp. 129-140.
Thaler et al., "Evaluation of Single-Drug and Combination Antifungal Therapy in an Experimental Model of Candidiasis in Rabbits with Prolonged Neutropenia." The Journal of Infectious Diseases (1988); 158(1): 80-88.
Torchilin, V.P. et al., "Immunomicelles: Targeted pharmaceutical carriers for poorly soluble drugs," Proc. Natl. Acad. Sci., USA, vol. 100 (2003) pp. 6039-6044.
Totsuka et al., "Combined effects of vancomycin and imipenem against methicillin-resistant *Staphylococcus aureus* (MRSA) in vitro and in vivo." Journal of Antimicrobial Chemotherapy (1999); 44: 455-460.
Vanhaesebroeck, B. et al., "Signaling by distinct classes of phosphoinositide 3-kinases," Exp. Cell Res., vol. 253(1) (1999) pp. 239-254.
Vassilev, L.T. et al., "Cell-based screening approach for antitumor drug leads which exploits sensitivity differences between normal and cancer cells: identification of two novel cell-cycle inhibitors," Anti-Cancer Drug Design, vol. 16 (2001) pp. 7-17.
Walsh et al., "Effects of Preventive, Early, and Late Antifungal Chemotherapy with Fluconazole in Different Granulocytopenic Models of Experimental Disseminated Candidiasis." The Journal of Infectious Diseases (1990); 161: 755-760.
Wang, N., et al., "Down-regulation of gut-enriched Krüppel-like factor expression in esophageal cancer." World J. Gastroenterol. (2002); 8(6): 966-970.
Wei, D. et al., "Drastic Down-regulation of Krüppel-Like Factor 4 Expression Is Critical in Human Gastric Cancer Development and Progression." Cancer Research (2005); 65(7): 2746-2754.
Weissig, V. et al., "Accumulation of protein-loaded long-circulating micelles and liposomes in subcutaneous Lewis lung carcinoma in mice," Phar. Res., vol. 15(10) (1998)pp. 1552-1556.
Wermuth, C.G. et al., The Practice of Medicinal Chemistry, Academic Press (1998), 243-248.
Wermuth, C.G., Hiroshi NAGASE (translation supervisor), Saishin Sp-yaku Kagaku, Jo kan, Technomics Corporation, 1 1998, p. 243-248 (Japanese Version)—(Corresponding to C.G. Wermuth, The Practice of Medicinal Chemistry, Molecular Variations Based on Isosteric Replacements, 1996, 203-237, Academic Press (English version).
West, M.R. et al, "Simple Assays of Retinoid Activity as Potential Screens for Compounds That May Be Useful in Treatment of Psoriasis," J. Investigative Derm., vol. 99 (1992) pp. 95-100.
Written Opinion for International Application No. PCT/IB2006/051675, dated Jan. 3, 2007, 5 pages.
Written Opinion dated May 24, 2004 for International Application No. PCT/CA2003/01229, 6 pages.
Xiong, Ya, et al, "Interaction of polypyridyl ruthenium(II) complexes containing non-planar ligands with DNA." J. Chem. Soc., Dalton Trans. (1999); pp. 19-23.
Xiu R. Bu et al., "A Novel Approach to Synthesis of Tricyanovinylthiophene for heterocyclic Imidazole Nonlinear OpticalChromophores." Tetrahedron Letters (1996); 37(41): 7331-7334.
Xu et al., "Effects of the ancillary ligands of polypyridyl ruthenium (ii) complex(es) on the DNA-binding behaviors," New J. Chem., 2003, 27:1255-1263.
Xu, Hong, et al., "Synthesis and spectroscopic RNA binding studies of [Ru(phen)2MHPIP]2+." Inorg. Chem. Commun., vol. 6(2003) pp. 766-768.
Xu, Hong, et al., "Effects of ligand planarity on the interaction of polypyridyl Ru(II) complexes with DNA," J. Royal Society of Chemistry., Dalton Trans., vol. 11 (2003) pp. 2260-2268.
Yamada, M. et al., "Synthesis of 2,9-Dichloro-1, 10-phenanthroline from N,N'-Annelated Phenanthrolinediones," Bull. Soc. Chem. Jpn., vol. 63(9) (1990) pp. 2710-2712.
Yamamoto, Y. et al., "Long-circulating poly(ethylene glycol)-poly(D,L-lactide) block copolymer micelles with modulated surface charge," J. Controlled Release, vol. 77 (2001) pp. 27-38.
Yanke et al., "A CD-1 mouse model of infection with *Staphylococcus aureus*: Influence of gender on infection with MRSA and MSSA isolates." Canada Journal of Microbiology (2000); 46: 920-926.
Yasunaga, J., et al., "Identification of Aberrantly Methylated Genes in Association with Adult T-Cell Leukemia." Cancer Res. (2004); 64(17): 6002-6009.
Yegorov, D.Y. et al., "Simultaneous Determination of Fe(III) and Fe(II) in Water Solutions and Tissue Homogenates Using Desferal and 1,10-Phenanthrolin," Free Radic. Biol. Med., vol. 15 (1993) pp. 565-574.
Yokoyama, M. et al., "Characterization of physical entrapment and chemical conjugation of adriamycin in polymeric micelles and their design for in vivo delivery to a solid tumor," J. of Controlled Release, vol. 50 (1998) pp. 79-92.
Zalewski, P.D. et al., "Correlation of apoptosis with change in intracellular labile Zn(II) using Zinquin [(2-methyl-8-p-toluenesulphonamido-6-quinolyloxy)acetic acid], a new specific fluorescent probe for Zn(II)," Biochem. J., vol. 296(Pt. 2) (1993) pp. 403-408.
Zeytinoglu et al., "Mutagenicity Assay in Salmonella for Thirteen 2-Substituted-JH-phenanthro (9,10-d) Imidazoles", Drug and Chemical Toxicology (2003); 26(4): 245-257.

(56) References Cited

OTHER PUBLICATIONS

Zhang et al., "2,4,5-Trisumstituted Imidazoles: Novel Nontoxic Modulators of P-glycoprotein Mediated Multidrug Resistance. Part 2." Bioorganic & Medicinal Chemistry Letters (2000); 10: 2603-2605.

Zhang, C., "Bacterial signaling involving eukaryotic-type protein kinases," Mol. Microb., vol. 20(1) (1996) pp. 9-15.

Zhang, J.A. et al., "Development and characterization of a novel Cremophor® EL free liposome-based paclitaxel (LEP-ETU) formulation," Eur. J. Pharm. Biophar., vol. 59 (2005) pp. 177-187.

Zhang, Q.L., et al, "Design of New Polypyridyl Ligands and Their Effects on DNA binding Mechanisms of Complexes," Chemical Journal of Chinese Universities, vol. 24(10)(2003) pp. 1753-1755 (Article and Abstract).

Zhang, W. et al., "The gut-enriched Krüppel-like factor (Krüppel-like factor 4) mediates the trans activating effect of p53 on the p21 WAF1/Cip 1 promoter," J. Biol. Chem., vol. 275 (24) (2000) pp. 18391-18398.

Zhao, R., et al., "Role of zinc and iron chelation in apoptosis mediated by tachpyridine, an anti-cancer iron chelator." Biochemical Pharmacology (2004); 67(9): 1677-1688.

Zhao, W. et al., "Identification of Krüppel-like factor 4 as a potential tumor suppressor gene in colorectal cancer," Oncogene, vol. 23(2) (2004) pp. 395-402.

Zhuang, H. et al., Synthesis and character of two new NI-phenanthroline fluorescence probe for nucleic acid determination, College of Environment Science and Engineering, Huaxue Shiji, vol. 25(6) (2003) pp. 325-328 (with English Abstract).

Kimura, et al., "Antiproliferative and Antitumor Effects of Azacitidine Against the Human Myelodysplastic Syndrome Cell Line SKM-1." Anticancer Research (2012); 32: 795-798.

Abdel-Rahman et al., "Comprehensive characterization of HNPCC-related colorectal cancers reveals striking molecular features in families with no germline mismatch repair gene mutations," Oncogene, 24:1542-1551, 2005.

Bishop et al., "A randomized study of high-dose cytarabine in induction in acute myeloid leukemia" Blood 87 (5): 1710-7, 1996.

Chawengsaksophak et al., "Homeosis and intestinal tumours in Cdx2 mutant mice," Nature, 386(6620):84-7,1997—Abstract.

Costa et al., "CDX2 is mutated in a colorectal cancer with normal APC/b-catenin signaling," Oncogene, 18(35):5010-5014, 1999.

Crittenden, "An interpretation of familial aggregation based on multiple genetic and environmental factors". Ann. N. Y. Acad. Sci. 91 (3): 769-80.

Dexter, 1987, "Growth factors involved in haemopoiesis," J. Cell Sci. 88:1.

Estey E.,"Treatment of acute myelogenous leukemia". Oncology (Williston Park) 16 (3): 343-52, 355-6; discussion 357, 362, 365-6, 2002—retrieved online at http://www.cancernetwork.com Dec. 9, 2014.

Faber et al., "CDX2-driven leukemogenesis involves KLF4 repression and deregulated PPARγ signaling", J Clin Invest. Jan. 2, 2013;123(1):299-314.

Fenaux et al., "A randomized comparison of all transretinoic acid (ATRA) followed by chemotherapy and ATRA plus chemotherapy and the role of maintenance therapy in newly diagnosed acute promyelocytic leukemia. The European APL Group". Blood 94 (4): 1192-200, 1999.

Florean et al., "Epigenomics of leukemia: from mechanisms to therapeutic applications". Epigenomics. Oct. 2011;3(5):581-609.

Foley et al., Continuous culture of human lymphoblasts from peripheral blood of a child with acute leukemia. Cancer 1965 18:522-529.

Ghaleb et al. (Krüppel-like factor 4 exhibits antiapoptotic activity following gamma-radiation-induced DNA damage. Oncogene. 2007. 26:2365-73).

Golde and Gasson, 1988, Scientific American, July: 62-70.

Greenstein et al., Characterization of the MM.1 human multiple myeloma (MM) cell lines: a model system to elucidate the characteristics, behavior, and signaling of steroid-sensitive and -resistant MM cells. Exp Hematol. Apr. 2003;31(4):271-82.

Horwitz et al., "Anticipation in familial leukemia". Am. J. Hum. Genet. 59 (5): 990-8. PMC 1914843. PMID 8900225, 1996.

Huang Meng-er et al.,"Use of all-trans retinoic acid in the treatment of acute promyelocytic leukemia". Blood 72 (2): 567-72, 1988.

Huesca et al., "A novel small molecule with potent anticancer activity inhibits cell growth by modulating intracellular labile zinc homeostasis," Mol Cancer Ther. 8:2586-96 (2009).

Iacobucci et al., "Cytogenetic and molecular predictors of outcome in acute lymphocytic leukemia: recent developments", Curr Hematol Malig Rep. Jun. 2012;7(2):133-43.

Kimura et al., Antiproliferative and Antitumor Effects of Azacitidine Against the Human Myelodysplastic Syndrome Cell Line SKM-1, Anticancer Research 32:795-798, 2002.

Lengerke et al., "BMP and Wnt specify hematopoietic fate by activation of the Cdx-Hox pathway", Cell Stem Cell. Jan. 10, 2008;2(1):72-82.

Lengerke et al., "Caudal genes in blood development and leukemia", Ann N Y Acad Sci. Aug. 2012;1266:47-54.

List et al., "The myelodysplastic syndromes: biology and implications for management", J. Clinical Onc., Aug. 1990, 8 (8): 1424-1441-Abstract.

Lombardi et al., "Molecular characterization of human multiple myeloma cell lines by integrative genomics: insights into the biology of the disease. Genes Chromosomes", Cancer. Mar. 2007, 46(3):226-38-Abstract.

Malik et al., "miR-2909-mediated regulation of KLF4: a novel molecular mechanism for differentiating between B-cell and T-cell pediatric acute lymphoblastic leukemias", Mol Cancer. 13:175, 2014.

Nilsson et al., Established immunoglobulin producing myeloma (IgE) and lymphoblastoid (IgG) cell lines from an IgE myeloma patient. Clin Exp Immunol. Oct. 1970;7(4):477-89.

Ogawa, 1989, "Hemopoietic stem cells: stochastic differentiation and humoral control of proliferation," Environ. Health Presp. 80:199.

Qayyum et al., "Adult T-cell leukemia/lymphoma". Arch Pathol Lab Med. Feb. 2014;138(2):282-6.

Rouhi et al., "Deregulation of the CDX2-KLF4 axis in acute myeloid leukemia and colon cancer", Oncotarget. Feb. 2013;4(2):174-175.

Rowland et al., "KLF4, p21 and context-dependent opposing forces in cancer", Nat Rev Cancer. Jan. 2006;6(1):11-23-Abstract.

Rowland et al., The KLF4 tumour suppressor is a transcriptional repressor of p53 that acts as a context-dependent oncogene. Nat Cell Biol. 2005. 7:1074-82—Abstract.

Saandi et al., "Regulation of the tumor suppressor homeogene Cdx2 by HNF4α in intestinal cancer," Oncogene. Aug. 8, 2013;32(32):3782-8-Abstract.

Schoenhals et al., "Krüppel-like factor 4 blocks tumor cell proliferation and promotes drug resistance in multiple myeloma," Haematologica. 2013. 98:1442-9.

Scholl et al., "The homeobox gene CDX2 is aberrantly expressed in most cases of acute myeloid leukemia and promotes leukemogenesis," J. Clin. Invest. 117(4):1037-1048, 2007.

Tallman et al., "All-trans-retinoic acid in acute promyelocytic leukemia". N. Engl. J. Med. 337 (15): 1021-8, 1997.

Wang et al., "siRNA targeting of Cdx2 inhibits growth of human gastric cancer MGC-803 cells", World J Gastroenterol. Apr. 28, 2012; 18(16): 1903-1914.

Wicking et al., "CDX2, a human homologue of Drosophila caudal, is mutated in both alleles in a replication error positive colorectal cancer," Oncogene 1998;17(5):657-659) 1998.

Wood et al., "The Genomic Landscapes of Human Breast and Colorectal Cancers," Science,318(5853):1108-1113, 2007.

Yagi et al., "Genomic structure and alterations of homeobox gene CDX2 in colorectal carcinomas," Br. J. Cancer., 79(3-4): 440-444, 1999.

Yoon et al.,"Krüppel-like Factor 4 Mediates p53-dependent G1/S Cell Cycle Arrest in Response to DNA Damage", J Biol Chem. vol. 278, No. 4, Jan. 24, pp. 2101-2105, 2003.

Albitar et al., "Myelodysplastic syndrome is not merely "preleukemia" ", *Blood*, Aug. 2002, 100(3): 791-798.

(56) References Cited

OTHER PUBLICATIONS

International Search Report issued by the International Searching Authority for PCT Application No. PCT/US14/59140, dated Dec. 31, 2014, 3 pages.
Written Opinion issued by the International Searching Authority for PCT Application No. PCT/US14/59140, dated Dec. 31, 2014, 7 pages.
International Search Report issued by the International Searching Authority for PCT Application No. PCT/US2014/059142, dated Dec. 31, 2014, 3 pages.
Written Opinion issued by the International Searching Authority for PCT Application No. PCT/US2014/059142, dated Dec. 31, 2014, 7 pages.
Greenberg et al. "Myelodysplastic Syndromes," Journal of the National Comprehensive Cancer Network, 2011, 9(1):30-56.
Search Report with English translation in Chinese Patent Application No. 201480064470.2, dated Jul. 24, 2017, 8 pages.
Extended European Search Report in European Patent Application No. 14850583.7, dated May 2, 2017, 10 pages.
Cercek et al., "Phase I study of LOR-253, a novel inducer of Kruppel-like factor 4, in patients with advanced solid tumors," Eur. J. Cancer 49(Suppl. 2):S179-S180, Abstract 864 (2013), 2 pages.
Cukier et al., "Abstract 4649: Utilizatrion of KLF-4 as a pharmacodynamic biomarker for in vivo anticancer activity of a novel small molecule drug LOR-253," Cancer Res. 73(8 Supplement):Abstract 4649, 4 pages (2013).
Goldman, "torus Therapeutics, Inc. The Next Major Oncology Player," Goldman Small Cap Research, 13 pages (2012), http://www.baystreet.ca/articles/research_reports/goldman_research/LOR-1 0.9.12-[3].pdf [retrieved on Apr. 12, 2017].
Lum et al., "Abstract 4544: Induction of KLF4 by LOR-253 as an innovative therapeutic approach to induce apoptosis in acute myeloid leukemia," Cancer Res. 74(19 supplement):Abstract 4544, 4 pages (2014).
Karahoca and Momparler, "Pharmacokinetic and pharmacodynamic analysis of 5-aza-2'-deoxycytidine (decitabine) in the design of its dose-schedule for cancer therapy." Clin Epigenetics (Feb. 2013); 5(1): 3, pp. 1-16.
Musolino, et al., "Epigenetic therapy in myelodysplastic syndromes." European Journal of Haematology (2010); 84(6): 463-473.
Schmelz, et al., "Induction of gene expression by 5-Aza-2'-deoxycytidine in acute myeloid leukemia (AML) and myelodysplastic syndrome (MDS) but not epithelial cells by DNA-methylation-dependent and -independent mechanisms." Leukemia (2005); 19(1): 103-111.
Cercek et al., "Phase 1 study of APTO-253 HCl, an Inducer of KLF4, in patients with advanced or metastatic solid tumors," Invest. New Drugs. (2015) 33: 1086-1092.
ClinicalTrials.gov Identifier: NCT01432145, A Clinical Trial in Patients With Breast Cancer Susceptibility Gene (BRCA) Defective Tumours (6MP), First Posted—Sep. 12, 2011, Last Update Posted—Jul. 9, 2019, retrieved from https://clinicaltrials.gov/ct2/show/results/NCT01432145, 11 pages.
Davies et al., "HRDetect is a Predictor of BRCA1 and BRCA2 Deficiency Based on Mutational Signatures," Nat. Med. (2017) 23(4): 517-525.
De Luca et al., "BRCA1 Loss Induces GADD153-Mediated Doxorubicin Resistance in Prostate Cancer," Mol Cancer Res., 2011, 9(8): 1078-1090.

Degrolard-Courcet et al., "Development of primary early-onset colorectal cancers due to biallelic mutations of the FANCD1/BRCA2 gene," European Journal of Human Genetics, 2014, vol. 22, pp. 979-987.
Enoiu et al., "Repair of cisplatin-induced DNA interstrand crosslinks by a replication-independent pathway involving transcription-coupled repair and translesion synthesis," Nucleic Acids Research, 2012, 40(18): 8953-8964.
Hughes-Davies et al., "EMSY Links the BRCA2 Pathway to Sporadic Breast and Ovarian Cancer," Cell, Nov. 2003, 115(5): 523-535.
International Search Report, dated Feb. 7, 2019 for International Application No. PCT/US2018/058103, 4 pages.
Ivashkevich et al., "Use of the γ-H2AX Assay to Monitor DNA Damage and Repair in Translational cancer research," Cancer Letters, (2012) 327: 123-133.
Jasin, M., "Homologous repair of DNA damage and tumorigenesis: the BRCA connection," Oncogene, (2002) 21: 8981-8993.
Khanna et al., "DNA double-strand breaks: signaling, repair and the cancer connection." Nature Genetics, Mar. 2001, 27(3): 247-254.
Konecny et al., "PARP inhibitors for BRCA 1/2-mutated and sporadic ovarian cancer: current practice and future directions," Br J Canc., 2016, vol. 115, pp. 1157-1173.
Kriege et al., "Sensitivity to First-Line Chemotherapy for Metastatic Breast Cancer in BRCA1 and BRCA2 Mutation Carriers," J Clin. Oncology, Aug. 2009, vol. 27, No. 23, pp. 3764-3771.
Kurtz et al., "Broad Activity of APTO-253 in AML and Other Hematologic Malignancies Correlates with KFL4 Expression Level," Blood, Abstract 1358, Poster, (2015), 57$^{th}$ ASH Annual Meeting, 1 page.
Ledermann et al. "Olaparib Maintenance Therapy in Platinum-Sensitive Relapsed Ovarian Cancer," N. Engl. J Med. Apr. 2012, 366(15): 1382-1392.
Mirza et al. "Niraparib Maintenance Therapy in Platinum-Sensitive, Recurrent Ovarian Cancer," N. Engl. J Med. Dec. 2016, 375(22): 2154-2164.
Mudasir et al., "DNA Binding of Iron(II)-Phenanthroline Complexes: Effect of Methyl Substitution on Thermodynamic Parameters." Z. Naturforsch, 2008, vol. 63b, pp. 37-46.
Niell et al., "BRCA1 and BRCA2 Founder Mutations and the Risk of Colorectal Cancer," Journal of the National Cancer Institute, Jan. 2004, vol. 96, No. 1, pp. 15-21.
Radice, P., "Mutations of BRCA Genes in Hereditary Breast and Ovarian cancer." J. Exp. Clin. Cancer Res., 2002, 21(3 Suppl): 9-12.
Roberts et al., "Results of a phase II clinical trial of 6-mercaptopurine (6MP) and methotrexate in patients with BRCA-defective tumours," British Journal of Cancer (2020) 122:483-490.
Sopik et al., "BRCA1 and BRCA2 Mutations and the Risk for Colorectal Cancer," Clinical Genetics, 2015, vol. 87, No. 5, pp. 411-418.
Tsai et al "APTO-253 Is a New Addition to the Repertoire of Drugs that Can Exploit DNA BRCA1/2 Deficiency," Molecule Cancer Therapeutics, (2018) vol. 17, No. 6, pp. 1167-1176.
Tutt et al., "The relationship between the roles of BRCA genes in DNA repair and cancer predisposition," Trends Mol Med., Dec. 2002, 8(12): 571-576.
Written Opinion of the International Searching Authority dated Feb. 7, 2019 for International Application No. PCT/US2018/058103, 7 pages.
Zhang et al., "Inhibition of c-Myc by Apto-253 As an Innovative Therapeutic Approach to Induce Cell Cycle Arrest and Apoptosis in Acute Myeloid Leukemia," Blood (2016) 128(22):1716, 4 pages.

* cited by examiner

COMPOSITIONS AND METHODS FOR TREATING CANCERS

CROSS-REFERENCE TO RELATED APPLICATIONS

This application is a continuation application of U.S. patent application Ser. No. 15/395,664, filed on Dec. 30, 2016, which is a continuation application of U.S. patent application Ser. No. 14/506,463, filed on Oct. 3, 2014, issued as U.S. Pat. No. 9,567,643, which claims the benefit of U.S. Provisional Application No. 61/887,285, filed Oct. 4, 2013, U.S. Provisional Application No. 61/919,023, filed Dec. 20, 2013, U.S. Provisional Application No. 62/017,505 filed on Jun. 26, 2014, and U.S. Provisional Application No. 62/037,868, filed Aug. 15, 2014, all of which are hereby incorporated by reference in their entireties.

FIELD OF THE INVENTION

The present invention relates generally to compositions and methods for treating cancers.

BACKGROUND OF THE INVENTION

Many drugs or drug candidates have been developed for the treatment of various cancers, including some small molecule compounds. However, current treatments for many cancers are not very effective in patients with specific subsets of cancers, or are too toxic in such patients or in general.

Myelodysplastic syndromes (MDS) are a group of diseases that affect the bone marrow and blood. Some types of MDS are mild and easily managed, while other types are severe and life-threatening. Myelodysplastic syndromes (MDS) are rarely cured; most patients never actually complete treatment. The current treatment of MDS is based on the stage and the mechanism of the disease that predominates the particular phase of the disease process. Bone marrow transplantation has been used in patients with poor prognosis or late-stage MDS. Epstein and Slease, 1985, Surg. Ann. 17:125. This type of therapy, however, is both painful for donor and recipient, because of the involvement of invasive procedures and can cause severe and even fatal complications to the recipient, particularly with allogeneic transplant and related Graft Versus Host Disease (GVHD) results. Therefore, the risk of GVHD restricts the use of bone marrow transplantation to patients with otherwise fatal diseases. Further, as most patients are elderly and only a few young MDS patients will have a matched donor, the use of bone marrow transplantation is limited. There remains a need for more effective methods for treating MDS and its related disorders.

Mild MDS can grow more severe over time. It can also develop into a fast-growing, severe leukemia, acute myelogenous leukemia (AML). AML is a subset of leukemia. It is the most common form of adult leukemia (blood cancer) with a <20% survival rate after 5 years and less than 5% if patients are age >65. Current treatments for AML are blunt and harsh chemotherapies (i.e., cytarabine, anthracycline, etc.) that are not targeted and have limiting off-target toxicities. Thus, there is a severe unmet medical need for distinguishing patients who are potentially sensitive to a certain treatment, and patients who are not.

The present invention meets this need and provides compositions and methods for the effective treatment of cancers.

SUMMARY OF THE INVENTION

The present invention provides compositions and methods for treating cancers. In some embodiments, the present invention is based, in part, on the discovery that the Caudal-related Homeobox protein CDX2—Krüppel-like factor 4 (KLF4) signaling pathway ("the CDX-KLF4 signaling pathway") is important for the pathogenesis of a group of cancers, and that active agents with an ability of modulating the CDX2-KLF4 signaling pathway can be used to treat such cancers effectively.

In one aspect, the invention provides compositions for treating cancers. In some embodiments, the compositions comprise at least one anti-cancer active agent that can modulate the CDX2-KLF4 signaling pathway in a human subject. Without wishing to be bound by any particular theory, the anti-cancer agents of the present invention can act through one or more mechanisms. Such mechanisms include, but are not limited to: (1) inhibition of CDX2 activity; (2) induction of KLF4 activity; (3) induction of p21 CDK inhibitor; (4) induction of G1/S Cell cycle arrest; (5) induction of Caspase 3 enzyme; and (6) induction of apoptosis. As used herein, the term "activity" of a component in the CDX2-KLF4 signaling pathway can be a parameter at genomic DNA level, transcriptional level, post-transcriptional level, translational level, post-translational level, including, but not limited to gene activity, RNA activity, and protein activity. The gene activity can be gene copy number, gene amplification number, or promoter activity, etc. RNA activity can be mRNA abundance, synthesis rate, and/or stability, etc. Protein activity can be protein abundance, synthesis rate, stability, enzymatic activity, phosphorylation rate, modifications, binding activity, etc.

In some embodiments, the active agent is a small molecule pharmaceutical compound. In some embodiments, the pharmaceutical compound is a 2,4,5-trisubstituted imidazole compound described in US 2007/0123553A1, or 2-indolyl imidazo[4,5-d]phenanthroline compounds described in U.S. Pat. No. 8,148,392, or functional derivatives thereof. In some embodiments, the pharmaceutical compound has the structure of formula I:

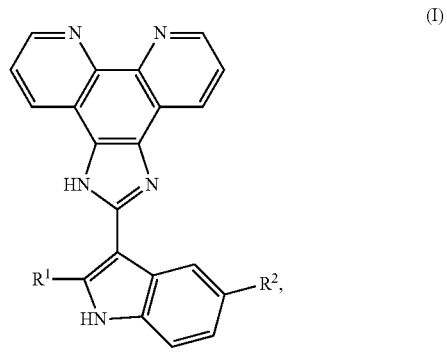

Wherein R1 is C1-C4 alkyl; and R2 is halogen.

In some embodiments, $R^1$ is methyl, isopropyl, or t-butyl.

In some embodiments, the pharmaceutical compound is selected from the group consisting of:

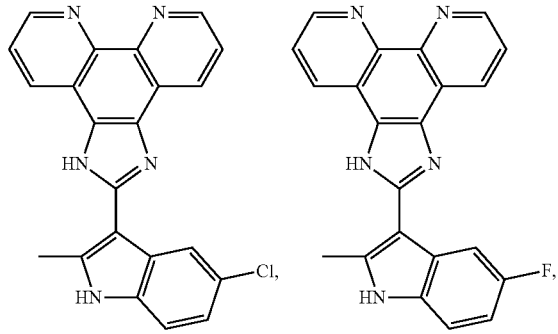

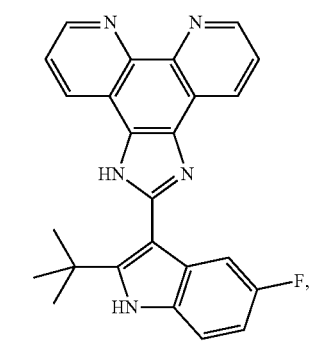

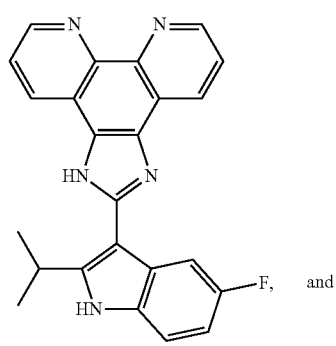

and

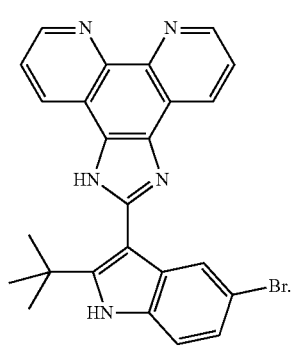

In some embodiments, the pharmaceutical compound has the structure of formula II:

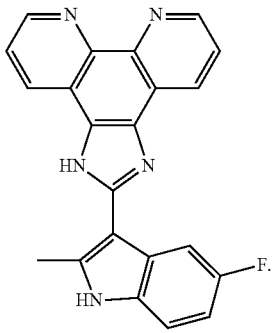

(a.k.a. LOR-253 or APTO-253)

In some embodiments, the cancer is associated with abnormal activity of the CDX2-KLF4 signaling pathway in the human subject. In some embodiments, one or more components in the CDX2-KLF4 signaling pathway have abnormal activity when compared to the activity of a control group. In some embodiments, the cancer is leukemia/lymphoma. In some embodiments, the cancer is myelodysplastic syndromes (MDS). In some embodiments, the MDS is high-risk MDS. In some embodiments, the cancer is acute myelogenous leukemia (AML). In some embodiments, the AML is refractory AML. In some embodiments, the AML is elderly AML. In some other embodiments, the cancer is acute lymphocytic leukemia (ALL). In some embodiments, the ALL is a pediatric ALL. In some embodiments, the pediatric ALL is pediatric T-cell ALL or pediatric B-cell ALL. In some other embodiments, the cancer is chronic myelogenous leukemia (CML). In some embodiments, the cancer is adult T-cell leukaemia (ATLL). In some embodiments, the cancer is caused by human T-lymphotrophic virus type 1. In some embodiments, the cancer is lymphoma, gastric cancer, or multiple myeloma. In some embodiments, the lymphoma is Hodgkin lymphoma, non-Hodgkin's lymphoma (NHL), Burkitts lymphoma, or B-cell lymphoma. In some embodiments, the cancer is a combination of any of the cancers described herein.

In some embodiments, the human subject has one or more symptoms of MDS. In some embodiments, the human subject to be treated has an ineffective production of blood cells, such as myeloid blood cells. In some embodiments, the human subject has an anemia. In some embodiments, the human subject has low blood counts caused by bone marrow failure.

In some embodiments, the cancer is acute myelogenous leukemia (AML). In some embodiments, the AML is refractory AML. In some embodiments, the AML is elderly AML. As used herein, elderly AML patients are those patients who have, or may have AML, with an age above 60. In some embodiments, elderly AML patients are in their first relapse. In some embodiments, the AML is not elderly AML. As used herein, non-elderly AML patients are those who have, or may have AML, with an age equal to or below 60. In some embodiments, the non-elderly AML patients are in their second relapse.

In some embodiments, the cancer is acute lymphocytic leukemia (ALL). In some embodiments, the ALL is a pediatric or child ALL. As used herein, pediatric or child ALL patients are those patients who have, or may have ALL, with an age under 21. In some embodiments, the ALL is not pediatric or child ALL. As used herein, non-pediatric ALL patients are those who have, or may have ALL, with an age equal to or above 21.

In some embodiments, an anti-cancer compound of the present invention is administered to a human subject in need as part of a combination therapy. In some embodiments, the combination therapy comprises radiotherapy. In some embodiments, the combination therapy comprises chemotherapy.

In some embodiments, an effective amount of an anti-cancer agent or a pharmacologically acceptable salt or solvate thereof of the present invention is administered to the human subject. In some embodiments, an effective amount of the anti-cancer agent is effective to treat the cancer or symptoms of the cancer, effective to inhibit cancer cell proliferation, or effective to prevent or reduce severity of a future occurrence of cancer when administered to a subject who is susceptible and/or who may develop a cancer or symptoms of the cancer. In some embodiments, the administration of the anti-cancer agent provides statistically significant therapeutic effect or clinical efficacy for treating the cancer. In some embodiments, an anti-cancer compound of the present invention is administered with a dosage of about 0.01 to about 200 mg. In some embodiments, an anti-cancer compound of the present invention is administered with a dosage of about 0.05 to about 100 mg. In some embodiments, an anti-cancer compound of the present invention is administered with a dosage of about 1.0 to about 50 mg. In some embodiments, the daily dosages of the compounds of the present invention typically fall within the range of about 0.01 to about 100 mg/kg of body weight, or within the range of about 20 mg/m2 to about 400 mg/m2 in single or divided dose. In some embodiments, an anti-cancer compound of the present invention is administered once, twice, three times or more per day.

In some embodiments, the treatment last 1, 2, 3, 4, 5, 6, 7, 8, 9, 10, or more cycles. In some embodiments, each cycle lasts at least 1, 2, 3, 4, 5, 6, 7, 8, 9, 10 or more days. In some embodiments, the gap between two cycles is at least 1, 2, 3, 4, 5, 6, 7, 8, 9, 10, or more days.

In some embodiments, the anti-cancer agent is unit dosage form.

In some embodiments, the cancer to be treated is AML, the compound is LOR-253 (a. k. a. APTO-253), and the compound is administered with a dosage of about 125 mg/m2. In certain embodiments, the compound is administered two times per week for four weeks.

The invention provides methods for treating a condition associated with abnormal activity of the CDX2-KLF4 signaling pathway. In some embodiments, the condition is associated with abnormal activity of one or more component of the CDX2-KLF4 signaling pathway, such as CDX2, KLF4, p21, and/or p53 in a human subject. In some embodiments, the condition is associated with abnormal (e.g., lower than normal) level of KLF4 activity. In some embodiments, the condition is associated with abnormal (e.g., higher than normal) level of CDX2 activity. In some embodiments, the abnormal level of CDX2 is due to a genetic alteration of CDX2.

In some embodiments, the methods of the present invention further comprise determining the activity of a component in the CDX2-KLF4 signaling pathway, such as the KLF4 activity and/or CDX2 activity in the human subject before, during, and/or after the treatment. In some embodiments, the methods of the present invention further comprise determining the presence or absence of a genetic alteration of CDX2.

Additional aspects and embodiments of the invention will be apparent from the detailed description that follows.

BRIEF DESCRIPTION OF THE DRAWINGS

FIG. 5 also shows that treatment of LOR-253 results in G1/S cell cycle arrest in THP1 and HL-60 cell lines (right panel).

DETAILED DESCRIPTION

Definitions

Figure 1:
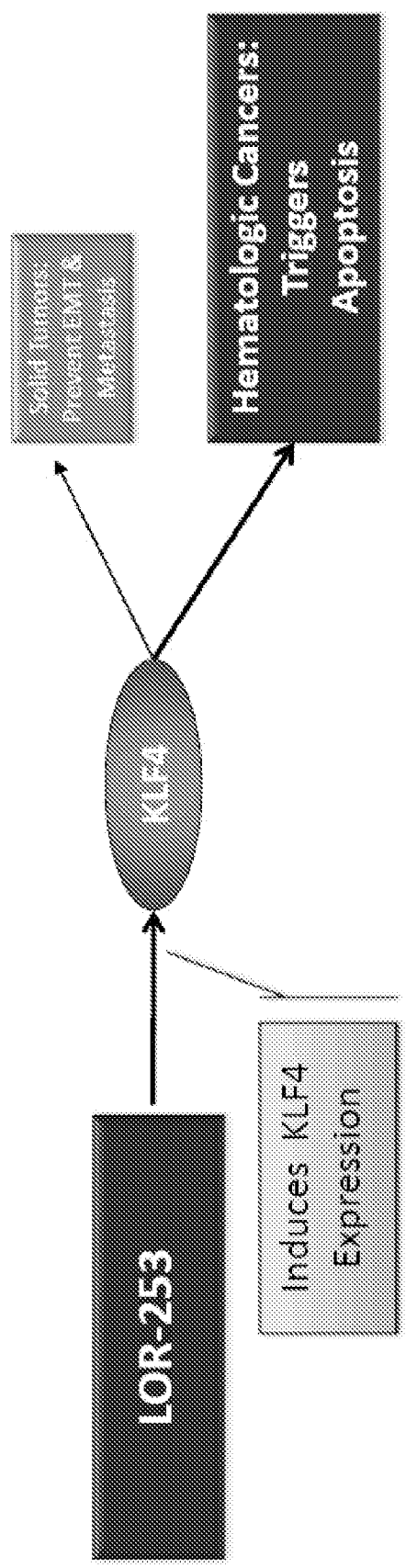
FIG. 1 is a diagram of non-limiting mechanism of how an active agent of the present invention (e.g., formula I, a.k.a. LOR-253 or APTO-253) treats cancer. Without wishing to be bound by any particular theory, in certain cancer types, such as solid tumors, KLF4 is down regulated, which is essential for accelerated cell proliferation, epithelial-mesenchymal transition (EMT) and metastasis; in certain hematologic cancers: KLF4 is down regulated, which is essential for leukemogenesis. LOR-253 induces KLF4 expression which in turn inhibits cancer cell proliferation, EMT, and metastasis, and/or triggers apoptosis.
Figure 2:
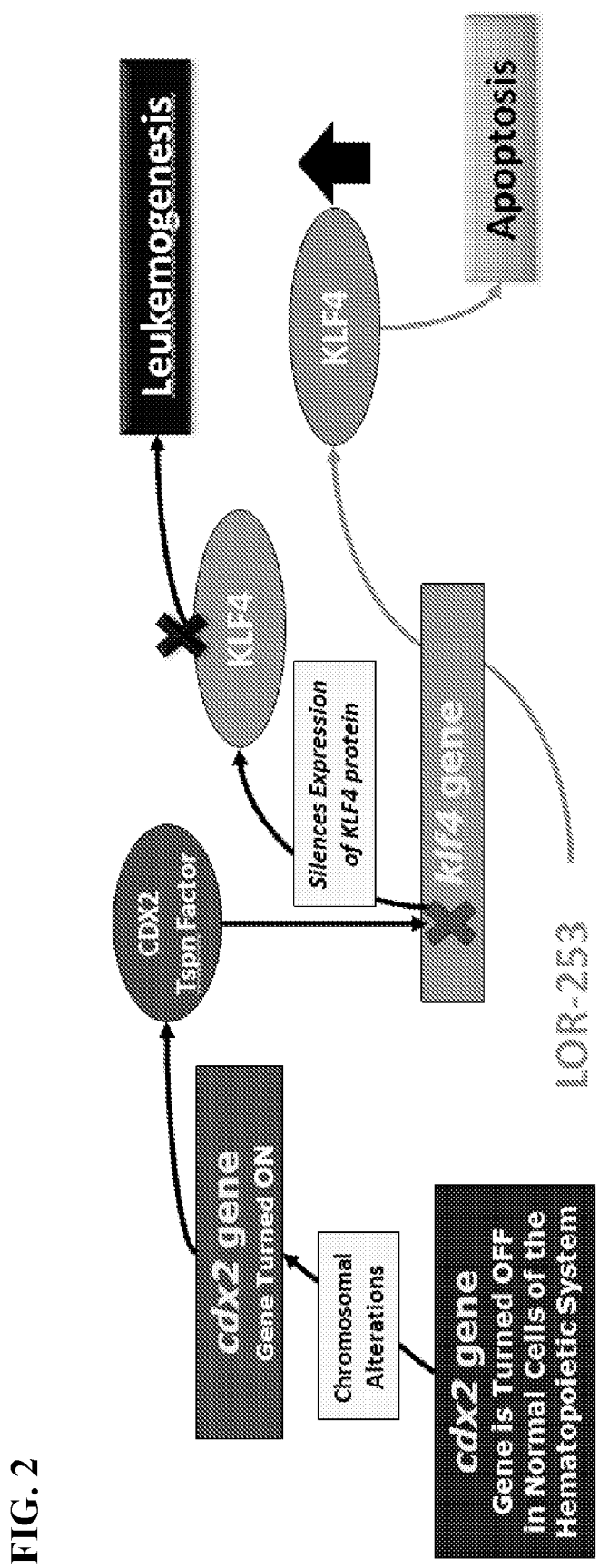
FIG. 2 is a diagram that shows non-limiting mechanism of how CDX2 functions in certain cancers and how LOR-253 treats such cancers. Without wishing to be bound by any particular theory, in normal cells of the hematopoietic system, the CDX2 gene is turned off or expressed at a relatively low level. In certain cancers including AML, CDX2 is turned on or increased, leading to aberrantly expressed CDX2 transcription factor. CDX2 binds to the promoter region of the KLF4 gene and inhibits KLF4 expression, which is an essential step to promote leukemogenesis. LOR-253 induces KLF4 expression which in turn triggers apoptosis of the cancerous leukocytes.

The verb "comprise" as is used in this description and in the claims and its conjugations are used in its non-limiting sense to mean that items following the word are included, but items not specifically mentioned are not excluded.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

The invention provides isolated, chimeric, recombinant or synthetic polynucleotide sequences. As used herein, the terms "polynucleotide", "polynucleotide sequence", "nucleic acid sequence", "nucleic acid fragment", and "isolated nucleic acid fragment" are used interchangeably herein and encompass DNA, RNA, cDNA, whether single stranded or double stranded, as well as chemical modifications thereof. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. In some embodiments, the isolated, chimeric, recombinant or synthetic polynucleotide sequences are derived from gene markers of the present invention.

The invention also provides proteins or polypeptides. In some embodiments the proteins or polypeptides are isolated, purified, chimeric, recombinant or synthetic. As used herein, the term "polypeptide" or "protein" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component. Also included are, for example, polypeptides containing one or more analogs of an amino acid (including, for example, unnatural amino acids, etc), as well as other modifications known in the art. Polypeptides can occur as single chains or associated chains. Polypeptides of the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc). In some embodiments, the sequences of the proteins or polypeptides are derived from gene markers of the present invention.

Single letter amino acid abbreviations used herein have their standard meaning in the art, and all peptide sequences described herein are written according to convention, with the N-terminal end to the left and the C-terminal end to the right.

Figure 13:
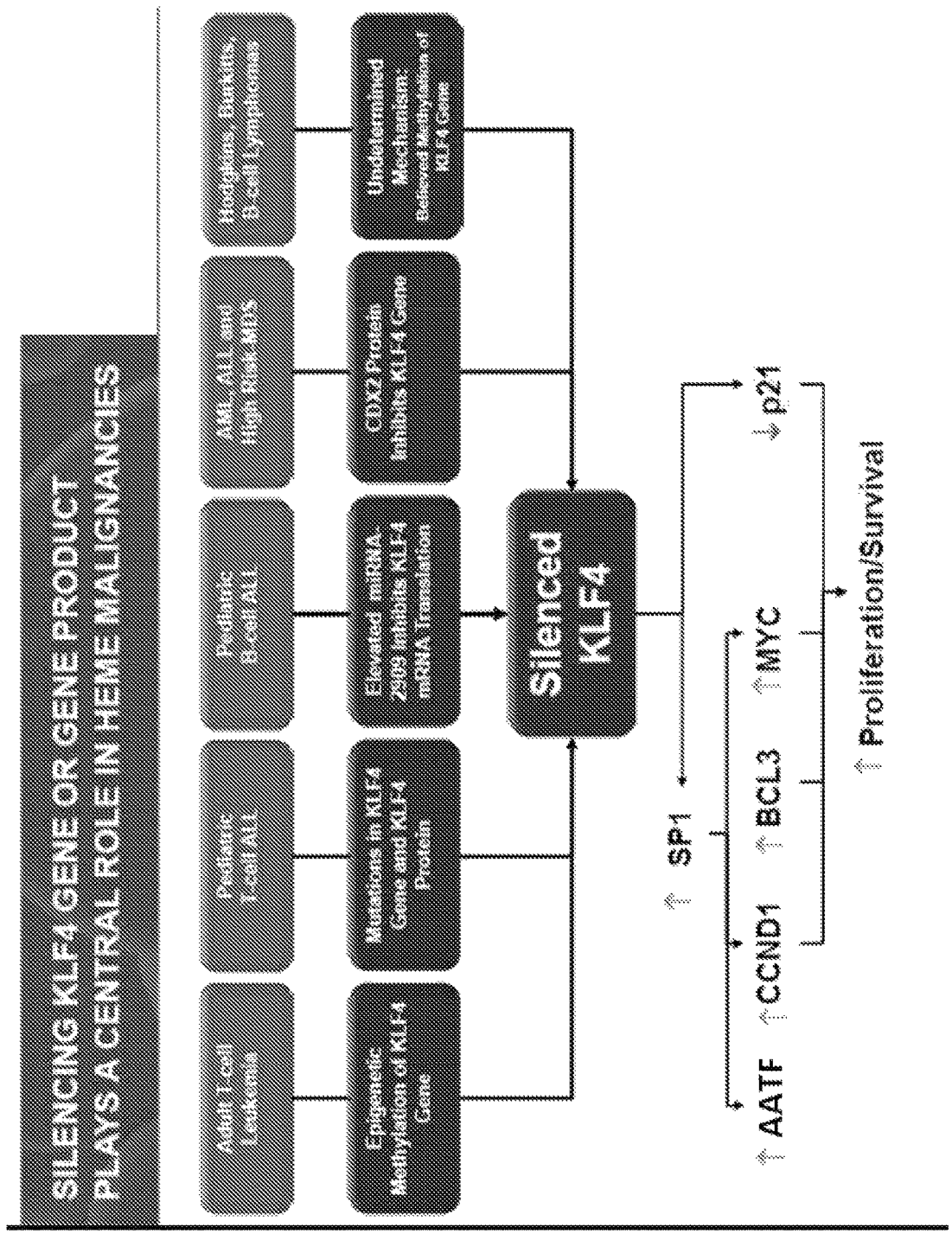
FIG. 13 is a diagram that shows non-limiting mechanism of how silencing KLF4 gene or gene product plays a central role in various heme malignancies. For example, epigenetic methylation of the KLF4 gene relates to adult T-cell lymphoma patients, mutations in KLF4 genes or proteins relate to pediatric T-cell ALL patients, elevated microRNA-2909 relates to pediatric B-cell ALL patients, aberrant expression of CDX2 relates to AML, ALL, and MDS patients, which all lead to silencing of KLF4 activity (including but not limited to expressional and functional activities). Silencing of KLF4 has also been observed in various lymphoma. The lower part of the diagram illustrates that silenced KLF4 causes increased cancer cell proliferation through various "cell fate genes".
Figure 14:
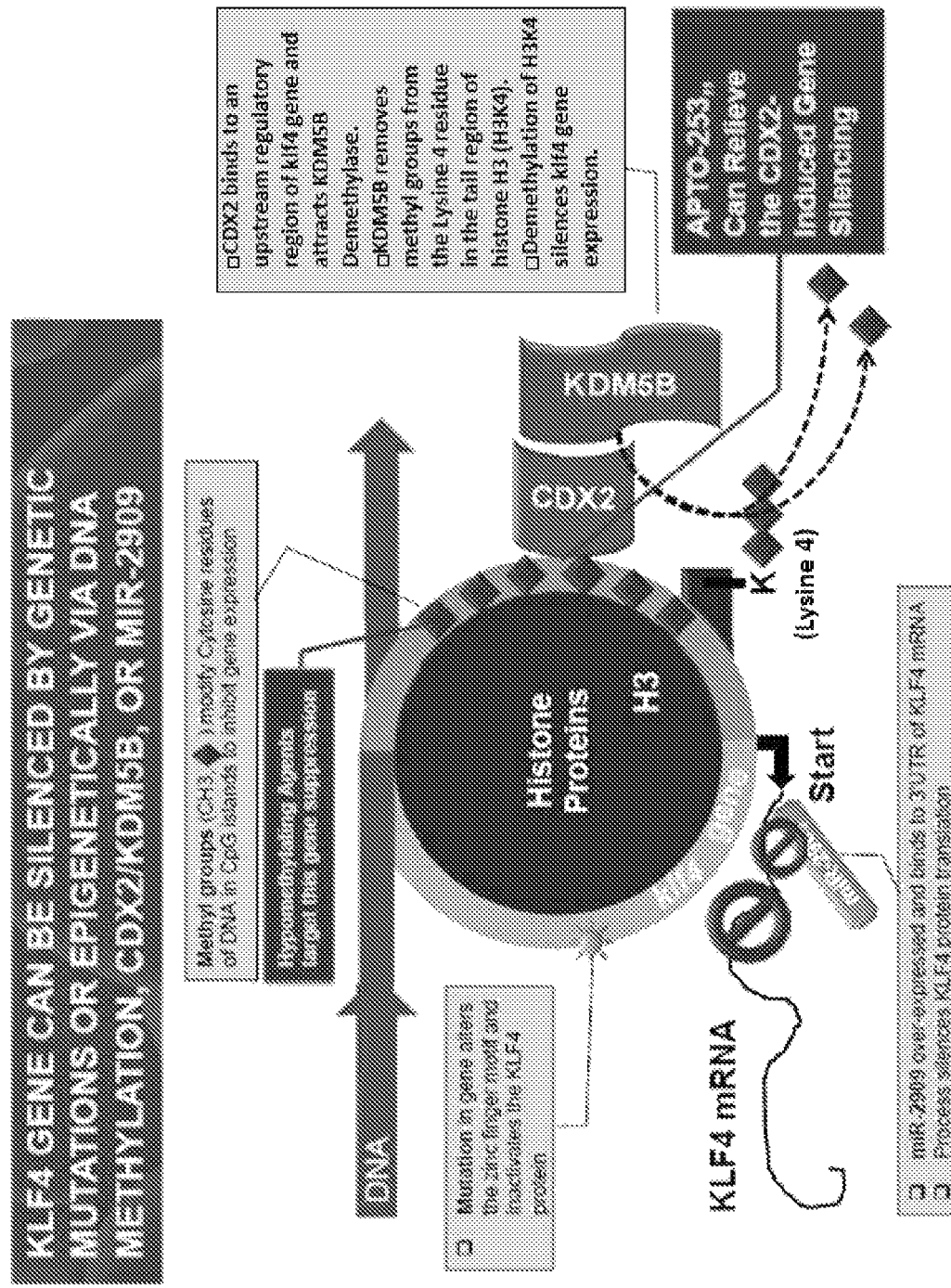
FIG. 14 is a diagram that shows non-limiting mechanism of how KLF4 gene activity can be silenced by genetic mutations or epigenetic events and how LOR-253/APTO-253 can induce KLF4 expression. Such epigenetic events include, but are not limited to, DNA hypomethylation or demethylation, aberrant/elevated expression of CDX2 which can lead to increased presence of a demethylase KDM5B in an upstream regulatory region of the klf4 gene, and elevated amount of miR-2909. LOR-253/APTO-253 can induce KLF4 expression by relieving gene silencing caused at least by CDX2/KDM5B and/or other mechanisms

As used herein, the term "component in the CDX2-KLF4 signaling pathway", refers to CDX2, KLF4, or other genes, gene products (including but not limited to RNA and protein), or other biological molecules that can modulate the activity of CDX2 and/or KLF4, directly or indirectly, or genes, gene products, or other biological molecules that can be modulated by CDX2 and/or KLF4, directly or indirectly. The modulation can either increase or decrease the activity level of a given gene. Such components include, but are not limited to CDX2, KLF4, KDM5B, miR-2909, p53, p21, Caspase-3, Annexin V, BAX, BCL2, BCL3, BMP, Wnt, HNF4α, Fgf, Hox, SP1, MYC, CCND1, AATF, and those described in Scholl et al. ("The homeobox gene CDX2 is aberrantly expressed in most cases of acute myeloid leukemia and promotes leukemogenesis", *J. Clin. Invest.* 117: 1037-1048 (2007).), Yoon et al. (Krüppel-like Factor 4 Mediates p53-dependent G1/S Cell Cycle Arrest in Response to DNA Damage, Vol. 278, No. 4, Issue of January 24, pp. 2101-2105, 2003), Faber et al. (CDX2-driven leukemogenesis involves KLF4 repression and deregulated PPARγ signaling, J Clin Invest. doi:10.1172/JCI64745.), Rouhi et al. ("Deregulation of the CDX2-KLF4 axis in acute myeloid leukemia and colon cancer", Oncotarget. 2013 February; 4(2):174-175.), Lengerke et al. ("BMP and Wnt specify hematopoietic fate by activation of the Cdx-Hox pathway", Cell Stem Cell. 2008 Jan. 10; 2(1):72-82.), Saandi et al. ("Regulation of the tumor suppressor homeogene Cdx2 by HNF4α in intestinal cancer", Oncogene. 2013 Aug. 8; 32(32):3782-8.), Malik et al., (miR-2909-mediated regulation of KLF4: a novel molecular mechanism for differentiating between B-cell and T-cell pediatric acute lymphoblastic leukemias. Mol Cancer. 13:175, 2014), and Rowland et al. ("KLF4, p21 and context-dependent opposing forces in cancer", Nat Rev Cancer. 2006 January; 6(1):11-23), each of which is incorporated herein by reference in its entirety for all purposes. KLF4 negatively regulates (or suppresses) the activity of SP1, MYC, BCL3, CCND1, and AATF, directly or indirectly, while positively regulates the activity of p21. In addition, KLF4 negatively regulates the activity of p53 in some cancer types (e.g. breast cancer, as described by Rowland et al., The KLF4 tumour suppressor is a transcriptional repressor of p53 that acts as a context-dependent oncogene. Nat Cell Biol. 2005. 7:1074-82), but positively regulates the activity of p53 in some other cancer types (e.g., colon cancer and multiple myeloma, as described by Ghaleb et al. (Krüppel-like factor 4 exhibits antiapoptotic activity following gamma-radiation-induced DNA damage. Oncogene. 2007. 26:2365-73), and Schoenhals et al. (Krüppel-like factor 4 blocks tumor cell proliferation and promotes drug resistance in multiple myeloma. Haematologica. 2013. 98:1442-9)). Many of the genes regulated by KLF4 are referred to as "cell fate genes". An illustration of some possible effects of silenced KLF4 gene expression or activity on some of the genes modulated by KLF4 can be found in FIG. 13. Some other components in the CDX2-KLF4 signaling pathway can modulate the expression of KLF4. Examples of such components include, but are not limited to, CDX2, KDM5B (a demethylase), and a miRNA "miR-2909". An illustration of some possible mechanisms of how these KLF4 modulators can affect KLF4 gene expression or activity in various cancer types can be found in FIG. 13 and FIG. 14. A component in the CDX2-KLF4 signaling pathway can be used as a biomarker according to the methods described herein for treating cancers, especially for treating cancers by an anti-cancer agent of the present invention, such as LOR-253/APTO-253.

As used herein, the term "modulate the CDX2-KLF4 signaling pathway" refers to the process in which one or more component in the CDX2-KLF4 signaling pathway is modulated by an agent or an event (including a mutation). In some embodiments, such modulation leads to increased, decreased, normalized, and/or stabilized activity of one or more components in the CDX2-KLF4 signaling pathway.

The term lower alkyl refers to $(C_1-C_6)$alkyl. A lower alkyl includes methyl, ethyl, propyl, isopropyl, butyl, iso-butyl, sec-butyl, pentyl, 3-pentyl, hexyl, $(C_3-C_6)$cycloalkyl (e.g., cyclopropyl, cyclobutyl, cyclopentyl, or cyclohexyl), $(C_3-C_6)$cycloalkyl$(C_1-C_6)$alkyl (e.g., cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl), $(C_1-C_6)$alkoxy (e.g., methoxy, ethoxy, propoxy, isopropoxy, butoxy, iso-butoxy, sec-butoxy, pentoxy, 3-pentoxy, or hexyloxy) $(C_2-C_6)$alkenyl (e.g., vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl), $(C_2-C_6)$alkynyl (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl), $(C_1-C_6)$alkanoyl (e.g., acetyl, propanoyl or butanoyl), halo$(C_1-C_6)$alkyl (e.g., iodomethyl, bromomethyl, chloromethyl, fluoromethyl, trifluoromethyl, 2-chloroethyl, 2-fluoroethyl, 2,2,2-trifluoroethyl, or pentafluoroethyl), hydroxy$(C_1-C_6)$alkyl (e.g., hydroxymethyl, 1-hydroxyethyl, 2-hydroxyethyl, 1-hydroxypropyl, 2-hydroxypropyl, 3-hydroxypropyl, 1-hydroxy butyl, 4-hydroxybutyl, 1-hydroxypentyl, 5-hydroxypentyl, 1-hydroxyhexyl, or 6-hydroxyhexyl), $(C_1-C_6)$alkoxycarbonyl (e.g., methoxycarbonyl, ethoxycarbonyl, propoxycarbonyl, isopropoxycarbonyl, butoxycarbonyl, pentoxycarbonyl, or hexyloxycarbonyl), $(C_1-C_6)$alkylthio (e.g., methylthio, ethylthio, propylthio, isopropylthio, butylthio, isobutylthio, pentylthio, or hexylthio), and/or $(C_2-C_6)$alkanoyloxy (e.g., acetoxy, propanoyloxy, butanoyloxy, isobutanoyloxy, pentanoyloxy, or hexanoyloxy).

A compound described herein or its function derivative can be used according to the present invention. The term "derivative" as used herein includes derivatives, analogs, prodrugs, and unnatural precursors of a given compound.

As used herein, the term "treatment efficacy" and variants thereof are generally indicated by alleviation of one or more signs or symptoms associated with the disease and can be readily determined by one skilled in the art. "Treatment efficacy" may also refer to the prevention or amelioration of signs and symptoms of toxicities typically associated with standard or non-standard treatments of a disease. Determination of treatment efficacy is usually indication and disease specific and can include any methods known or available in the art for determining that a treatment is providing a beneficial effect to a subject. For example, evidence of treatment efficacy can include but is not limited to general improvements in the overall health of the subject, such as but not limited to enhancement of patient life quality, increase in predicted subject survival rate, decrease in depression, decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, etc. In some embodiments of the invention, the treatment efficacy is clinical efficacy or statistically significant.

The terms "treating" and "treatment" as used herein refer to an approach for obtaining beneficial or desired results including clinical results, and may include even minimal changes or improvements in one or more measurable markers of the disease or condition being treated. A treatment is usually effective to reduce at least one symptom of a condition, disease, disorder, injury or damage. Exemplary markers of clinical improvement will be apparent to persons skilled in the art. Examples include, but are not limited to, one or more of the following: decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, decreasing the dose of one or more other medications required to treat the disease, and/or increasing the quality of life, etc.

"Prophylaxis," "prophylactic treatment," or "preventive treatment" refers to preventing or reducing the occurrence or severity of one or more symptoms and/or their underlying cause, for example, prevention of a disease or condition in a subject susceptible to developing a disease or condition (e.g., at a higher risk, as a result of genetic predisposition, environmental factors, predisposing diseases or disorders, or the like).

The term "disorder" or "disease" used interchangeably herein, refers to any alteration in the state of the body or one of its organs and/or tissues, interrupting or disturbing the performance of organ function and/or tissue function (e.g., causes organ dysfunction) and/or causing a symptom such as discomfort, dysfunction, distress, or even death to a subject afflicted with the disease.

By "pharmaceutically acceptable" is meant a material that is not biologically or otherwise undesirable, i.e., the material may be incorporated into a pharmaceutical composition administered to a patient without causing any significant undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

The term "effective amount" refers to the amount of one or more compounds that renders a desired treatment outcome. An effective amount may be comprised within one or more doses, i.e., a single dose or multiple doses may be required to achieve the desired treatment endpoint.

The term "therapeutically effective amount" as used herein, refers to the level or amount of one or more agents needed to treat a condition, or reduce or prevent injury or damage, optionally without causing significant negative or adverse side effects.

A "prophylactically effective amount" refers to an amount of an agent sufficient to prevent or reduce severity of a future disease or condition when administered to a subject who is susceptible and/or who may develop a disease or condition.

According to the methods of the present invention, the term "subject," and variants thereof as used herein, includes any subject that has, is suspected of having, or is at risk for having a disease or condition. Suitable subjects (or patients) include mammals, such as laboratory animals (e.g., mouse, rat, rabbit, guinea pig), farm animals, and domestic animals or pets (e.g., cat, dog). Non-human primates and, preferably, human patients, are included. A subject "at risk" may or may not have detectable disease, and may or may not have displayed detectable disease prior to the diagnostic or treatment methods described herein. "At risk" denotes that a subject has one or more so-called risk factors, which are measurable parameters that correlate with development of a condition described herein, which are described herein. A subject having one or more of these risk factors has a higher probability of developing a condition described herein than a subject without these risk factor(s). One example of such a risk factor is an increase or decrease in a biomarker of the present invention as compared to a clinically normal sample.

In certain embodiments, when measuring the activity level of a component in the CDX2-KLF4 signaling pathway of treatment, an "increased" or "decreased" amount or level may include a "statistically significant" amount. In some embodiments, the administration of an anti-cancer agent such as LOR-253 provides "statistically significant" therapeutic effect or clinical efficacy for treating the cancer. In some embodiments, such statistically significant therapeutic effect or clinical efficacy includes slower cancer cell proliferation or tumor growth caused by the anti-cancer agent as compared to a control vehicle. A result is typically referred to as statistically significant if it is unlikely to have occurred by chance. The significance level of a test or result relates traditionally to the amount of evidence required to accept that an event is unlikely to have arisen by chance. In certain cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see, e.g., Goodman S., *Ann Intern Med.* 130:1005-13, 1999). In some embodiments, an "increased" or "decreased" amount or level is about 1.1×, 1.2×, 1.3×, 1.4×, 1.5×, 2×, 2.5×, 3×, 3.5×, 4×, 4.5×, 5×, 6×, 7×, 8×, 9×, 10×, 15×, 20×, 25×, 30×, 40×, or 50× more or less the amount of a predetermined standard, or the amount of a determined time point relative to a previous or earlier timepoint.

According to some embodiments of the present invention, administering of anti-cancer agents such as LOR-253 according to the methods of the present invention provides statistically significant therapeutic effect. In one embodiment, the statistically significant therapeutic effect is determined based on one or more standards or criteria provided by one or more regulatory agencies in the United States, e.g., FDA or other countries. In other embodiments, the statistically significant therapeutic effect is determined based on results obtained from regulatory agency approved clinical trial set up and/or procedure.

In some embodiments, the statistically significant therapeutic effect is determined based on a patient population of at least 300, 400, 500, 600, 700, 800, 900, 1000 or 2000. In some embodiments, the statistically significant therapeutic effect is determined based on data obtained from randomized and double blinded clinical trial set up. In some embodiments, the statistically significant therapeutic effect is determined based on data with a p value of less than or equal to about 0.05, 0.04, 0.03, 0.02 or 0.01. In some embodiments, the statistically significant therapeutic effect is determined based on data with a confidence interval greater than or equal to 95%, 96%, 97%, 98% or 99%. In some embodiments, the statistically significant therapeutic effect is determined on approval of Phase III clinical trial of the methods provided by the present invention, e.g., by FDA in the US.

In some embodiments, the statistically significant therapeutic effect is determined by a randomized double blind clinical trial of a patient population of at least 300 or 350, treated with anti-cancer agents such as LOR-253 in combination with standard care. In some embodiment, the statistically significant therapeutic effect is determined by a randomized clinical trial of a patient population of at least 300 or 350 and using 28 day mortality rate, in-hospital mortality rate, ICU mortality rate, ICU duration, ICU free days, sequential organ failure assessment score (SOFA), relative risk of death, ICU frequency, duration of ventilation, frequency of ventilation, ventilation free days or any combination thereof or any other commonly accepted criteria for sepsis assessment.

In general, statistical analysis can include any suitable method permitted by a regulatory agency, e.g., FDA in the US or China or any other country. In some embodiments, statistical analysis includes non-stratified analysis, log-rank analysis, e.g., from Kaplan-Meier, Jacobson-Truax, Gulliken-Lord-Novick, Edwards-Nunnally, Hageman-Arrindel and Hierarchical Linear Modeling (HLM) and Cox regression analysis.

As used herein, the phrase "per day" describes an amount administered on those days when an agent is administered. The phrase "per day" does not indicate that an amount is administered every day.

The phrase "pharmaceutically acceptable salt(s)", as used herein, unless otherwise indicated, includes salts of acidic or basic groups which may be present in a compound. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the acetate, benzenesulfonate, benzoate, bicarbonate, bisulfate, bistosylate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodide, and valerate salts.

The term "prodrug", as used herein, unless otherwise indicated, means compounds that are drug precursors, which following administration, release the drug in vivo via some chemical or physiological process (e.g., a prodrug on being brought to the physiological pH is converted to the desired drug form).

"Continuous dosing schedule", as used herein, unless otherwise indicated, refers to a dosing schedule wherein compound of present invention, or a dosage form comprising said compound, is administered during a treatment period without a rest period. Throughout the treatment period of a continuous dosing schedule, the compound, or a dosage form comprising the compound, can be administered, for example, daily, every other day, every third day, every forth day, every fifth day, etc. On a day when compound, or a dosage form comprising the compound is administered, it can be administered in a single dose, or in multiple doses throughout the day.

"Intermittent dosing schedule", as used herein, unless otherwise indicated, refers to a dosing schedule that comprises a treatment period and a rest period. Throughout the treatment period of an intermittent dosing schedule, compound of present invention, or a dosage form comprising said compound, can be administered, for example, daily, or every other day, every third day, every forth day, every fifth day, etc. On a day when compound or a dosage form comprising the compound is administered, it can be administered in a single dose, or in multiple doses throughout the day. During the rest period, a compound or a dosage form comprising the compound is not administered. In some embodiments, the rest period lasts at least one day, at least two days, at least three days, at least four days, at least five days, at least six days, at least a week, at least 1.5 week, at least 2 weeks, at least 3 weeks, at least 4 weeks, at least one month, at least two months, at least three months, at least four months, at least five months, at least half year, at least one year, at least two years, or more. In some intermittent dosing regimens, the treatment period is typically from about 1 day to 30 days, such as about 10 days to 30 days, for example, about 2, 3 or 4 weeks, and the rest period is typically from 1 to 30 days, such as 3 to 15 days, for example, 1 or 2 weeks. The combination of any treatment period from 10 to 30 days with any rest period from 3 to 15 days is contemplated. Intermittent dosing regimens can be expressed as treatment period in weeks/rest period in weeks. For example, a 4/1 intermittent dosing schedule refers to an intermittent dosing schedule wherein the treatment period is four weeks and the rest period is one week. A 4/2 intermittent dosing schedule refers to an intermittent dosing schedule wherein the treatment period is four weeks and the rest period is two weeks. Similarly, a 3/1 intermittent dosing schedule refers to an intermittent dosing schedule wherein the treatment period is three weeks and the rest period is one week.

The human subject treated by the anti-cancer agent of the present invention may show complete response or partial response. Complete Response (CR), as used herein, unless otherwise indicated, refers to disappearance of all measurable and nonmeasurable symptoms and no appearance of new symptoms in a patient under the treatment. Partial Response (PR), as used herein, unless other wise indicated, refers to at least one measurable and nonmeasurable symptom is significantly reduced, or without appearance of new symptom in a patient under treatment.

It should be further appreciated that dosing regimens can be adjusted by one skilled in the art to more conveniently accommodate coordination of the dosing regimens, and additional therapeutic agents, if such adjustments are therapeutically acceptable.

As used herein, "$C_{max}$" refers to the maximum plasma concentration; $t_{max}$ refers to the time when the $C_{max}$ occurs following administering the dosage; AUC refers to area under the plasma concentration-time curve from time zero to infinity; $t_{1/2}$ refers to plasma elimination half-life; % CV refers to percent coefficient of variation; $C_{(trough\ 24\ h)}$ refers to trough plasma concentration at 24 hours after dosing; and QD indicates once daily.

Cancers

The cancers which can be treated in accordance with one embodiment of the present invention thus include, but are not limited to, leukaemias; adenocarcinomas and carcinomas, including squamous cell carcinomas. Carcinomas are also frequently referred to as "solid tumours," as described above, and examples of commonly occurring solid tumours that can be treated in accordance with the present invention include, but are not limited to, anal cancer, bladder cancer, colon cancer, colorectal cancer, duodenal cancer, gastric (stomach) cancer, lung (non-small cell) cancer, oesophageal cancer, prostate cancer, rectal cancer and small intestine cancer. Accordingly, one embodiment of the present invention provides for the use of a compound of Formula I in the treatment of a cancer selected from the group of leukemia, bladder cancer, lung (non-small cell) cancer, prostate cancer and a cancer of the GI tract, wherein cancers of the GI tract include, but are not limited to, anal cancer, colon cancer, colorectal cancer, duodenal cancer, gastric (stomach) cancer, oesophageal cancer, rectal cancer and small intestine cancer.

As used herein, "$C_{max}$" refers to the maximum plasma concentration; $t_{max}$ refers to the time when the $C_{max}$ occurs following administering the dosage; AUC refers to area under the plasma concentration-time curve from time zero to infinity; $t_{1/2}$ refers to plasma elimination half-life; % CV refers to percent coefficient of variation; $C_{(trough\ 24\ h)}$ refers to trough plasma concentration at 24 hours after dosing; and QD indicates once daily.

The term "leukaemia" or "leukemia" refers broadly to progressive, malignant diseases of the blood-forming organs. Leukaemia is typically characterized by a distorted proliferation and development of leukocytes and their precursors in the blood and bone marrow but can also refer to malignant diseases of other blood cells such as erythroleukaemia, which affects immature red blood cells. Leukaemia is generally clinically classified on the basis of (1) the duration and character of the disease—acute or chronic; (2) the type of cell involved—myeloid (myelogenous), lymphoid (lymphogenous) or monocytic, and (3) the increase or non-increase in the number of abnormal cells in the blood—leukaemic or aleukaemic (subleukaemic). Leukaemia includes, for example, acute leukaemia, chronic leukaemia, adult leukaemia, pediatric/child leukaemia, lymphocytic leukemia, myeloid leukemia, acute lymphocytic leukemia (ALL), acute nonlymphocytic leukaemia, chronic lymphocytic leukaemia, acute granulocytic leukaemia, chronic granulocytic leukaemia, acute promyelocytic leukaemia, chronic myelogenous leukemia (CML), T-cell leukaemia, B-cell leukaemia, adult T-cell leukaemia, pediatric T-cell ALL, pediatric B-cell ALL, aleukaemic leukaemia, aleukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "carcinoma" refers to a malignant new growth made up of epithelial cells tending to infiltrate the surrounding tissues and give rise to metastases. The term "carcinoma" also encompasses adenocarcinomas. Adenocarcinomas are carcinomas that originate in cells that make organs which have glandular (secretory) properties or that originate in cells that line hollow viscera, such as the gastrointestinal tract or bronchial epithelia, and include adenocarcinomas of the lung and prostate.

Methods of the present invention can be applied in the treatment of early stage cancers including early neoplasias that may be small, slow growing, localized and/or nonaggressive, for example, with the intent of curing the disease or causing regression of the cancer, as well as in the treatment of intermediate stage and in the treatment of late stage cancers including advanced and/or metastatic and/or aggressive neoplasias, for example, to slow the progression of the disease, to reduce metastasis or to increase the survival of the patient. Similarly, the combinations may be used in the treatment of low grade cancers, intermediate grade cancers and or high grade cancers.

Methods of the present invention can also be used in the treatment of indolent cancers, recurrent cancers including locally recurrent, distantly recurrent and/or refractory cancers (i.e. cancers that have not responded to treatment), metastatic cancers, locally advanced cancers and aggressive cancers. Thus, an "advanced" cancer includes locally advanced cancer and metastatic cancer and refers to overt disease in a patient, wherein such overt disease is not amenable to cure by local modalities of treatment, such as surgery or radiotherapy. The term "metastatic cancer" refers to cancer that has spread from one part of the body to another. Advanced cancers may also be unresectable, that is, they have spread to surrounding tissue and cannot be surgically removed.

Methods of the present invention can also be used in the treatment of drug resistant cancers, including multidrug resistant tumours. As is known in the art, the resistance of cancer cells to chemotherapy is one of the central problems in the management of cancer.

One skilled in the art will appreciate that many of these categories may overlap, for example, aggressive cancers are typically also metastatic. "Aggressive cancer," as used herein, refers to a rapidly growing cancer. One skilled in the art will appreciate that for some cancers, such as breast cancer or prostate cancer the term "aggressive cancer" will refer to an advanced cancer that has relapsed within approximately the earlier two-thirds of the spectrum of relapse times for a given cancer, whereas for other types of cancer, nearly all cases present rapidly growing cancers which are considered to be aggressive. The term can thus cover a subsection of a certain cancer type or it may encompass all of other cancer types.

In some embodiments, the cancer is leukemia/lymphoma. In some embodiments, the cancer is acute myelogenous leukemia (AML). In some embodiments, the cancer is lymphoma, gastric cancer, multiple myeloma, myelodysplastic syndromes, or combinations thereof. In some other embodiments, the cancer is T-cell leukemia, e.g., adult T-cell leukemia associated with epigenetic methylation of KLF4 gene. In some other embodiments, the cancer is ALL, e.g., pediatric ALL. In some other embodiments, the cancer is pediatric T-cell ALL associated with one or more mutations in KLF4 gene or protein. In some other embodiments, the cancer is pediatric B-cell ALL associated with elevated miRNA-2902. In some other embodiments, the cancer is AML, ALL or MDS, e.g., high risk MDS, all of which associated with higher than normal CDX2 activity. In some other embodiments, the cancer is Hodgkins, Burkitts, or B-cell lymphomas, all of which associated with methylation of KLF4 gene.

Acute myeloid leukemia (AML): also known as acute myelogenous leukemia or acute nonlymphocytic leukemia (ANLL), is a cancer of the myeloid line of blood cells, characterized by the rapid growth of abnormal white blood cells that accumulate in the bone marrow and interfere with the production of normal blood cells. The symptoms of AML are caused by replacement of normal bone marrow with leukemic cells, which causes a drop in red blood cells, platelets, and normal white blood cells. These symptoms include fatigue, shortness of breath, easy bruising and bleeding, and increased risk of infection. Several risk factors and chromosomal abnormalities have been identified, but the specific cause is not clear. As an acute leukemia, AML progresses rapidly and is typically fatal within weeks or months if left untreated. Several risk factors for developing AML include, but are not limited to, preleukemic blood disorders, such as myelodysplastic syndrome or myeloproliferative disease; exposure to anticancer chemotherapy; radiation, such as high amounts of ionizing radiation exposure; and genetic reasons, such as those described in Taylor et al. ("The hereditary basis of human leukemia". In Henderson E S, Lister T A, Greaves M F. Leukemia (6th ed.). Philadelphia: W B Saunders. p. 210. ISBN 0-7216-5381-2), Horwitz et al. ("Anticipation in familial leukemia". Am. J. Hum. Genet. 59 (5): 990-8. PMC 1914843. PMID 8900225), Crittenden ("An interpretation of familial aggregation based on multiple genetic and environmental factors". Ann. N. Y. Acad. Sci. 91 (3): 769-80), and Horwitz ("The genetics of familial leukemia". Leukemia 11 (8): 1347-59). The World Health Organization (WHO) classification of acute myeloid leukemia attempts to be more clinically useful and to produce more meaningful prognostic information than the FAB criteria. Each of the WHO categories contains numerous descriptive subcategories of interest to the hematopathologist and oncologist; however, most of the clinically significant information in the WHO schema is communicated via categorization into one of the subtypes listed below:

| Name | Description | ICD-O (International Classification of Diseases for Oncology) |
|---|---|---|
| Acute myeloid leukemia with recurrent genetic abnormalities | Includes: AML with translocations between chromosome 8 and 21 [t(8; 21)] (ICD-O 9896/3); RUNX1/RUNX1T1 AML with inversions in chromosome 16 [inv(16)] (ICD-O 9871/3); CBFB/MYH11 APL with translocations between chromosome 15 and 17 [t(15; 17)] (ICD-O 9866/3); RARA; PML AML with translocations in chromosomes 9 and 11 [t(9; 11)] MLLT3-MLL Patients with AML in this category generally have a high rate of remission and a better prognosis compared to other types of AML. | Multiple |
| AML with multilineage dysplasia | This category includes patients who have had a prior myelodysplastic syndrome (MDS) or myeloproliferative disease (MPD) that transforms into AML. This category of AML occurs most often in elderly patients and often has a worse prognosis. | M9895/3 |
| AML and MDS, therapy-related | This category includes patients who have had prior chemotherapy and/or radiation and subsequently develop AML or MDS. These leukemias may be characterized by specific chromosomal abnormalities, and often carry a worse prognosis. | M9920/3 |
| AML not otherwise categorized | Includes subtypes of AML that do not fall into the above categories. | M9861/3 |

The French-American-British (FAB) classification system divides AML into eight subtypes, M0 through to M7, based on the type of cell from which the leukemia developed and its degree of maturity. Although the WHO classification (see above) may be more useful, the FAB system is still widely used.

| Type | Name | Cytogenetics | Percentage of adult AML patients |
|---|---|---|---|
| M0 | acute myeloblastic leukemia, minimally differentiated | | 5% |
| M1 | acute myeloblastic leukemia, without maturation | | 15% |
| M2 | acute myeloblastic leukemia, with granulocytic maturation | t(8; 21)(q22; q22), t(6; 9) | 25% |
| M3 | promyelocytic, or acute promyelocytic leukemia (APL) | t(15; 17) | 10% |
| M4 | acute myelomonocytic leukemia | inv(16)(p13q22), del(16q) | 20% |
| M4eo | myelomonocytic together with bone marrow eosinophilia | inv(16), t(16; 16) | 5% |
| M5 | acute monoblastic leukemia (M5a) or acute monocytic leukemia (M5b) | del (11q), t(9; 11), t(11; 19) | 10% |
| M6 | acute erythroid leukemias, including erythroleukemia (M6a) and very rare pure erythroid leukemia (M6b) | | 5% |
| M7 | acute megakaryoblastic leukemia | t(1; 22) | 5% |

Previous methods for treating AML are described in Bishop J ("The treatment of adult acute myeloid leukemia". Semin Oncol 24 (1): 57-69. 1997), Weick et al. ("A randomized investigation of high-dose versus standard-dose cytosine arabinoside with daunorubicin in patients with previously untreated acute myeloid leukemia: a Southwest Oncology Group study" (PDF). Blood 88 (8): 2841-51, 1996), Bishop et al. ("A randomized study of high-dose cytarabine in induction in acute myeloid leukemia" Blood 87 (5): 1710-7, 1996), Huang et al. ("Use of all-trans retinoic acid in the treatment of acute promyelocytic leukemia". Blood 72 (2): 567-72, 1988), Tallman et al. ("All-trans-retinoic acid in acute promyelocytic leukemia". N. Engl. J. Med. 337 (15): 1021-8, 1997), Fenaux et al. ("A randomized comparison of all transretinoic acid (ATRA) followed by chemotherapy and ATRA plus chemotherapy and the role of maintenance therapy in newly diagnosed acute promyelocytic leukemia. The European APL Group". Blood 94 (4): 1192-200, 1999), Estey E ("Treatment of acute myelogenous leukemia". Oncology (Williston Park) 16 (3): 343-52, 355-6; discussion 357, 362, 365-6, 2002), and Cassileth et al. ("Maintenance chemotherapy prolongs remission duration in adult acute nonlymphocytic leukemia". J Clin Oncol 6 (4): 583-7, 1988).

Acute lymphocytic leukemia (ALL): also known as acute lymphoblastic leukemia, is an acute leukemia that is characterized by dysregulated proliferation and accumulation of leukemic lymphocytes/lymphoblasts (immature white blood cells such as early B- and T-lymphocyte progenitors) in the bone marrow and various extramedullary sites. ALL is the most common type of cancer in children, and it is a relatively uncommon cancer in adults. Risk factors for developing ALL include, but are not limited to, genetic disorders/mutations and various epigenetic modifications such as those described by Iacobucci et al. ("Cytogenetic and molecular predictors of outcome in acute lymphocytic leukemia: recent developments", Curr Hematol Malig Rep. 2012 June; 7(2):133-43.) and Florean et al. ("Epigenomics of leukemia: from mechanisms to therapeutic applications". Epigenomics. 2011 October; 3(5):581-609).

Chronic myelogenous leukemia (CML): also known as chronic myeloid leukemia, is a chronic leukemia that is characterized by dysregulated/increased proliferation of various blood cells, predominantly myeloid cells in peripheral blood, and their precursors in the bone marrow, resulting in their accumulation in the blood. It is less frequent than chronic lymphocytic leukemia (CLL) in adults in the Western world, and the median age of CML onset is 50-60 years. Risk factors for developing CML also include, but are not limited to, genetic disorders/mutations and various epigenetic modifications such as those described by Florean et al. The disease course is triphasic, starting with an early phase, also known as chronic phase (CP) disease. Then, leukemia stem cells can acquire additional genetic defects.

Adult T-cell leukaemia (ATLL): also known as adult T-cell lymphoma, is an uncommon lymphoproliferative disorder of mature CD4+ T cells that is caused by the retrovirus human T-lymphotrophic virus type 1 (HTLV-1) as reviewed by Qayyum et al. ("Adult T-cell leukemia/lymphoma". Arch Pathol Lab Med. 2014 February; 138(2):282-6). Presently, about 20 million people worldwide are HTLV-1 carriers, with most infected individuals residing in endemic areas such as southern Japan, Africa, the Caribbean basin, and Latin America. The lifelong viral carrier state and long latency (20-40 years) are common after HTLV-1 infection, therefore this type of leukemia/lymphoma is almost exclusively found in adults and is extremely rare in children. The lifetime risk of progression to ATLL in an HTLV-1—positive patient is 2.1% for women and 6.6% for men. The mean age of onset is 60 years old (range, 20-80 years old). The overwhelming majority of ATLL cases occur in patients infected during the early years of life, presumably because of a less efficient immune response in this age group. In addition, the prolonged infection may increase chances of accruing subsequent mutations, and ultimately malignant transformation. Major paths of viral transmission are breast feeding, blood exposure, and unprotected sex. The World Health Organization Classification of Tumors of Hematopoietic and Lymphoid Tissues in 2008 subclassified ATLL into 4 distinct variants according to the Shimoyama classification: acute (60%), lymphomatous (20%), chronic (15%), and smoldering (5%). There are no absolutely necessary features for each variant, and overlap is seen. The acute variant manifests as marked leukocytosis with atypical lymphocytes and eosinophilia. Symptoms include hypercalcemia with or without osteolytic lesions, renal dysfunction and neuropsychiatric disturbances, elevated lactate dehydrogenase level, central nervous ring-enhancing lesions, and secondary respiratory complications. The lymphomatous variant is an aggressive advanced disease resembling acute-onset subtype, and marked lymphadenopathy without leukemia is a prominent feature of this variant. The chronic variant typically presents with skin rash, leukocytosis with absolute lymphocytosis, mild lymphadenopathy, and hypercalcemia. The smoldering variant is asymptomatic and is characterized by normal white blood cell count with less than 5% circulating atypical lymphoid cells and without associated hypercalcemia or organomegaly, although skin and pulmonary involvement often occur. Progression from the smoldering variant to the acute variant can occur.

Lymphoma: Lymphoma is a type of blood cancer that occurs when B or T lymphocytes, the white blood cells that form a part of the immune system and help protect the body from infection and disease, divide faster than normal cells or live longer than they are supposed to. Typically, lymphoma presents as a solid tumor of lymphoid cells. The current WHO classification, published in 2001 and updated in 2008, is the latest classification of lymphoma and is based upon the foundations laid within the "Revised European-American Lymphoma classification" (REAL):

A. Mature B-Cell Neoplasms:
 Chronic lymphocytic leukemia/Small lymphocytic lymphoma
 B-cell prolymphocytic leukemia
 Lymphoplasmacytic lymphoma (such as Waldenström macroglobulinemia)
 Splenic marginal zone lymphoma
 Plasma cell neoplasms:
  Plasma cell myeloma
  Plasmacytoma
  Monoclonal immunoglobulin deposition diseases
  Heavy chain diseases
 Extranodal marginal zone B cell lymphoma, also called MALT lymphoma
 Nodal marginal zone B cell lymphoma (NMZL)
 Follicular lymphoma
 Mantle cell lymphoma
 Diffuse large B cell lymphoma
 Mediastinal (thymic) large B cell lymphoma
 Intravascular large B cell lymphoma
 Primary effusion lymphoma
 Burkitt lymphoma/leukemia B. Mature T Cell and Natural Killer (NK) Cell Neoplasms
T cell prolymphocytic leukemia
T cell large granular lymphocytic leukemia
Aggressive NK cell leukemia
Adult T cell leukemia/lymphoma
Extranodal NK/T cell lymphoma, nasal type
Enteropathy-type T cell lymphoma
Hepatosplenic T cell lymphoma
Blastic NK cell lymphoma
Mycosis fungoides/Sezary syndrome
Primary cutaneous CD30-positive T cell lymphoproliferative disorders
    Primary cutaneous anaplastic large cell lymphoma
    Lymphomatoid papulosis
Angioimmunoblastic T cell lymphoma
Peripheral T cell lymphoma, unspecified
Anaplastic large cell lymphoma
C. Hodgkin Lymphoma
Classical Hodgkin lymphomas:
    Nodular sclerosis
    Mixed cellularity
    Lymphocyte-rich
    Lymphocyte depleted or not depleted
Nodular lymphocyte-predominant Hodgkin lymphoma
D. Immunodeficiency-Associated Lymphoproliferative Disorders
    Associated with a primary immune disorder
    Associated with the Human Immunodeficiency Virus (HIV)
    Post-transplant
    Associated with methotrexate therapy
    Primary central nervous system lymphoma occurs most often in immuno-compromised patients, in particular those with AIDS, but it can occur in the immunocompetent as well. It has a poor prognosis, particularly in those with AIDS. Treatment can consist of corticosteroids, radiotherapy, and chemotherapy, often with methotrexate.

Subtypes of lymphoma with relative incidence, histopathology, immunophenotype, overall t-year survival are show below (*Robbins basic pathology* (8th ed.). Philadelphia: Saunders/Elsevier. 2007. pp. Table 12-8.):

| Lymphoma type | Relative incidence[13] | Histopathology[13] | Immuno-phenotype | Overall 5-year survival | Other comments |
| --- | --- | --- | --- | --- | --- |
| Precursor T-cell leukemia/lymphoma | 40% of lymphomas in childhood. | Lymphoblasts with irregular nuclear contours, condensed chromatin, small nucleoli and scant cytoplasm without granules. | TdT, CD2, CD7 | | It often presents as a mediastinal mass because of involvement of the thymus. It is highly associated with NOTCH1 mutations. Most common in adolescent males. |
| Follicular lymphoma | 40% of lymphomas in adults | Small "cleaved" cells (centrocytes) mixed with large activated cells (centroblasts). Usually nodular ("follicular") growth pattern | CD10, surface Ig | 72-77% | Occurs in older adults. Usually involves lymph nodes, bone marrow and spleen. Associated with t(14; 18) translocation overexpressing Bcl-2. Indolent |
| Diffuse large B cell lymphoma | 40 to 50% of lymphomas in adults | Variable. Most resemble B cells of large germinal centers. Diffuse growth pattern. | Variable expression of CD10 and surface Ig | 60% | Occurs in all ages, but most commonly in older adults. Often occurs outside lymph nodes. Aggressive. |
| Mantle cell lymphoma | 3 to 4% of lymphomas in adults | Lymphocytes of small to intermediate size growing in diffuse pattern | CD5 | 50% to 70% | Occurs mainly in adult males. Usually involves lymph nodes, bone marrow, spleen and GI tract. Associated with t(11; 14) translocation overexpressing cyclin D1. Moderately aggressive. |
| B-cell chronic lymphocytic leukemia/lymphoma | 3 to 4% of lymphomas in adults | Small resting lymphocytes mixed with variable number of large activated cells. Lymph nodes are diffusely effaced | CD5, surface immuno-globulin | 50% | Occurs in older adults. Usually involves lymph nodes, bone marrow and spleen. Most patients have peripheral blood involvement. Indolent. |

-continued

| Lymphoma type | Relative incidence[13] | Histopathology[13] | Immuno-phenotype | Overall 5-year survival | Other comments |
| --- | --- | --- | --- | --- | --- |
| MALT lymphoma | ~5% of lymphomas in adults | Variable cell size and differentiation. 40% show plasma cell differentiation. Homing of B cells to epithelium creates lymphoepithelial lesions. | CD5, CD10, surface Ig | | Frequently occurs outside lymph nodes. Very indolent. May be cured by local excision. |
| Burkitt's lymphoma | <1% of lymphomas in the United States | Round lymphoid cells of intermediate size with several nucleoli. Starry-sky appearance by diffuse spread with interspersed apoptosis. | CD10, surface Ig | 50% | Endemic in Africa, sporadic elsewhere. More common in immunocompromised and in children. Often visceral involvement. Highly aggressive. |
| Mycosis fungoides | Most common cutaneous lymphoid malignancy | Usually small lymphoid cells with convoluted nuclei that often infiltrate the epidermis, creating Pautrier microabscesseses. | CD4 | 75% | Localized or more generalized skin symptoms. Generally indolent. In a more aggressive variant, Sézary's disease, there is skin erythema and peripheral blood involvement. |
| Peripheral T-cell lymphoma-Not-Otherwise-Specified | Most common T cell lymphoma | Variable. Usually a mix small to large lymphoid cells with irregular nuclear contours. | CD3 | | Probably consists of several rare tumor types. It is often disseminated and generally aggressive. |
| Nodular sclerosis form of Hodgkin lymphoma | Most common type of Hodgkin's lymphoma | Reed-Sternberg cell variants and inflammation, usually broad sclerotic bands that consists of collagen. | CD15, CD30 | | Most common in young adults. It often arises in the mediastinum or cervical lymph nodes. |
| Mixed-cellularity subtype of Hodekin lymphoma | Second most common form of Hodgkin's lymphoma | Many classic Reed-Sternberg cells and inflammation | CD15, CD30 | | Most common in men. More likely to be diagnosed at advanced stages than the nodular sclerosis form. Epstein-Barr virus involved in 70% of cases. |

Gastric cancer: a.k.a. stomach cancer, which refers to cancer arising from any part of the stomach. Stomach cancer is often either asymptomatic (producing no noticeable symptoms) or it may cause only nonspecific symptoms (symptoms which are not specific to just stomach cancer, but also to other related or unrelated disorders) in its early stages. It can be diagnosed by gastroscopic exam, upper GI series, or computed tomography or CT scanning. It is previously treated by surgery, chemotherapy, and radiation.

Colorectal cancer: a.k.a. colon cancer, rectal cancer, bowel cancer or colorectal adenocarcinoma, is a cancer from uncontrolled cell growth in the colon or rectum (parts of the large intestine), or in the appendix. Greater than 75-95% of colon cancer occurs in people with little or no genetic risk. Other risk factors include older age, male gender, high intake of fat, alcohol or red meat, obesity, smoking and a lack of physical exercise. Approximately 10% of cases are linked to insufficient activity. The risk for alcohol appears to increase at greater than one drink per day. Colorectal cancer is a disease originating from the epithelial cells lining the colon or rectum of the gastrointestinal tract, most frequently as a result of mutations in the Wnt signaling pathway that artificially increase signaling activity. The mutations can be inherited or are acquired, and most probably occur in the intestinal crypt stem cell. Genes in the Wnt signaling pathway that are related to colorectal cancer include, but are not limited to, APC, β-catenin, AXIN1, AXIN2, TCF7L2, or NKD1. Beyond the defects in the Wnt-APC-beta-catenin signaling pathway, other mutations must occur for the cell to become cancerous. The p53 protein, produced by the TP53 gene, normally monitors cell division and kills cells if they have Wnt pathway defects. Eventually, a cell line acquires a mutation in the TP53 gene and transforms the tissue from an adenoma into an invasive carcinoma. Other apoptotic proteins commonly deactivated in colorectal cancers are TGF-β and DCC. Other oncogenes overexpressed in colorectal cancer include, genes encoding the proteins KRAS, RAF, and PI3K, which normally stimulate the cell to divide in response to growth factors, can acquire mutations that result in over-activation of cell proliferation. In addition to the oncogenic and inactivating mutations described for the genes above, non-hypermutated samples also contain mutated CTNNB1, FAM123B, SOX9, ATM, and ARID1A. Progressing through a distinct set of genetic events, hypermutated tumors display mutated forms of ACVR2A, TGFBR2, MSH3, MSH6, SLC9A9, TCF7L2, and BRAF. The common theme among these genes, across both tumor types, is their involvement in WNT and TGF-β signaling pathways, which in turn results in increased activity of MYC, a central player in colorectal cancer.

Multiple myeloma: a.k.a. plasma cell myeloma or Kahler's disease is a cancer of plasma cells, a type of white blood cell normally responsible for producing antibodies. It can be symptomatic myeloma, asymptomatic myeloma and MGUS (monoclonal gammopathy of undetermined significance). Myeloma is diagnosed with blood tests (serum protein electrophoresis, serum free kappa/lambda light chain assay), bone marrow examination, urine protein electrophoresis, and X-rays of commonly involved bones. It is previously treated by steroids, chemotherapy, proteasome inhibitors, immunomodulatory drugs (IMiDs) such as thalidomide or lenalidomide, and stem cell transplants.

Myelodysplastic syndromes (MDS): Myelodysplastic syndrome ("MDS") refers to a diverse group of hematopoietic stem cell disorders, which are hematological (blood-related) medical conditions with ineffective production (or dysplasia) of the myeloid class of blood cells. MDS is characterized by a cellular marrow with impaired morphology and maturation (dysmyelopoiesis), peripheral blood cytopenias, and a variable risk of progression to acute leukemia, resulting from ineffective blood cell production. *The Merck Manual* 953 (17$^{th}$ ed. 1999) and List et al., 1990, *J. Clin. Oncol.* 8:1424. Some types of MDS, referred to as "low-risk MDS", progress slowly and may cause mild to moderate anemia, or decrements to other types of cells. Some other types of MDS are called "high-risk MDS" and may cause severe problems. In patients with high-risk MDS, immature cells called blast cells make up more than five percent of the cells in the marrow and do not develop into normal red cells, white cells and platelets, often causing more severe deficiency in those cells/platelets. When MDS patients develop more than 20 percent blast cells, they are reclassified as having AML with trilineage dysplasia (AML-TLD).

The initial hematopoietic stem cell injury can be from causes such as, but not limited to, cytotoxic chemotherapy, radiation, virus, chemical exposure, and genetic predisposition. A clonal mutation predominates over bone marrow, suppressing healthy stem cells. In the early stages of MDS, the main cause of cytopenias is increased programmed cell death (apoptosis). As the disease progresses and converts into leukemia, gene mutation rarely occurs and a proliferation of leukemic cells overwhelms the healthy marrow. The disease course differs, with some cases behaving as an indolent disease and others behaving aggressively with a very short clinical course that converts into an acute form of leukemia. Patients with MDS can develop severe anemia and require blood transfusions. In some cases, the disease worsens and the patient develops cytopenias (low blood counts) caused by progressive bone marrow failure.

According to French-American-British classification published in 1976, which was revised in 1982, cases were classified into five categories:

| ICD-O | Name | Description |
| --- | --- | --- |
| M9980/3 | Refractory anemia (RA) | characterized by less than 5% primitive blood cells (myeloblasts) in the bone marrow and pathological abnormalities primarily seen in red cell precursors |
| M9982/3 | Refractory anemia with ring sideroblasts (RARS) | also characterized by less than 5% myeloblasts in the bone marrow, but distinguished by the presence of 15% or greater red cell precursors in the marrow being abnormal iron-stuffed cells called "ringed sideroblasts" |
| M9983/3 | Refractory anemia with excess blasts (RAEB) | characterized by 5-20% myeloblasts in the marrow |
| M9984/3 | Refractory anemia with excess blasts in transformation (RAEB-T) | characterized by 21-30% myeloblasts in the marrow (>30% blasts is defined as acute myeloid leukemia) |
| M9945/3 | Chronic myelomonocytic leukemia (CMML), not to be confused with chronic myelogenous leukemia or CML | characterized by less than 20% myeloblasts in the bone marrow and greater than 1*109/L monocytes (a type of white blood cell) circulating in the peripheral blood. |

The World Health Organization (WHO) modified this classification, introducing several new disease categories and eliminating others. Most recently the WHO has evolved a new classification scheme (2008) which is based more on genetic findings:

| Old system | New system |
| --- | --- |
| Refractory anemia (RA) | Refractory cytopenia with unilineage dysplasia (Refractory anemia, Refractory neutropenia, and Refractory thrombocytopenia) |
| Refractory anemia with ringed sideroblasts (RARS) | Refractory anemia with ring sideroblasts (RARS) Refractory anemia with ring sideroblasts—thrombocytosis (RARS-t) (provisional entity) which is in essence a myelodysplastic/myeloproliferative disorder and usually has a JAK2 mutation (Janus kinase)—New WHO classification 2008 Refractory cytopenia with multilineage dysplasia (RCMD) includes the subset Refractory cytopenia with multilineage dysplasia and ring sideroblasts (RCMD-RS). RCMD includes patients with pathological changes not restricted to red cells (i.e., prominent white cell precursor and platelet precursor (megakaryocyte) dysplasia. |

| Old system | New system |
|---|---|
| Refractory anemia with excess blasts (RAEB) | Refractory anemia with excess blasts I and II. RAEB was divided into *RAEB-I (5-9% blasts) and RAEB-II (10-19%) blasts, which has a poorer prognosis than RAEB-I. Auer rods may be seen in RAEB-II which may be difficult to distinguish from acute myeloid leukemia. |
| Refractory anemia with excess blasts in transformation (RAEB-T) | The category of RAEB-T was eliminated; such patients are now considered to have acute leukemia. 5q-syndrome, typically seen in older women with normal or highp latelet counts and isolated deletions of the long arm of chromosome 5 in bone marrow cells, was added to the classification. |
| Chronic myelomonocytic leukemia (CMML) | CMML was removed from the myelodysplastic syndromes and put in a new category of myelodysplastic—myeloproliferative overlap syndromes. |
| | 5q-syndrome<br>Myelodysplasia unclassifiable (seen in those cases of megakaryocyte dysplasia with fibrosis and others)<br>Refractory cytopenia of childhood (dysplasia in childhood)—New WHO classification 2008 |

Signs and symptoms of MDS include, but are not limited to, anemia (low red blood cell count or reduced hemoglobin), with chronic tiredness, shortness of breath, chilled sensation, sometimes chest pain; weakness or feeling tired, paler skin, easy bruising or bleeding, petechiae, fever, neutropenia (low neutrophil count), with increased susceptibility to infection; thrombocytopenia (low platelet count), with increased susceptibility to bleeding and ecchymosis (bruising), as well as subcutaneous hemorrhaging resulting in purpura or petechia; splenomegaly or rarely hepatomegaly; abnormal granules in cells, abnormal nuclear shape and size; and/or chromosomal abnormalities, including chromosomal translocations and abnormal chromosome number.

Many factors can increase risk of MDS, which include, but are not limited to, being male or white, being older than 60 years, past treatment with chemotherapy or radiation therapy, being exposed to certain chemicals, including tobacco smoke, pesticides, and solvents such as benzene, and being exposed to heavy metals, such as mercury or lead.

Previous treatment methods for MDS include bone marrow transplantation, use of hematopoietic growth factors or cytokines to stimulate blood cell development in a recipient, such as erythropoietin (EPO), granulocyte macrophage colony stimulating factor (GM-CSF), and granulocyte colony stimulating factor (G-CSF) (Metcalf, 1985, Science 229:16; Dexter, 1987, J. Cell Sci. 88:1; Golde and Gasson, 1988, Scientific American, July: 62; Tabbara and Robinson, 1991, Anti-Cancer Res. 11:81; Ogawa, 1989, Environ. Health Presp. 80:199; and Dexter, 1989, Br. Med. Bull. 45:337.). Unfortunately, bone transplantation is painful for donor and recipient, and hematopoietic growth factors have not proven effective in many clinical settings. Other methods include 5-azacytidine, decitabine, lenalidomide, immunosuppression, leukemia therapy, and investigational approaches.

In some embodiments, the histology of the cancer is determined before, during or after the treatment. Any suitable test can be used to determine the histology of the cancer. Such test and examination include, but are not limited to, common signs and symptoms of esophageal cancer, including but not limited to, backwards movement of food through the esophagus and possibly mouth (regurgitation), chest pain not related to eating, difficulty swallowing solids or liquids, heartburn, vomiting blood, hoarseness, chronic cough, hiccups, pneumonia, bone pain, bleeding into the esophagus, and weight loss, medical history and physical exam, imaging tests, chest X-ray, computed tomography (CT) scan, magnetic resonance imaging (MRI) scan, positron emission tomography (PET) scan, bone scan, sputum cytology, needle biopsy, bronchoscopy, endobronchial ultrasound, endoscopic esophageal ultrasound, mediastinoscopy and mediastinotomy, thoracentesis, thoracoscopy, immunohistochemistry, molecular tests, blood tests, barium swallow, endoscopic ultrasound, esophaogastroduodenoscopy (EGD) and biopsy, or any suitable methods derived from thereof.

CDX2-KLF4 Signaling Pathway

The term "CDX2-KLF4 signaling pathway" as used herein refers to a group of biological molecules that work together to control one or more cellular functions through CDX2 and/or KLF4, or by affecting the expression or activity of CDX2 or KLF4 as described herein, directly or indirectly. Sometimes the expression level and/or activity of CDX2 and/or KLF4 is also referred to as "CDX2-KLF4 axis".

CDX2, a.k.a. Caudal Type Homeobox 2, CDX3, Caudal Type HomeoBox Transcription Factor 2, Caudal-Type Homeobox Protein 2, or Homeobox Protein CDX-2, is a member of the caudal-related homeobox transcription factor gene family. The encoded protein is a major regulator of intestine-specific genes involved in cell growth and differentiation. This protein also plays a role in early embryonic development of the intestinal tract. Aberrant expression of this gene is associated with intestinal inflammation and tumorigenesis. Diseases associated with CDX2 include atrophic gastritis, and signet ring cell adenocarcinoma, and among its related super-pathways are Transcription Role of VDR in regulation of genes involved in osteoporosis and Cytoskeleton remodeling Regulation of actin cytoskeleton by Rho GTPases. GO annotations related to this gene include transcription regulatory region sequence-specific DNA binding and sequence-specific DNA binding transcription factor activity. An important paralog of this gene is CDX1. It is involved in the transcriptional regulation of multiple genes expressed in the intestinal epithelium, and important in broad range of functions from early differentiation to maintenance of the intestinal epithelial lining of both the small and large intestine. DNA and protein sequences of human CDX2 were previously reported, see GenBank Nos. NC_000013.10, NC_018924.2, NT_024524.14, NP_001256.3, ENSP00000370408, and Uniprot No. Q99626, each of which is incorporated herein by reference in its entirety for all purposes. Such sequences can be utilized to design procedures for detection and analysis of the level of CDX2 activity by ways known to one skilled in the art. CDX2 is aberrantly expressed in most cases of acute myeloid leukemia and promotes leukemogenesis (Scholl et al., The Journal of Clinical Investigation, 17(4): 1037-1048), with an mRNA copy numbers varied between about 30 copies to about 89,000 copies. As used herein, the phrase "CDX2 gene is turned on" or "CDX2 activity is on" refers to that the mRNA copies of CDX2 in a human subject is at least about 30 copies. Otherwise, the CDX2 gene is considered as being turned off.

Krüppel-Like Factor 4 (KLF4), a.k.a. Gut, EZF, GKLF, Epithelial Zinc Finger Protein EZF, Gut-Enriched Krueppel-Like Factor, Endothelial Krüppel-Like Zinc Finger Protein, or Krueppel-Like Factor 4, is associated with diseases including, but are not limited to, leukemia, skin squamous cell carcinoma, and familial adenomatous polyposis. An important paralog of this gene is KLF1. KLF4 can act both as activator and as repressor. It binds the 5'-CACCC-3' core sequence, such as the promoter region of its own gene. It regulates the expression of key transcription factors during embryonic development, and plays an important role in maintaining embryonic stem cells, and in preventing their differentiation. It is required for establishing the barrier function of the skin and for postnatal maturation and maintenance of the ocular surface. It is also involved in the differentiation of epithelial cells and may also function in skeletal and kidney development. It further contributes to the down-regulation of p53/TP53 transcription, and induction of p21. DNA and protein sequences of human KLF4 were previously reported, see GenBank Nos. NC_000009.11, NT_008470.19, NC_018920.2, and Uniprot No. O43474, each of which is incorporated herein by reference in its entirety for all purposes. Such sequences can be utilized to design procedures for detection and analysis of the level of KLF4 activity by ways known to one skilled in the art.

p21, a.k.a. Cyclin-Dependent Kinase Inhibitor 1A, Cip1, CDJN1, CIP1, WAF1, CAP20, MDA-6, SDI1, CDK-interacting protein 1, CDK-interaction protein 1, cyclin-dependent kinase inhibitor 1, DNA synthesis inhibitor, Melanoma Differentiation Associated Protein, p21CIP, wild type P53-activated fragment, mDA6, or PCI1, encodes a potent cyclin-dependent kinase inhibitor. The encoded protein binds to and inhibits the activity of cyclin-CDK2 or -CDK4 complexes, and thus functions as a regulator of cell cycle progression at G1. The expression of this gene is tightly controlled by the tumor suppressor protein p53, through which this protein mediates the p53-dependent cell cycle G1 phase arrest in response to a variety of stress stimuli. This protein can interact with proliferating cell nuclear antigen (PCNA), a DNA polymerase accessory factor, and plays a regulatory role in S phase DNA replication and DNA damage repair. This protein was reported to be specifically cleaved by CASP3-like spases, which thus leads to a dramatic activation of CDK2, and may be instrumental in the execution of apoptosis following caspase activation. Multiple alternatively spliced variants have been found for this gene. DNA and protein sequences of human p21 were previously reported, see GenBank Nos. NC_000006.11, NT_007592.15, NC_018917.2 and Uniprot No. P38936, each of which is incorporated herein by reference in its entirety for all purposes. Such sequences can be utilized to design procedures for detection and analysis of the level of p21 activity by ways known to one skilled in the art.

Some other components of the CDX2-KLF4 signaling pathway are H3K4 demethylase Jarid1b (KDM5B, a.k.a. Plu-1 or Rbp2-h1), microRNA miR-2909, tumor suppressor p53 (a.k.a TP53 or tumor protein (EC:2.7.1.37)), cysteine-aspartic acid protease Caspase-3, Annexin V, B-cell CLL/Lymphoma 2 (BCL2), B-cell CLL/Lymphoma 3 (BCL3), BCL2-associated X protein (BAX), bone morphogenetic proteins (BMPs), Wnt (a.k.a. murine int-1), hepatocyte nuclear factor 4α (HNF4α), fibroblast growth factors (Fgf), homeobox (Hox), transcription factor SP1, transcription factor MYC, cyclin D1 (CCND1, a.k.a. PRAD1), and apoptosis-antagonizing transcription factor (AATF).

An active agent of the present invention can modulate the activity of one or more component in the CDX2-KLF4 signaling pathway. In some embodiments, the active agent is a small molecule. In some embodiments, the active agent is a polypeptide, such as an antibody. In some embodiments, the active agent is a polynucleotide, such as siRNA.

In some embodiments, the active agent modulates the gene copy number of a component in the CDX2-KLF4 signaling pathway. In some embodiments, the active agent can increase or decrease the gene copy number by 0.5×, 1.0×, 1.5×, 2×, 3×, 4×, 5×, 6×, 7×, 8×, 9×, 10×, 100×, 1000×, 10000× or more when compared to the gene copy number before treatment.

In some embodiments, the active agent modulates the mRNA abundance of a component in the CDX2-KLF4 signaling pathway. In some embodiments, the active agent can increase or decrease the mRNA abundance by 0.5×, 1.0×, 1.5×, 2×, 3×, 4×, 5×, 6×, 7×, 8×, 9×, 10×, 100×, 1000×, 10000× or more when compared to the mRNA abundance before treatment.

In some embodiments, the active agent modulates the protein level of a component in the CDX2-KLF4 signaling pathway. In some embodiments, the active agent can increase or decrease the protein level by 0.5×, 1.0×, 1.5×, 2×, 3×, 4×, 5×, 6×, 7×, 8×, 9×, 10×, 100×, 1000×, 10000× or more when compared to the protein level before treatment.

In some embodiments, the active agent modulates the mRNA and/or protein stability of a component in the CDX2-KLF4 signaling pathway. In some embodiments, the active agent can increase or decrease the stability when compared to the stability before treatment.

In some embodiments, the active agent modulates the enzymatic activity of a component in the CDX2-KLF4 signaling pathway. In some embodiments, the active agent can increase or decrease the enzymatic activity when compared to the stability before treatment.

The activity of a component in the CDX2-KLF4 signaling pathway can be determined by any suitable methods known to one skilled in the art. In some embodiments, a biological sample is taken from a subject and analyzed. In some embodiments, the biological sample is then assayed for activity of a component in the CDX2-KLF4 signaling pathway, such as gene amplification number, RNA, mRNA, cDNA, cRNA, protein, etc.

In some embodiments, mRNA from a biological sample is directly used in determining the level of activity. In some embodiments, the level is determined by hybridization. In some embodiments, the RNA is transformed into cDNA (complementary DNA) copy using methods known in the art. In some particular embodiments, the cDNA is labeled with a fluorescent label or other detectable label. The cDNA is then hybridized to a substrate containing a plurality of probes of interest. A probe of interest typically hybridizes under stringent hybridization conditions to at least one DNA sequence of a gene signature. In certain embodiments, the plurality of probes are capable of hybridizing to the sequences derived from the gene biomarkers under the hybridization conditions. In some embodiments, the conditions comprise using 6×SSC (0.9 M NaCl, 0.09 M sodium citrate, pH 7.4) at 65° C. The probes may comprise nucleic acids. The term "nucleic acid" encompasses known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, peptide-nucleic acids (PNAs). Methods for detecting can include but are not limited to RT-PCR, northern blot analyses, gene expression analyses, microarray analyses, gene expression chip analyses, hybridization techniques (including FISH), expression beadchip arrays, and chromatography as well as any other techniques known in the art. Methods for detecting DNA can include but are not limited to PCR, real-time PCR, digital PCR, hybridization (including FISH), microarray analyses, SNP detection assays, SNP genotyping assays and chromatography as well as any other techniques known in the art.

In some embodiments, the protein expression level is used in determining the level of activity. The protein expression level of a component in the CDX2-KLF4 signaling pathway can be determined by any suitable methods known to one skilled in the art. Any suitable methods of protein detection, quantization and comparison can be used, such as those described in Tschesche (Methods in Protein Biochemistry, ISBN Walter de Gruyter, 2011, ISBN 3110252368, 9783110252361), Goluch et al. (Chip-based detection of protein cancer markers, ProQuest, 2007, ISBN 0549463453, 9780549463450), Speicher (Proteome Analysis: Interpreting the Genome, Elsevier, 2004, ISBN 0080515304, 9780080515304), Albala et al. (Protein Arrays, Biochips and Proteomics, CRC Press, 2003, ISBN 0203911121, 9780203911129), Walker (The Protein Protocols Handbook, Springer, 2002, ISBN 0896039404, 9780896039407), Fung (Protein Arrays: Methods and Protocols, Springer, 2004, ISBN 1592597599, 9781592597598), and Bienvenut (Acceleration and Improvement of Protein Identification by Mass Spectrometry, Springer, 2005, ISBN 1402033184, 9781402033186), each of which is incorporated by reference in its entirety for all purposes. In some embodiments, the protein expression level of biomarkers are detected and measured by immunohistochemistry (IHC), western blot, protein immunestaining, protein immuneprecipitation, immuneeletrophoresis, immunoblotting, BCA assay, spectrophotometry, mass spectrometry or enzyme assay, or combinations thereof. For additional methods related to detection, quantitation and comparison of biomarker levels, see, e.g., Current Protocols in Molecular Biology, Ed. Ausubel, Frederick M. (2010); Current Protocols in Protein Science Last, Ed. Coligan, John E., et al. (2010); Current Protocols in Nucleic Acid Chemistry, Ed. Egli, Martin (2010); Current Protocols in Bioinformatics, Ed. Baxevanis, Andreas D. (2010); and Molecular Cloning: A Laboratory Manual, Third Edition, Sambrook, Joseph (2001), all of which are incorporated herein by reference in their entirety.

In some embodiments, antibody of a component in the CDX2-KLF4 signaling pathway can be used as an active agent. In some embodiments, antibody of a component in the CDX2-KLF4 signaling pathway that negatively control KLF4 and/or p21, or a component in the CDX2-KLF4 signaling pathway that are negatively controlled by KLF4 and/or p21 can be used as an active agent. For example, antibodies of CDX2 can be used to treat the cancers of the present invention.

In some embodiments, antibody of a component in the CDX2-KLF4 signaling pathway can be used to detect the protein level of the component. In some embodiments, a kit for detection is used. Such antibodies and kits are available from EMD Millipore, OriGene Custom Assay Services, R&D Systems for biochemical assays, GenScript Custom Assay Services, Enzo Life Sciences for kits & assays, Cloud-Clone Corp. ELISAs, or Cloud-Clone Corp. CLIAs. The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')2, scFv, dsFv, ds-scFv, dimers, minibodies, diabodies, and multimers thereof and biospecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, biospecific antibody fragments and other fragments can also be synthesized by recombinant techniques.

Immunoassays carried out in accordance with the present invention may be homogeneous assays or heterogeneous assays. In a homogeneous assay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include, but are not limited to oligonucleotides, immunoblotting, immunoprecipitation, immunofluorescence methods, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. Nos. 4,727,022, 4,659,678, 4,376,110, 4,275,149, 4,233,402, 4,230,767, each of which is herein incorporated by reference in its entirety for all purposes.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding.

Antibodies as described herein may likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51).

In some embodiments, detection reagents can be immobilized on a solid matrix such as a porous strip to form at least one detection site. In some embodiments, polynucleotide or polypeptide arrays or microarrays containing a plurality of detection agents that hybridize to nucleotide or polypeptide of the biomarkers are utilized. Alternatively, the substrate array can be on, e.g., a solid substrate, e.g., a "chip" as described in U.S. Pat. No. 5,744,305. Alternatively, the substrate array can be a solution array.

Non-limiting examples for compositions and methods for detecting the components in the CDX2-KLF4 signaling pathway are described in U.S. Pat. Nos. 4,762,706, 5,081, 230, 5,300,631, 5,443,956, 7,695,926, 7,785,817, 7,479,376, 7,364,868 and U.S. Patent Publication Nos. 20050196793, 20110281277, 20120251509, 20050186642, 20140011279, 20110171221, 20040235073, 20130011411, and 20130034862, each of which is incorporated herein by reference in its entirety for all purposes.

Anti-Caner Compositions

Anti-cancer compositions that can be utilized in the present invention comprise at least one active agent. In some embodiments, the active agent can modulate the activity of the CDX2-KLF4 signaling pathway. As used herein, the term "modulate" refers to that the compositions can increase, decrease, eliminate, enhance, delay, reduce, or block the activity of a component in the CDX2-KLF4 signaling pathway. In some embodiments, the compounds can decrease the CDX2 activity, and/or increase the KLF4 activity in a human subject. In some embodiments, the compounds can increase or decrease the activity of one or more upstream or downstream components in the signaling pathway. In some embodiments, the compounds can increase the activity of one or more downstream components that are positively regulated by KLF4 (e.g., p21), or decrease the activity of one or more downstream components in the signaling pathway that are negatively regulated by KLF4 (e.g., SP1). In some embodiments, the compounds can decrease the activity of one or more downstream components that are positively regulated by CDX2, or increase the activity of one or more downstream components in the signaling pathway that are negatively regulated by CDX2.

Without wishing to be bound by any particular theory, the anti-cancer agents of the present invention can act through one or more mechanisms. Such mechanisms include, but are not limited to: (1) inhibition of CDX2 activity; (2) induction of KLF4 activity; (3) induction of p21 CDK inhibitor; (4) induction of G1/S Cell cycle arrest; (5) induction of Caspase 3 enzyme; and (6) induction of apoptosis.

The active agents can be chemical compounds or compositions, biological molecules, or combinations thereof. In some embodiments, the active agents are small molecules. As used herein, the term "small molecule" refers to a molecule having a molecular weight of less than 500 MW, wherein the drug is a non-peptidyl or peptide agent. In some embodiments, the active agents are antibodies. In some embodiments, the active agents are antibodies. In some embodiments, the active agents are polynucleotides, such as siRNA.

In some embodiments, the active agents contain one or more entities that can inhibit or decrease the activity of CDX2, e.g., at DNA, RNA, protein level, or combinations thereof.

In some embodiments, the active agents contain one or more antibodies that can reduce, inhibit or delay the activity of a component in the CDX2-KLF4 signaling pathway that negatively regulates KLF4, or negatively regulated by KLF4. In some embodiments, the component can be CDX2, p53, p21, Caspase-3, Annexin V, BAX, BCL2, BCL3, BMP, Wnt, HNF4α, Fgf, Hox, SP1, MYC, CCND1, or AATF. In some embodiments, the active agents are antibodies. In some embodiments, the active agents are siRNA. For example, the anti-CDX2 agent is an anti-CDX2 antibody. According to the present invention, an anti-CDX2 antibody at least comprises one or more anti-CDX2 CDRs.

For example, antisense RNA, ribozyme, dsRNAi, RNA interference (RNAi) technologies can be used in the present invention to target RNA transcripts of one or more component in the CDX2-KLF4 signaling pathway. Antisense RNA technology involves expressing in, or introducing into, a cell an RNA molecule (or RNA derivative) that is complementary to, or antisense to, sequences found in a particular mRNA in a cell. By associating with the mRNA, the antisense RNA can inhibit translation of the encoded gene product. For example, the anti-CDX2 agents can be small interference RNA molecules, such as those disclosed by Wang et al. ("siRNA targeting of Cdx2 inhibits growth of human gastric cancer MGC-803 cells", *World J Gastroenterol*. Apr. 28, 2012; 18(16): 1903-1914.)

RNA interference (RNAi) is the process of sequence-specific, post-transcriptional gene silencing or transcriptional gene silencing in animals and plants, initiated by double-stranded RNA (dsRNA) that is homologous in sequence to the silenced gene. The RNAi technique is discussed, for example, in Elibashir, et al., Methods Enzymol. 26:199 (2002); McManus & Sharp, Nature Rev. Genetics 3:737 (2002); PCT application WO 01/75164; Martinez et al., Cell 110:563 (2002); Elbashir et al., supra; Lagos-Quintana et al., Curr. Biol. 12:735 (2002); Tuschl et al., Nature Biotechnol. 20:446 (2002); Tuschl, Chembiochem. 2:239 (2001); Harborth et al., J. Cell Sci. 114:4557 (2001); et al., EMBO J. 20:6877 (2001); Lagos-Quintana et al., Science 294:8538 (2001); Hutvagner et al., loc cit, 834; Elbashir et al., Nature 411:494 (2001).

The term "dsRNA" or "dsRNA molecule" or "double-strand RNA effector molecule" refers to an at least partially double-strand ribonucleic acid molecule containing a region of at least about 19 or more nucleotides that are in a double-strand conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA). In various embodiments, the dsRNA consists entirely of ribonucleotides or consists of a mixture of ribonucleotides and deoxynucleotides, such as RNA/DNA hybrids. The dsRNA may be a single molecule with regions of self-complementarity such that nucleotides in one segment of the molecule base pair with nucleotides in another segment of the molecule. In one aspect, the regions of self-complementarity are linked by a region of at least about 3-4 nucleotides, or about 5, 6, 7, 9 to 15 nucleotides or more, which lacks complementarity to another part of the molecule and thus remains single-stranded (i.e., the "loop region"). Such a molecule will assume a partially double-stranded stem-loop structure, optionally, with short single stranded 5' and/or 3' ends. In one aspect the regions of self-complementarity of the hairpin dsRNA or the double-stranded region of a duplex dsRNA will comprise an Effector Sequence and an Effector Complement (e.g., linked by a single-stranded loop region in a hairpin dsRNA). The Effector Sequence or Effector Strand is that strand of the double-stranded region or duplex which is incorporated in or associates with RISC. In one aspect the double-stranded RNA effector molecule will comprise an at least 19 contiguous nucleotide effector sequence, preferably 19 to 29, 19 to 27, or 19 to 21 nucleotides, which is a reverse complement to the RNA of a target gene, or an opposite strand replication intermediate, or the anti-genomic plus strand or non-mRNA plus strand sequences of the target gene.

In some embodiments, the dsRNA effector molecule of the invention is a "hairpin dsRNA", a "dsRNA hairpin", "short-hairpin RNA" or "shRNA", i.e., an RNA molecule of less than approximately 400 to 500 nucleotides (nt), or less than 100 to 200 nt, in which at least one stretch of at least 15 to 100 nucleotides (e.g., 17 to 50 nt, 19 to 29 nt) is based paired with a complementary sequence located on the same RNA molecule (single RNA strand), and where said sequence and complementary sequence are separated by an unpaired region of at least about 4 to 7 nucleotides (or about 9 to about 15 nt, about 15 to about 100 nt, about 100 to about 1000 nt) which forms a single-stranded loop above the stem structure created by the two regions of base complementarity. The shRNA molecules comprise at least one stem-loop structure comprising a double-stranded stem region of about 17 to about 100 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, or about 9 to about 15 nucleotides, about 15 to about 100 nt, about 100 to about 1000 nt, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence.

In some embodiments, the active agents contain one or more entities that can increase the activity of KLF4, or increase the activity of an entity in the CDX2-KLF4 signaling pathway that is positively regulated by KLF4, or increase the activity of an entity that can positively regulate KLF4, e.g., at DNA, RNA, protein level, or combinations thereof. In some embodiments, the active agent of the present invention is a 2-indolyl imidazo[4,5-d]phenanthroline derivative, such as those described in U.S. Pat. No. 8,148,392 or U.S. Patent Publication No. 2007/0123553A1, each of which is herein incorporated by reference in its entirety for all purposes.

In some embodiments, the compound has the structure of formula I, or a salt thereof:

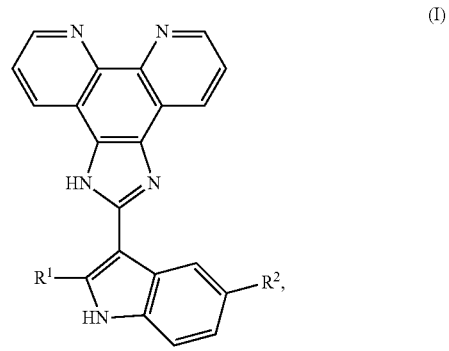

(I)

Wherein R1 is C1-C4 alkyl; and R2 is halogen. In some embodiments, $R^1$ is methyl, isopropyl, or t-butyl.

In some embodiments, the compound has the structure of formula II, or a salt thereof:

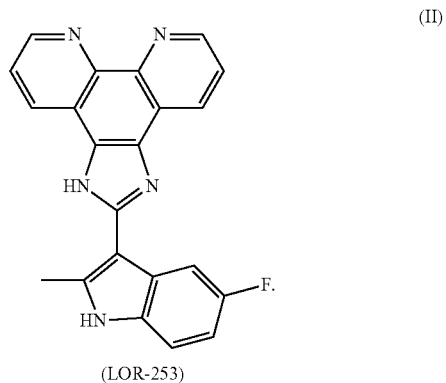 [SMILES: Cc1[nH]c2ccc(F)cc2c1-c1nc2c3cccnc3c3ncccc3c2[nH]1]

(II)

(LOR-253)

In some embodiments, the compound has the structural formula (III), or a salt thereof:

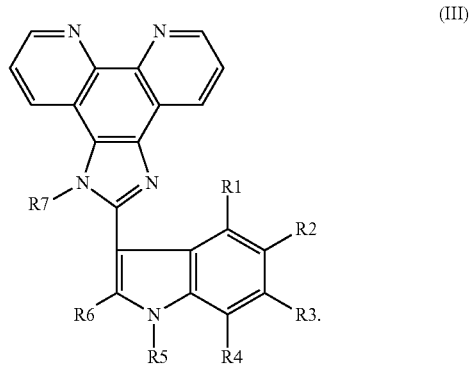

(III)

wherein: R1, R2, R3, R4, R6 and R7 are independently selected from hydrogen, halogen, hydroxyl, thiol, lower alkyl, substituted lower alkyl, lower alkenyl, substituted lower alkenyl, lower alkynyl, substituted lower alkynyl, alkoxy, alkylthio, acyl, aryloxy, amino, amido, carboxyl, aryl, substituted aryl, heterocycle, substituted heterocycle, heteroalkyl, substituted heteroalkyl, heteroaryl, substituted heteroaryl, cycloalkyl, substituted cycloalkyl, nitro, or cyano or —S(O)1-2R wherein R is alkyl, substituted alkyl, aryl, substituted aryl, heterocycle, heteroaryl, substituted heterocycle, or substituted heteroaryl; and wherein R5 is H, alkyl, substituted alkyl, alkenyl, substituted alkenyl, alkynyl, substituted alkynyl, aryl, substituted aryl, heteroaryl, substituted heteroaryl, acyl, —CH2-aryl, —CH2-heteroaryl.

In some embodiments, R1, R2, R3, R4 are independently hydrogen; halogen; C1-C4 alkyl; C1-C4 alkoxy; or C6-C14 aryl; R5 is hydrogen; C1-C4 alkyl; C1-C4 alkyl substituted with C6-C14 aryl; or C4-C6 cycloalkyl; R6 is hydrogen; halogen; C1-C4 alkyl; C1-C4 alkyl substituted with C5-C6 heterocycloalkyl wherein the heteroatom is N; C6-C14 aryl; C6-C14 aryl substituted with C1-C4 alkyl or halo; C5-C6 cycloalkyl; C5-C6 heterocycloalkyl; or polycycloalkyl. In some other embodiments, R1, R2, R3, R4 are independently hydrogen; halogen; C1-C4 alkyl; C1-C4 alkoxy; or phenyl; R5 is hydrogen; C1-C4 alkyl; C1-C4 alkyl substituted with phenyl; or cyclopentyl; R6 is hydrogen; halogen; C1-C4 alkyl; C1-C4 alkyl substituted with C5-C6 heterocycloalkyl wherein the heteroatom is N; phenyl; phenyl substituted with C1-C4 alkyl or halo; C5-C6 cycloalkyl; C5-C6 heterocycloalkyl; or adamantane; and R7 is H.

In some embodiments, said compound has a formula selected from the group consisting of

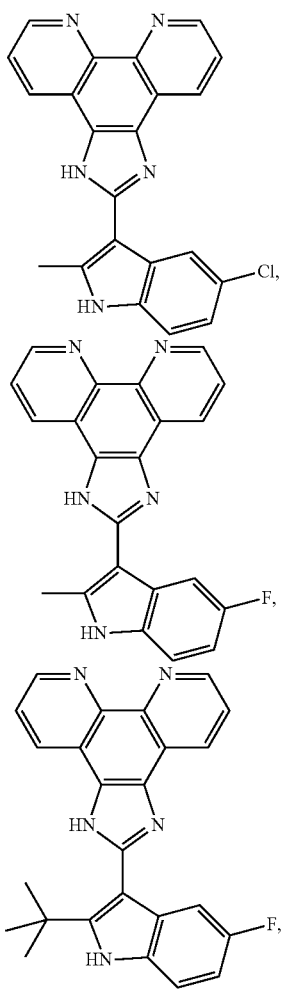

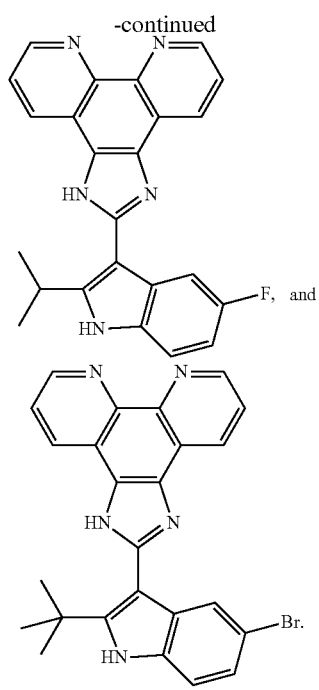

The active agents of the present invention are typically formulated prior to administration. The present invention thus provides pharmaceutical compositions comprising one or more active agents of the present invention. In some embodiments, the pharmaceutical compositions comprise a pharmaceutically acceptable carrier, diluent, or excipient. The pharmaceutical compositions are prepared by known procedures using well-known and readily available ingredients.

Active agents of the present invention or pharmaceutical compositions comprising the active agents may be administered via any suitable methods, including but not limited to, orally, topically, parenterally, by inhalation or spray, or rectally in dosage unit formulations. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally. In some embodiments, the dosage unit formulations contain conventional non-toxic pharmaceutically acceptable carriers, adjuvants and vehicles. In the usual course of therapy, the active agent is incorporated into an acceptable vehicle to form a composition for topical administration to the affected area, such as hydrophobic or hydrophilic creams or lotions, or into a form suitable for oral, rectal or parenteral administration, such as syrups, elixirs, tablets, troches, lozenges, hard or soft capsules, pills, suppositories, oily or aqueous suspensions, dispersible powders or granules, emulsions, injectables, or solutions. The term parenteral as used herein includes, but are not limited to, subcutaneous injections, intradermal, intra-articular, intravenous, intramuscular, intravascular, intrasternal, intrathecal injection or infusion techniques.

The present invention also provides for pharmaceutical compositions comprising one or more of the active agents of the present invention and a vehicle, such as an artificial membrane vesicle (including a liposome, lipid micelle and the like), microparticle or microcapsule.

Compositions intended for oral use may be prepared in either solid or fluid unit dosage forms. Fluid unit dosage form can be prepared according to procedures known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Solid formulations such as tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Soft gelatin capsules are prepared by machine encapsulation of a slurry of the compound with an acceptable vegetable oil, light liquid petrolatum or other inert oil.

Aqueous suspensions contain active materials in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-deca-ethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents, one or more flavouring agents or one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Adjuvants such as local anaesthetics, preservatives and buffering agents can also be included in the injectable solution or suspension.

In some embodiments, the delivery systems suitable include time-release, delayed release, sustained release, or controlled release delivery systems. In some embodiments, a composition of the present invention can be delivered in a controlled release system, such as sustained-release matrices. Non-limiting examples of sustained-release matrices include polyesters, hydrogels (e.g., poly(2-hydroxyethyl-methacrylate) as described by Langer et al., 1981, J. Biomed. Mater. Res., 15:167-277 and Langer, 1982, Chem. Tech., 12:98-105), or poly(vinylalcohol)], polylactides (U.S. Pat. No. 3,773,919; EP 58,481), copolymers of L-glutamic acid and gamma ethyl-L-glutamate (Sidman et al., 1983, Biopolymers, 22:547-556), non-degradable ethylene-vinyl acetate (Langer et al., supra), degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid (EP 133,988). In some embodiments, the composition may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, for example liver, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

In some embodiments, the release of the composition occurs in bursts. Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme.

In some embodiments, the release of the composition is gradual/continuous. Examples of systems in which release of the inhibitor is gradual and continuous include, e.g., erosional systems in which the composition is contained in a form within a matrix and effusional systems in which the composition penneates at a controlled rate, e.g., through a polymer. Such sustained release systems can be e.g., in the form of pellets, or capsules.

Other embodiments of the compositions administered according to the invention incorporate particulate forms, protective coatings, protease inhibitors or permeation enhancers for various routes of administration, such as parenteral, pulmonary, nasal and oral.

The pharmaceutical compositions of the present invention may be administered, together or separately, in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, Pa. (2000).

The pharmaceutical compositions of the present invention may be administered to a subject by a variety of routes depending on the cancer to be treated, for example, the compositions may be administered orally, topically, parenterally, by inhalation or spray, or rectally in dosage unit formulations. In one embodiment, the compounds are administered systemically to a subject, for example, by bolus injection or infusion into a subject's bloodstream or by oral administration. When used in conjunction with one or more known chemotherapeutic agents, the compounds can be administered prior to, or after, administration of the chemotherapeutic agents, or they can be administered concomitantly. The one or more chemotherapeutic may also be administered systemically, for example, by bolus injection, infusion, or oral administration.

The pharmaceutical compositions of the present invention may be used as part of a neo-adjuvant therapy (to primary therapy), or as part of an adjuvant therapy regimen. The present invention contemplates the use of the pharmaceutical compositions of the present invention at various stages in tumor development and progression, including, but not limited to, in the treatment of advanced and/or aggressive neoplasias (i.e. overt disease in a subject that is not amenable to cure by local modalities of treatment, such as surgery or radiotherapy), metastatic disease, locally advanced disease and/or refractory tumors (i.e. a cancer or tumor that has not responded to treatment). As used herein, the term "primary therapy" refers to a first line of treatment upon the initial diagnosis of cancer in a subject. Exemplary primary therapies may involve surgery, a wide range of chemotherapies and radiotherapy. "Adjuvant therapy" refers to a therapy that follows a primary therapy and that is administered to subjects at risk of relapsing. Adjuvant systemic therapy is usually begun soon after primary therapy to delay recurrence, prolong survival or cure a subject.

The pharmaceutical compositions of the present invention can be used alone or in combination with one or more other anti-cancer agents, such as chemotherapeutic agents as part of a primary therapy or an adjuvant therapy. Combinations of the pharmaceutical compositions of the present invention and standard chemotherapeutics may act to improve the efficacy of the chemotherapeutic and, therefore, can be used to improve standard cancer therapies. This application can be important in the treatment of drug-resistant cancers which are not responsive to standard treatment. Drug-resistant cancers can arise, for example, from heterogeneity of tumor cell populations, alterations in response to chemotherapy and increased malignant potential. Such changes are often more pronounced at advanced stages of disease.

The pharmaceutical compositions of the present invention can be used alone or in combination with radiation therapeutic. In some embodiments, the radiation therapeutic is administered at a dosage of about 40 Gy to about 80 Gy. In some embodiments the dosage is about 50 Gy to about 70 Gy, in some embodiments, the dosage is about 50 Gy to about 65 Gy. In some embodiments, the radiation therapy is administered at a dosage of about 50 Gy, about 55 Gy, about 60 Gy or about 65 Gy.

The dosage to be administered is not subject to defined limits, but it will usually be an effective amount. It will usually be the equivalent, on a molar basis of the pharmacologically active free form produced from a dosage formulation upon the metabolic release of the active free drug to achieve its desired pharmacological and physiological effects. The compositions may be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the active agents are compounds having the structure of formulas described herein. However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above dosage range is given by way of example only and is not intended to limit the scope of the invention in any way. In some instances dosage levels below the lower limit of the aforesaid range may be more than adequate, while in other cases still larger doses may be employed without causing harmful side effects, for example, by first dividing the larger dose into several smaller doses for administration throughout the day.

Dosages for a particular individual can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to an individual is sufficient to effect a beneficial therapeutic response in the individual over time, or, e.g., to reduce symptoms, or other appropriate activity, depending on the application. The dose is determined by the efficacy of the particular formulation, and the activity, stability or serum half-life of the composition and the condition of the individual, as well as the body weight or surface area of the individual to be treated. The size of the dose is also determined by the existence, nature, and extent of any adverse side-effects that accompany the administration of a particular vector, formulation, or the like in a particular individual.

In some embodiments, dosage unit for a compound of the present invention can be about 0.001 mg, about 0.002 mg, about 0.003 mg, about 0.004 mg, about 0.005 mg, about 0.006 mg, about 0.007 mg, about 0.008 mg, about 0.009 mg, about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 30 mg, about 35 mg, about 40 mg, about 45 mg, about 50 mg, about 60 mg, about 70 mg, about 80 mg, about 90 mg, about 100 mg, about 200 mg, about 300 mg, about 400 mg, about 500 mg or more.

In some embodiments, daily dosages of the compounds of the present invention will typically be about 0.001 mg/kg of body weight, about 0.002 mg/kg of body weight, about 0.003 mg/kg of body weight, about 0.004 mg/kg of body weight, about 0.005 mg/kg of body weight, about 0.006 mg/kg of body weight, about 0.007 mg/kg of body weight, about 0.008 mg/kg of body weight, about 0.009 mg/kg of body weight, about 0.01 mg/kg of body weight, about 0.02 mg/kg of body weight, about 0.03 mg/kg of body weight, about 0.04 mg/kg of body weight, about 0.05 mg/kg of body weight, about 0.06 mg/kg of body weight, about 0.07 mg/kg of body weight, about 0.08 mg/kg of body weight, about 0.09 mg/kg of body weight, about 0.1 mg/kg of body weight, about 0.2 mg/kg of body weight, about 0.3 mg/kg of body weight, about 0.4 mg/kg of body weight, about 0.5 mg/kg of body weight, about 0.6 mg/kg of body weight, about 0.7 mg/kg of body weight, about 0.8 mg/kg of body weight, about 0.9 mg/kg of body weight, about 1 mg/kg of body weight, about 2 mg/kg of body weight, about 3 mg/kg of body weight, about 4 mg/kg of body weight, about 5 mg/kg of body weight, about 6 mg/kg of body weight, about 7 mg/kg of body weight, about 8 mg/kg of body weight, about 9 mg/kg of body weight, about 10 mg/kg of body weight, about 15 mg/kg of body weight, about 20 mg/kg of body weight, about 30 mg/kg of body weight, about 35 mg/kg of body weight, about 40 mg/kg of body weight, about 45 mg/kg of body weight, about 50 mg/kg of body weight, about 60 mg/kg of body weight, about 70 mg/kg of body weight, about 80 mg/kg of body weight, about 90 mg/kg of body weight, about 100 mg/kg of body weight, about 200 mg/kg of body weight, about 300 mg/kg of body weight, about 400 mg/kg of body weight, about 500 mg/kg of body weight or more. Either single or divided dose can be used.

In some embodiments, the dosage form of the present invention is effective to provide a maximum total plasma concentration in said human subject of no more than about 1 pg/mL, about 5 pg/mL, about 10 pg/mL, about 50 pg/mL, about 100 pg/mL, about 500 pg/mL, about 1 ng/mL, about 5 ng/mL, about 10 ng/mL, about 50 ng/mL, about 100 ng/mL, about 500 ng/mL, about 1 µg/mL, about 5 µg/mL, about 10 µg/mL, about 50 µg/mL, about 100 µg/mL, about 500 µg/mL, about 1 mg/mL or more of free base equivalent of the compound.

In a further aspect of any of dosage forms as described herein, the dosage form is an oral dosage form. In a still further aspect, the dosage form is an intravenous dosage form. The dosage form is suitable for administration to a human subject particularly for use in the treatment of any of the disorders described herein. In some embodiments, the dosage form is a subcutaneous dosage form.

Pharmaceutical compositions comprising one or more compounds described herein in combination with one or more other anti-cancer agents can also be used. Such conjoint treatment may be achieved by way of the simultaneous, sequential or separate dosing of the individual components of the treatment.

In some embodiments, the anti-cancer agents are chemotherapeutics. In some embodiments, the chemotherapeutics are selected from alkylating agents, anti-metabolites, anti-microtubule agents, Topoisomerase inhibitors, and Cytotoxic antibiotics. Examples of chemotherapeutic agents include, but are not limited to, paclitaxel (Taxol®), docetaxel (Taxotere®), cisplatin, carboplatin (Paraplatin®), gemcitabine hydrochloride (Gemzar®), doxorubicin, etoposide (Etopophos®, Vepesid®), pemetrexed (Alimta®), topotecan (Hycamtin®), vinblastine (Velbe®), Vindesine (Eldisine®), vinorelbine (Navelbine®), ifosfamide (Mitoxana®), Mitomycin, and gemcitabine. These agents may be given in combination, for example, vinorelbine and cisplatin or carboplatin; gemcitabine with cisplatin or carboplatin or paclitaxel; MIC (mitomycin, ifosfamide and cisplatin); MVP (mitomycin, vinblastine and cisplatin); and EC (etoposide and carboplatin). Examples of useful chemotherapeutic drugs include, but are not limited to, hydroxyurea, busulphan, cisplatin, carboplatin, chlorambucil, melphalan, cyclophosphamide, Ifosfamide, danorubicin, doxorubicin, epirubicin, mitoxantrone, vincristine, vinblastine, Navelbine® (vinorelbine), etoposide, teniposide, paclitaxel, docetaxel, gemcitabine, cytosine, arabinoside, bleomycin, neocarcinostatin, suramin, taxol, mitomycin C and the like.

As used herein, the term "alkylating agents" refers to agents that have the ability to alhylate molecules in a subject, including proteins, RNA and DNA. Non-limiting examples of alkylating agents include nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Cisplatin and derivatives include cisplatin, carboplatin and oxaliplatin. They impair cell function by forming covalent bonds with the amino, carboxyl, sulfhydryl, and phosphate groups in biologically important molecules.[20] Non-classical alkylating agents include procarbazine and hexamethylmelamine.

As used herein, the term "anti-metabolites" refers to molecule that impedes DNA, RNA, or protein synthesis. In some embodiments, anti-metabolites resemble either nucleobases or nucleosides (a nucleotide without the phosphate group), but have altered chemical groups. These drugs exert their effect by either blocking the enzymes required for DNA synthesis or becoming incorporated into DNA or RNA. By inhibiting the enzymes involved in DNA synthesis, they prevent mitosis because the DNA cannot duplicate itself. Also, after misincorporation of the molecules into DNA, DNA damage can occur and programmed cell death (apoptosis) is induced. In some embodiments, the anti-metabolites are anti-folates, fluoropyrimidines, deoxynucleoside analogues and thiopurines. In some embodiments, the anti-metabolites are selected from methotrexate, pemetrexed, fluorouracil, capecitabine, cytarabine, gemcitabine, decitabine, Vidaza, fludarabine, nelarabine, cladribine, clofarabine, pentostatin, thioguanine and mercaptopurine.

As used herein, the term "anti-microtubule agents" refers to chemicals that block cell division by preventing microtubule function. Representative examples of such agents include taxanes (e.g., paclitaxel (discussed in more detail below) and docetaxel) (Schiff et al., Nature 277: 665-667, 1979; Long and Fairchild, Cancer Research 54: 4355-4361, 1994; Ringel and Horwitz, J. Natl. Cancer Inst. 83(4): 288-291, 1991; Pazdur et al, Cancer Treat. Rev. 19(4): 351-386, 1993), campothecin, mitoxantrone, eleutherobin (e.g., U.S. Pat. No. 5,473,057), sarcodictyins (including sarcodictyin A), epothilones A and B (Bollag et al., Cancer Research 55: 2325-2333, 1995), discodermolide (ter Haar et al., Biochemistry 35: 243-250, 1996), deuterium oxide (D2O) (James and Lefebvre, Genetics 130(2): 305-314, 1992; Sollott et al., J. Clin. Invest. 95: 1869-1876, 1995), hexylene glycol (2-methyl-2,4-pentanediol) (Oka et al., Cell Struct. Funct. 16(2): 125-134, 1991), tubercidin (7-deazaadenosine) (Mooberry et al., Cancer Lett. 96(2): 261-266, 1995), LY290181 (2-amino-4-(3-pyridyl)-4H-naphtho(1,2-b)pyran-3-cardonitrile) (Panda et al., J. Biol. Chem. 272(12): 7681-7687, 1997; Wood et al., Mol. Pharmacol. 52(3): 437-444, 1997), aluminum fluoride (Song et al., J. Cell. Sci. Suppl. 14: 147-150, 1991), ethylene glycol bis-(succinimidylsuccinate) (Caplow and Shanks, J. Biol. Chem. 265(15): 8935-8941, 1990), glycine ethyl ester (Mejillano et al., Biochemistry 31(13): 3478-3483, 1992), nocodazole (Ding et al., J. Exp. Med 171(3): 715-727, 1990; Dotti et al., J. Cell Sci. Suppl. 15: 75-84, 1991; Oka et al., Cell Struct. Funct. 16(2): 125-134, 1991; Weimer et al., J. Cell. Biol. 136(1): 71-80, 1997), cytochalasin B (Illinger et al., Biol. Cell 73(2-3): 131-138, 1991), colchicine and CI 980 (Allen et al., Am. J. Physiol. 261(4 Pt. 1): L315-L321, 1991; Ding et al., J. Exp. Med. 171(3): 715-727, 1990; Gonzalez et al., Exp. Cell. Res. 192(1): 10-15, 1991; Stargell et al., Mol. Cell. Biol. 12(4): 1443-1450, 1992; Garcia et al., Antican. Drugs 6(4): 533-544, 1995), colcemid (Barlow et al., Cell. Motil. Cytoskeleton 19(1): 9-17, 1991; Meschini et al., J. Microsc. 176(Pt. 3): 204-210, 1994; Oka et al., Cell Struct. Funct. 16(2): 125-134, 1991), podophyllotoxin (Ding et al., J. Exp. Med. 171(3): 715-727, 1990), benomyl (Hardwick et al., J. Cell. Biol. 131(3): 709-720, 1995; Shero et al., Genes Dev. 5(4): 549-560, 1991), oryzalin (Stargell et al., Mol. Cell. Biol. 12(4): 1443-1450, 1992), majusculamide C (Moore, J. Ind. Microbiol. 16(2): 134-143, 1996), demecolcine (Van Dolah and Ramsdell, J. Cell. Physiol. 166(1): 49-56, 1996; Wiemer et al., J. Cell. Biol. 136(1): 71-80, 1997), methyl-2-benzimidazolecarbamate (MBC) (Brown et al., J. Cell. Biol. 123(2): 387-403, 1993), LY195448 (Barlow & Cabral, Cell Motil. Cytoskel. 19: 9-17, 1991), subtilisin (Saoudi et al., J. Cell Sci. 108: 357-367, 1995), 1069C85 (Raynaud et al., Cancer Chemother Pharmacol. 35: 169-173, 1994), steganacin (Hamel, Med. Res. Rev. 16(2): 207-231, 1996), combretastatins (Hamel, Med Res. Rev. 16(2): 207-231, 1996), curacins (Hamel, Med. Res. Rev. 16(2): 207-231, 1996), estradiol (Aizu-Yokata et al., Carcinogen. 15(9): 1875-1879, 1994), 2-methoxyestradiol (Hamel, Med. Res. Rev. 16(2): 207-231, 1996), flavanols (Hamel, Med. Res. Rev. 16(2): 207-231, 1996), rotenone (Hamel, Med Res. Rev. 16(2): 207-231, 1996), griseofulvin (Hamel, Med Res. Rev. 16(2): 207-231, 1996), vinca alkaloids, including vinblastine and vincristine (Ding et al., J. Exp. Med 171(3): 715-727, 1990; Dirk et al., Neurochem. Res. 15(11): 1135-1139, 1990; Hamel, Med. Res. Rev. 16(2): 207-231, 1996; Illinger et al., Biol. Cell 73(2-3): 131-138, 1991; Wiemer et al., J. Cell. Biol. 136(1): 71-80, 1997), maytansinoids and ansamitocins (Hamel, Med Res. Rev. 16(2): 207-231, 1996), rhizoxin (Hamel, Med. Res. Rev. 16(2): 207-231, 1996), phomopsin A (Hamel, Med. Res. Rev. 16(2): 207-231, 1996), ustiloxins (Hamel, Med. Res. Rev. 16(2): 207-231, 1996), dolastatin 10 (Hamel, Med Res. Rev. 16(2): 207-231, 1996), dolastatin 15 (Hamel, Med. Res. Rev. 16(2): 207-231, 1996), halichondrins and halistatins (Hamel, Med. Res. Rev. 16(2): 207-231, 1996), spongistatins (Hamel, Med. Res. Rev. 16(2): 207-231, 1996), cryptophycins (Hamel, Med. Res. Rev. 16(2): 207-231, 1996), rhazinilam (Hamel, Med. Res. Rev. 16(2): 207-231, 1996), betaine (Hashimoto et al., Zool. Sci. 1: 195-204, 1984), taurine (Hashimoto et al., Zool. Sci. 1: 195-204, 1984), isethionate (Hashimoto et al., Zool. Sci. 1: 195-204, 1984), HO-221 (Ando et al., Cancer Chemother Pharmacol. 37: 63-69, 1995), adociasulfate-2 (Sakowicz et al., Science 280: 292-295, 1998), estramustine (Panda et al., Proc. Natl. Acad. Sci. USA 94: 10560-10564, 1997), monoclonal anti-idiotypic antibodies (Leu et al., Proc. Natl. Acad. Sci. USA 91(22): 10690-10694, 1994), microtubule assembly promoting protein (taxol-like protein, TALP) (Hwang et al., Biochem. Biophys. Res. Commun. 208(3): 1174-1180, 1995), cell swelling induced by hypotonic (190 mosmol/L) conditions, insulin (100 mmol/L) or glutamine (10 mmol/L) (Haussinger et al., Biochem. Cell. Biol. 72(1-2): 12-19, 1994), dynein binding (Ohba et al., Biochim. Biophys. Acta 1158(3): 323-332, 1993), gibberelin (Mita and Shibaoka, Protoplasma 119(1/2): 100-109, 1984), XCHOI (kinesin-like protein) (Yonetani et al., Mol. Biol. Cell 7(suppl): 211 A, 1996), lysophosphatidic acid (Cook et al., Mol. Biol. Cell 6(suppl): 260A, 1995), lithium ion (Bhattacharyya and Wolff, Biochem. Biophys. Res. Commun. 73(2): 383-390, 1976), plant cell wall components (e.g., poly-L-lysine and extensin) (Akashi et al., Planta 182(3): 363-369, 1990), glycerol buffers (Schilstra et al., Biochem. J. 277(Pt. 3): 839-847, 1991; Farrell and Keates, Biochem. Cell. Biol. 68(11): 1256-1261, 1990; Lopez et al., J. Cell. Biochem. 43(3): 281-291, 1990), Triton X-100 microtubule stabilizing buffer (Brown et al., J. Cell Sci. 104(Pt. 2): 339-352, 1993; Safiejko-Mroczka and Bell, J. Histochem. Cytochem. 44(6): 641-656, 1996), microtubule associated proteins (e.g., MAP2, MAP4, tau, big tau, ensconsin, elongation factor-1-alpha (EF-1α) and E-MAP-115) (Burgess et al., Cell Motil. Cytoskeleton 20(4): 289-300, 1991; Saoudi et al., J. Cell. Sci. 108(Pt. 1): 357-367, 1995; Bulinski and Bossler, J. Cell. Sci. 107(Pt. 10): 2839-2849, 1994; Ookata et al., J. Cell Biol. 128(5): 849-862, 1995; Boyne et al., J. Comp. Neurol 358(2): 279-293, 1995; Ferreira and Caceres, J. Neurosci. 11(2): 392-400, 1991; Thurston et al., Chromosoma 105(1):20-30, 1996; Wang et al., Brain Res. Mol. Brain Res. 38(2): 200-208, 1996; Moore and Cyr, Mol. Biol. Cell 7(suppl): 221-A, 1996; Masson and Kreis, J. Cell Biol. 123(2), 357-371, 1993), cellular entities (e.g., histone H1, myelin basic protein and kinetochores) (Saoudi et al., J. Cell. Sci. 108(Pt. 1): 357-367, 1995; Simerly et al., J. Cell Biol. 111(4): 1491-1504, 1990), endogenous microtubular structures (e.g., axonemal structures, plugs and GTP caps) (Dye et al., Cell Motil. Cytoskeleton 21(3): 171-186, 1992; Azhar and Murphy, Cell Motil. Cytoskeleton 15(3): 156-161, 1990; Walker et al., J. Cell Biol. 114(1): 73-81, 1991; Drechsel and Kirschner, Curr. Biol. 4(12): 1053-1061, 1994), stable tubule only polypeptide (e.g., STOP145 and STOP220) (Pirollet et al., Biochim. Biophys. Acta 1160(1): 113-119, 1992; Pirollet et al., Biochemistry 31(37): 8849-8855, 1992; Bosc et al., Proc. Natl. Acad. Sci. USA 93(5): 2125-2130, 1996; Margolis et al., EMBO J. 9(12): 4095-4102, 1990) and tension from mitotic forces (Nicklas and Ward, J. Cell Biol. 126(5): 1241-1253, 1994), as well as any analogues and derivatives of any of the above. Such compounds can act by either depolymerizing microtubules (e.g., colchicine and vinblastine), or by stabilizing microtubule formation (e.g., paclitaxel).

In some embodiments, an anti-tumor agent include mitotic inhibitors, for example vinca alkaloid derivatives such as vinblastine vinorelbine, vindescine and vincristine; colchines allochochine, halichondrine, N-benzoyltrimethyl-methyl ether colchicinic acid, dolastatin 10, maystansine, rhizoxine, taxanes such as taxol (paclitaxel), docetaxel (Taxotere), 2'-N-[3-(dimethylamino)propyl]glutaramate (taxol derivative), thiocholchicine, trityl cysteine, tenipo-side, methotrexate, azathioprine, fluorouricil, cytocine arabinoside, 2'2'-difluorodeoxycytidine (gemcitabine), adriamycin and mitamycin. Alkylating agents, for example cis-platin, carboplatin oxiplatin, iproplatin, Ethyl ester of N-acetyl-DL-sarcosyl-L-leucine (Asaley or Asalex), 1,4-cyclohexadiene-1,4-dicarbamic acid, 2,5-bis(1-azirdinyl)-3, 6-dioxo-, diethyl ester (diaziquone), 1,4-bis(methanesulfonyloxy)butane (bisulfan or leucosulfan) chlorozotocin, clomesone, cyanomorpholinodoxorubicin, cyclodisone, dianhydroglactitol, fluorodopan, hepsulfam, mitomycin C, hycantheonemitomycin C, mitozolamide, 1-(2-chloroethyl)-4-(3-chloropropyl)-piperazine dihydrochloride, piperazinedione, pipobroman, porfiromycin, spirohydantoin mustard, teroxirone, tetraplatin, thiotepa, triethylenemelamine, uracil nitrogen mustard, bis(3-mesyloxypropyl)amine hydrochloride, mitomycin, nitrosoureas agents such as cyclohexylchloroethylnitrosourea, methylcyclohexyl-chloroethylnitrosourea 1-(2-chloroethyl)-3-(2,6-dioxo-3-piperidyl)-1-nitroso-urea, bis(2-chloroethyl)nitrosourea, procarbazine, dacarbazine, nitrogen mustard-related compounds such as mechloroethamine, cyclophosphamide, ifosamide, melphalan, chlorambucil, estramustine sodium phosphate, strptozoin, and temozolamide. DNA anti-metabolites, for example 5-fluorouracil, cytosine arabinoside, hydroxyurea, 2-[(3hydroxy-2-pyrinodinyl)methylene]-hydrazinecarbothioamide, deoxyfluorouridine, 5-hydroxy-2-formylpyridine thiosemicarbazone, alpha-2'-deoxy-6-thioguanosine, aphidicolin glycinate, 5-azadeoxycytidine, beta-thioguanine deoxyriboside, cyclocytidine, guanazole, inosine glycodialdehyde, macbecin II, pyrazolimidazole, cladribine, pentostatin, thioguanine, mercapturine, bleomycin, 2-chlorodeoxyadenosine, inhibitors of thymidylate synthase such as raltitrexed and pemetrexed disodium, clofarabine, floxuridine and fludarabine. DNA/RNA antimetabolites, for example, L-alanosine, 5-azacytidine, acivicin, aminopterin and derivatives thereof such as N-[2-chloro-5-[[(2,4-diamino-5-methyl-6-quinazolinyl)methyl]amino]benzoyl]-L-aspartic acid, N-[4-[[(2,4-diamino-5-ethyl-6-quinazolinyl) methyl]amino]benzoyl]-L-aspartic acid, N-[2-chloro-4-[[(2, 4-diaminopteridinyl)methyl]amino]benzoyl]-L-aspartic acid, soluble Baker's antifol, dichloroallyl lawsone, brequinar, ftoraf, dihydro-5-azacytidine, methotrexate, N-(phosphonoacetyl)-L-aspartic acid tetrasodium salt, pyrazofuran, trimetrexate, plicamycin, actinomycin D, cryptophycin, and analogs such as cryptophycin-52 or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; proteins, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide).

As used herein, the term "topoisomerase inhibitors" refers to agents that can modulcate the activity of topoisomerase I and/or topoisomerase II. In some embodiments, the topoisomerase inhibitor of this invention can be a topoisomerase I inhibitor, which can be, in some embodiments, a camptothecin derivative. A camptothecin derivative of this invention can be, but is not limited to Belotecan (CKD602), Camptothecin, 7-Ethyl-10-Hydroxy-CPT, 10-Hydroxy-CPT, Rubitecan (9-Nitro-CPT), 7-Ethyl-CPT, Topotecan, Irinotecan, Silatecan (DB67) and any combinations thereof. In some embodiments of this invention, the topoisomerase I inhibitor can be an indenoisoquinoline derivative, which can be but is not limited to NSC706744, NSC725776, NSC724998 and any combinations thereof. In further embodiments of this invention, the topoisomerase inhibitor is a topoisomerase II inhibitor, which in some embodiments can be an acridine derivative, which can be but is not limited to Amsacrine, in some embodiments the topoisomerase II inhibitor can be a podophyllotoxin derivative, which can be but is not limited to etoposide, and in some embodiments the topoisomerase II inhibitor can be a bisdioxopiperazine derivative, which can be but is not limited to ICRF-193, dexrazoxane (ICRF-187) and any combinations thereof. In yet further embodiments of this invention, the topoisomerase inhibitor can be Resveratrol (PMID: 20304553; PMID: 15796584)41, Epigallocatechin gallate (PMID: 18293940; PMID: 11594758; PMID: 11558576; PMID: 1313232)42,43, Genistein (PMID: 17458941)44, Daidzein (PMID: 17458941)45. Quercetin (PMID: 1313232; PMID: 16950806; PMID: 15312049), natural flavones related to quercetin that inhibit topoisomerase, such as acacetin, apigenin, kaempferol and morin (PMID: 8567688)46-48, Luteolin (PMID: 12027807; PMID: 16950806; PMID: 15312049)46; Myricetin (PMID: 20025993)49 and any combinations thereof. In certain embodiments, the topoisomerase inhibitor can be an interfering RNA (RNAi) molecule that targets topoisomerase I, topoisomerase II or both. Nonlimiting examples of RNAi molecules include small interfering RNA (siRNA), short hairpin RNA (shRNA), microRNA (miRNA), antisense nucleic acid molecules, and the like as are well known in the art. Nonlimiting examples of siRNAs and shRNAs of this invention are provided in Table 2. In some embodiments, a zinc finger nuclease, an antibody and/or a ribozyme can be employed to inhibit topoisomerase activity in the methods of this invention.

As used herein, the term "cytotoxic antibiotics" cytotoxic antibiotics include, but are not limited to, antinomycin, bleomycin, mitomycin, plicamycin and the like. Examples of tyrosine kinase inhibitors include, but are not limited to, nilotinib, imatinib, gefitinib, erlotinib, cetuximab, panitumumab, zalutumumab, nimotuzumab, matuzuman and the like.

In some embodiments, the other anti-cancer agents are monoclonal antibodies, such as alemtuzumab, bevacizumab, cetuximab, gemtuzumab, rituximab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin.

In some embodiments, the other anti-cancer agents are those can be used to treat leukemia, such as drugs for Acute Lymphoblastic Leukemia (ALL), Acute Myeloid Leukemia (AML), Chronic Lymphocytic Leukemia (CLL), Chronic Myelogenous Leukemia (CML), and Meningeal Leukemia, include but are not limited to, Abitrexate (Methotrexate), Adriamycin PFS (Doxorubicin Hydrochloride), Adriamycin RDF (Doxorubicin Hydrochloride), Arranon (Nelarabine), Asparaginase Erwinia chrysanthemi, Cerubidine (Daunorubicin Hydrochloride), Clafen (Cyclophosphamide), Clofarabine, Clofarex (Clofarabine), Clolar (Clofarabine), Cyclophosphamide, Cytarabine, Cytosar-U (Cytarabine), Cytoxan (Cyclophosphamide), Dasatinib, Daunorubicin Hydrochloride, Doxorubicin Hydrochloride, Erwinaze (Asparaginase Erwinia Chrysanthemi), Folex (Methotrexate), Folex PFS (Methotrexate), Gleevec (Imatinib Mesylate), Iclusig (Ponatinib Hydrochloride), Imatinib Mesylate, Marqibo (Vincristine Sulfate Liposome), Mercaptopurine, Methotrexate, Methotrexate LPF (Methorexate), Mexate (Methotrexate), Mexate-AQ (Methotrexate), Nelarabine, Neosar (Cyclophosphamide), Oncaspar (Pegaspargase), Pegaspargase, Purinethol (Mercaptopurine), Rubidomycin (Daunorubicin Hydrochloride), Sprycel (Dasatinib), Tarabine PFS (Cytarabine), Vincasar PFS, incristine Sulfate), Vincristine Sulfate, Vincristine Sulfate Liposome, Hyper-CVAD, Adriamycin PFS (Doxorubicin Hydrochloride), Adriamycin RDF (Doxorubicin Hydrochloride), Arsenic Trioxide, Cerubidine (Daunorubicin Hydrochloride), Clafen (Cyclophosphamide), Cyclophosphamide, Cytarabine, Cytosar-U (Cytarabine), Cytoxan (Cyclophosphamide), Daunorubicin Hydrochloride, Doxorubicin Hydrochloride, Neosar (Cyclophosphamide), Rubidomycin (Daunorubicin Hydrochloride), Tarabine PFS (Cytarabine), Trisenox (Arsenic Trioxide), Vincasar PFS (Vincristine Sulfate), Vincristine Sulfate, ADE, Alemtuzumab, Ambochlorin (Chlorambucil), Amboclorin (Chlorambucil), Arzerra (Ofatumumab), Bendamustine, Hydrochloride, Campath (Alemtuzumab), Chlorambucil, Clafen (Cyclophosphamide), Cyclophosphamide, Cytoxan (Cyclophosphamide), Fludara (Fludarabine Phosphate), Fludarabine Phosphate, Gazyva (Obinutuzumab), Ibrutinib, Imbruvica (Ibrutinib), Leukeran (Chlorambucil), Linfolizin (Chlorambucil), Neosar (Cyclophosphamide), Obinutuzumab, Ofatumumab, Treanda (Bendamustine Hydrochloride), CHLORAMBUCIL-PREDNISONE, CVP, Bosulif (Bosutinib), Bosutinib, Busulfan, Busulfex (Busulfan), Clafen (Cyclophosphamide), Cyclophosphamide, Cytarabine, Cytosar-U (Cytarabine), Cytoxan (Cyclophosphamide), Dasatinib, Gleevec (Imatinib Mesylate), Iclusig (Ponatinib Hydrochloride), Imatinib Mesylate, Myleran (Busulfan), Neosar (Cyclophosphamide), Nilotinib, Omacetaxine Mepesuccinate, Ponatinib Hydrochloride, Sprycel (Dasatinib), Synribo (Omacetaxine Mepesuccinate), Tarabine PFS (Cytarabine), Tasigna (Nilotinib), Cytarabine, Cytosar-U (Cytarabine), and Tarabine PFS (Cytarabine).

In some embodiments, additional anti-cancer agents that can be used together with the compounds of the present invention include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor. EGFR inhibitors are described in, for example in WO 95/19970, WO 98/14451, WO 98/02434 and U.S. Pat. No. 5,747,498. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). VEGF inhibitors, for example AG-13736 (Pfizer, Inc.), can also be combined or co-administered with the composition. VEGF inhibitors are described in, for example in WO 99/24440, WO 95/21613, WO 99/61422, U.S. Pat. No. 5,834,504, WO 98/50356 (published Nov. 12, 1998), U.S. Pat. Nos. 5,883,113, 5,886,020, 5,792,783, 6,534,524, WO 99/10349, WO 97/32856, WO 97/22596, WO 98/54093, and WO 98/02437, all of which are herein incorporated by reference in their entirety. Other examples of some specific VEGF inhibitors are IM862 (Cytran Inc. of Kirkland, Wash., USA); Avastin™ or bevacizumab, an anti-VEGF monoclonal antibody (Genentech, Inc. of South San Francisco, Calif.); and angiozyme, a synthetic ribozyme from Ribozyme (Boulder, Colo.) and Chiron (Emeryville, Calif.). ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with the composition. Such erbB2 inhibitors include those described in WO 98/02434, WO 99/35146, WO 99/35132, WO 98/02437, WO 97/13760, WO 95/19970, U.S. Pat. Nos. 5,587,458, and 5,877,305, each of which is herein incorporated by reference in its entirety.

In some embodiments, a continuous dosing schedule is used for the treatment. In some embodiments, a compound of a dosage form comprising the compound of the present invention is administered once per day, twice per day, three times per day, or more times per day, or continuously during a period of a day, or continuously through out a day, on a daily schedule, or every other day, every third day, every forth day, every fifth day, every sixth day, or every week. The treatment can last a period of time determined by doctors, or until the cancer cells are completely or significantly inhibited.

In some embodiments, an intermittent dosing schedule is used for the treatment. Such treatment is especially useful if there is toxicity concern. In some embodiments, The following examples illustrate various aspects of the invention. The examples should, of course, be understood to be merely illustrative of only certain embodiments of the invention and not to constitute limitations upon the scope of the invention.

EXAMPLES

Example 1

In Vitro Antiproliferative Activity of LOR-253 in Leukemia, Lymphoma and Multiple Myeloma Cell Lines Antiproliferative activity of LOR-253 was determined by XTT assay as follows. Cells ($4 \times 10^3$/well) in 100 µL of growth medium were seeded in 96-well cell culture plates and incubated overnight at 37° C. The medium was removed and replaced with a total volume of 100 µL growth medium containing LOR-253 (or 0.1% DMSO vehicle control), as described in the respective experiments. Suspension cells were plated (4-6×10³/well) in 50 µL growth medium, and 50 µL growth medium containing LOR-253 (or 0.1% DMSO vehicle control) was added to each well. After incubation of the cells at 37° C. for 5 days, cell viability was quantitated with the use of sodium 3'-[1-(phenylamino-carbonyl)-3,4-tetrazolium}-bis(4-methoxy-6-nitro) benzene sulfonic acid hydrate (XTT) colorimetric assay (Roche). XTT labeling reagent (1 mg/mL) was mixed with electron-coupling reagent, following the manufacturer's instructions, and 50 µL of the mixture was added directly to the cells. The plates were further incubated at 37° C. for 4 h, and the absorbance of each well was measured at 490 nm with a multiwell spectrophotometer (Bio-Tek Instruments Inc.). The data were adjusted relative to the blank and expressed as a percentage of cell growth compared with the vehicle control. (Ref. Huesca et al., Mol Cancer Ther. 2009. 8:2586-96; Lorus publication on LOR-133)

Figure 3:
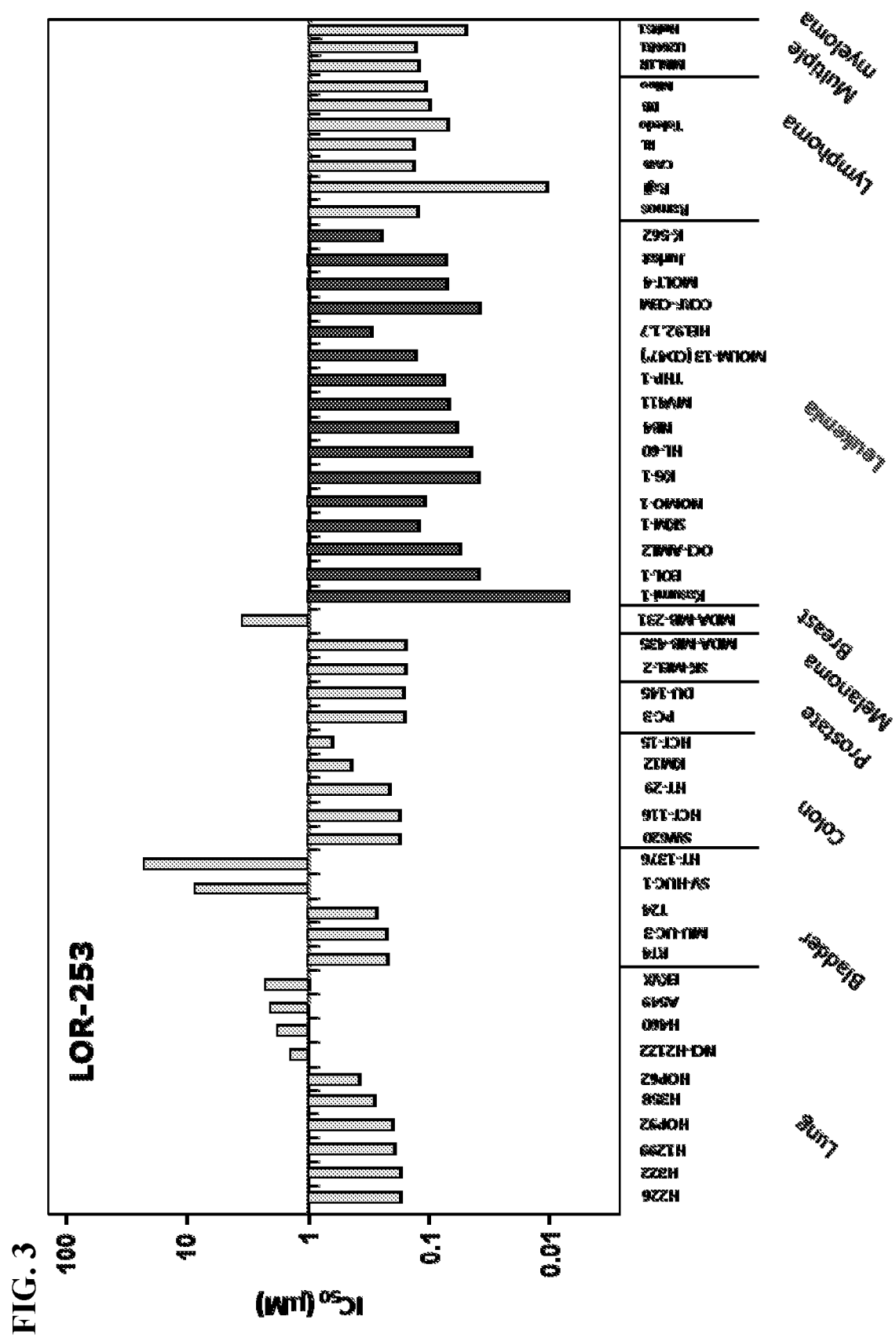
FIG. 3 is a graphical representation of the effect of LOR-253 on proliferation of a number of cancer cell lines in vitro. Cells of various cancer cell lines were incubated with LOR-253 as described in the Examples, and the cell concentrations of various cell lines for 50% of maximal inhibition of cell proliferation ($GI_{50}$) by LOR-253 were determined and shown in the figure.

The in vitro essay results (FIG. 3) indicate that leukemia/lymphoma, including AML cell lines, such as HL-60, MV 411, THP-1, HEL92.1.7, CCRF-CEM, MOLT-4, Jurkat, K-562, Ramos, and Raji, are the cell lines most sensitive to LOR-253, while other cell lines of lung cancer, bladder cancer, colon cancer, prostate cancer, melanoma, and breast cancer, are less sensitive to LOR-253. The variability in sensitivity to LOR-253 may be attributable to the extent of innate KLF4 suppression. The $IC_{50}$ values of LOR-253 for each leukemia and lymphoma cell lines are shown below.

| Cancer Type | Cell Line | $IC_{50}$ (µM) |
| --- | --- | --- |
| Acute myeloid leukemia | Kasumi-1 | 0.0069 |
|  | KG-1 | 0.033 |
|  | HL-60 | 0.046 |
|  | EOL-1 | 0.058 |
|  | NB4 | 0.06 |
|  | MV-4-11 | 0.069 |
|  | OCI-AML2 | 0.076 |
|  | THP-1 | 0.077 |
|  | MOLM13 (CD47+) | 0.13 |
|  | NOMO-1 | 0.121 |
|  | SKM-1 | 0.145 |
|  | HEL92.1.7 | 0.305 |
| Acute lymphoblastic leukemia | CCRF-CEM | 0.039 |
|  | MOLT-4 | 0.07 |
|  | Jurkat | 0.071 |
| Chronic Myelogenous Leukemia | K562 | 0.25 |
| Non-Hodgkin's Lymphoma | Ramos | 0.125 |
|  | Raji | 0.011 |
|  | CA46 | 0.19 |
|  | Toledo | 0.077 |
|  | DB | 0.099 |
|  | Mino | 0.14 |
|  | RL | 0.19 |
| Multiple myeloma | MM.1R | 0.15 |
|  | U266B1 | 0.18 |
|  | HuNS1 | 0.072 |

Example 2

KLF4/p21 Induction in AML Cell Lines In Vitro

Figure 4:
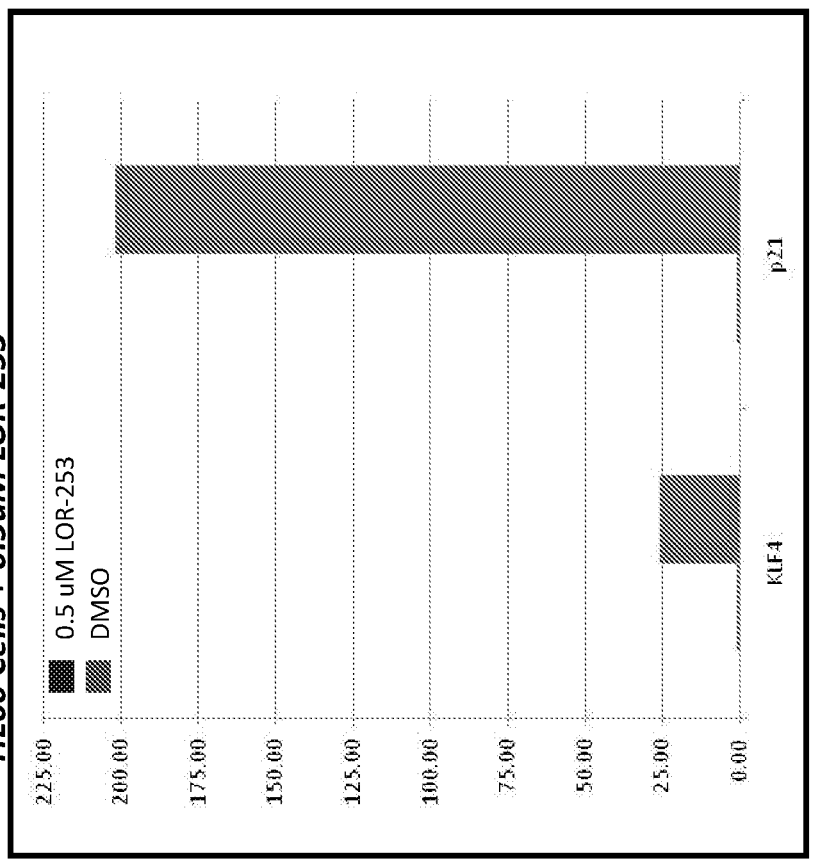
FIG. 4 is a graphical representation of the effect of LOR-253 on the expression levels of KLF4 in two cell lines, THP-1 and HL60.
Figure 4:
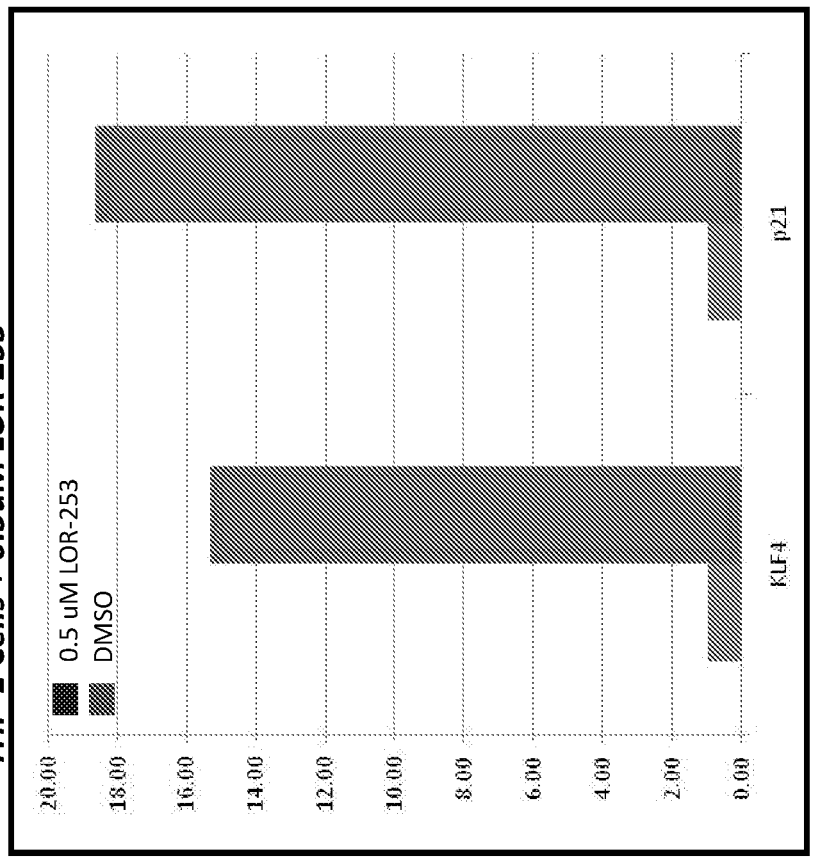

To determine if KLF4 and/or p21 expressions are induced by LOR-253, AML cells (THP1, HL-60) were treated with DMSO (vehicle control) or 0.5 µM LOR-253 for 16 hours. Total RNA was extracted using the TRIzol Plus RNA Purification kit (Ambion, Life Technologies), according to the manufacturer's instructions. First strand cDNA was synthesized from 1-2 ug total RNA using random hexamer primers (Invitrogen) and the SuperScript II Reverse Transcriptase kit (Invitrogen). Quantitative RT-PCR was performed in the ABI Prism 7000 Sequence Detection System using cDNAs and human TaqMan Gene Expression Assay primer/probe sets for Krüppel-like factor 4 (KLF4), cyclin-dependent kinase inhibitor 1A (p21) and the ABI TaqMan Universal PCR master mix protocol. Gene expression was normalized with β-actin gene expression in the same sample, and fold changes in KLF4 or p21 were expressed relative to the corresponding expression level in the DMSO treated samples using the comparative CT method. Treatment of THP1 and HL-60 AML cell lines with LOR-253 results in increased expression KLF4 and p21 (See FIG. 4).

Example 3

Treatment with LOR-253 Results in G1/S Cell Cycle Arrest in AML Cell Lines

Figure 5:
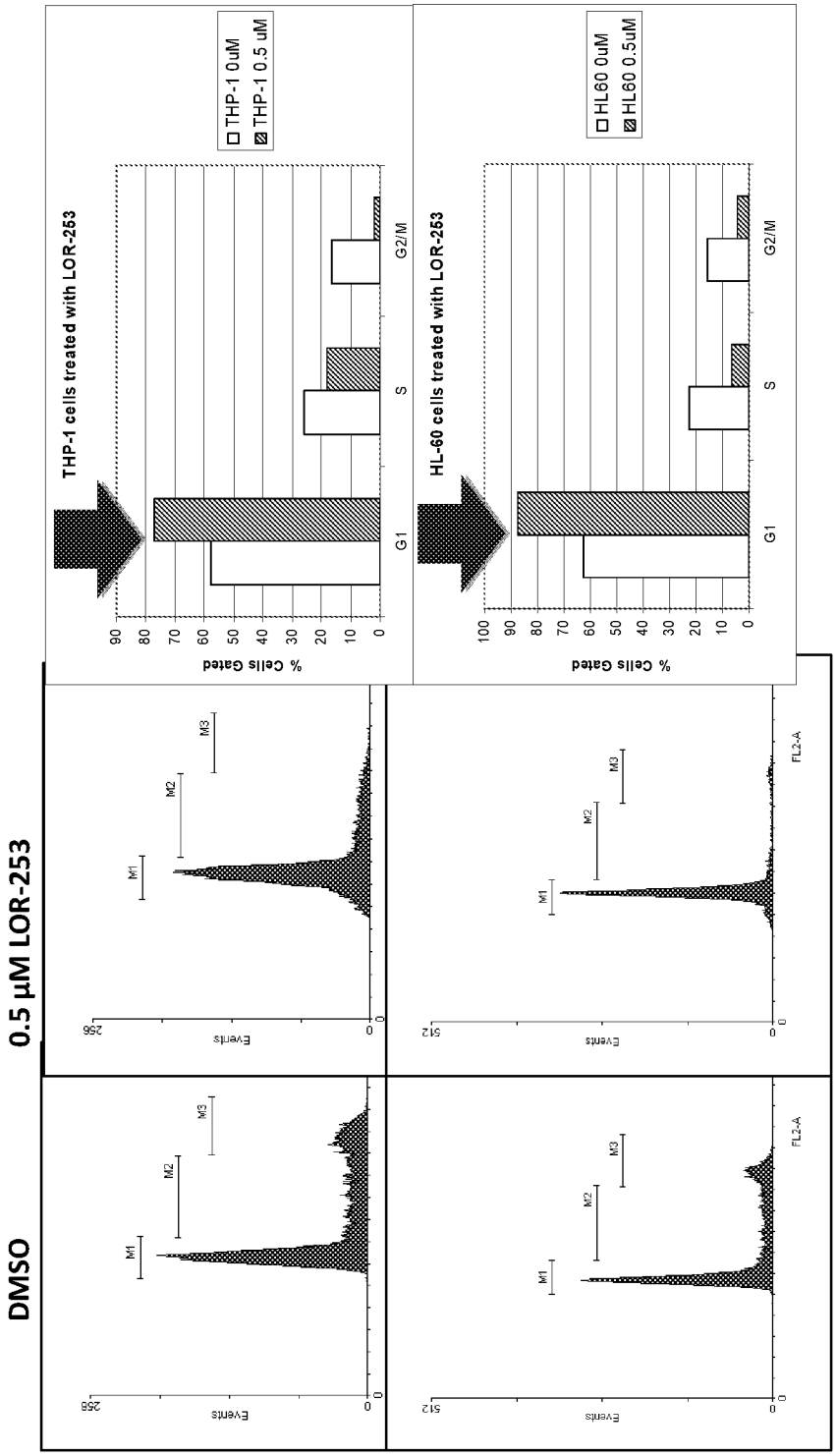
FIG. 5 depicts BD FACSCalibur flow cytometer assay result for THP1 and HL-60 AML cell lines treated with DMSO or LOR-253 (left panel).

THP1 and HL-60 AML cell lines were treated with DMSO (vehicle control) or 0.5 µM LOR-253 for 16 hours. Cells were washed once in PBS+1% FCS and fixed using ice cold 70% ethanol overnight. Fixed cells were washed twice, resuspended in PI/RNaseA solution, containing 20 µg/mL propidium iodide and 250 µg/mL RNaseA, and stained for 30 minuets at 37° C. Stained cells were analyzed using a BD FACSCalibur flow cytometer. The results indicate treatment with LOR-253 results in G1/S cell cycle arrest in AML cell lines (FIG. 5)

Example 4

Treatment with LOR-253 Induces Apoptosis in Cell Lines

Figure 6:
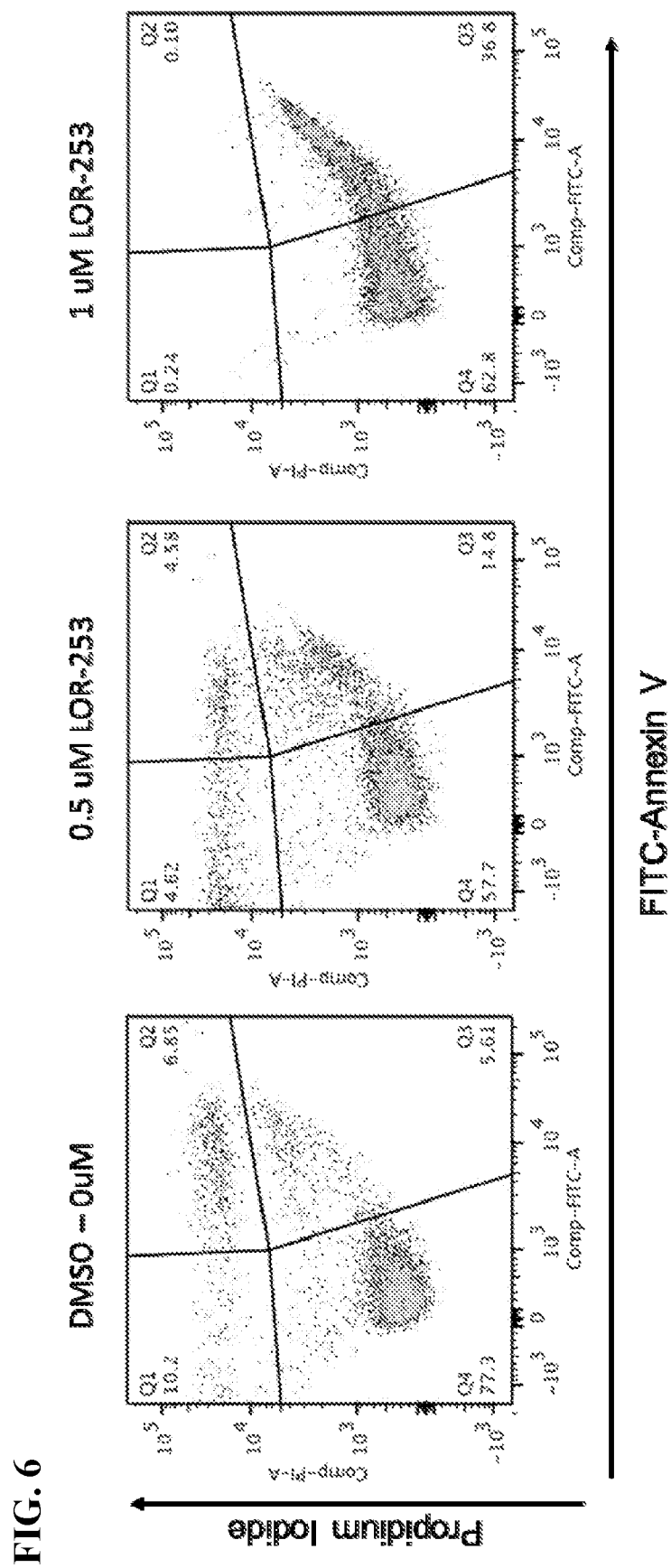
FIG. 6 depicts a BD FACSCanto flow cytometry acquisition plots for THP-1 cells treated with DMSO, 0.5 or 1 uM of LOR-253. THP-1 cells treated with LOR-253 showed elevated Annexin V staining, indicating induction of apoptosis (Q3: Annexin V+/PI−).

THP-1 cells were treated with DMSO, 0.5 or 1 uM of LOR-253 for 16 hours. Cells were washed twice with cold PBS and resuspended Annexin V binding buffer. 1×10⁵ cells in 100 µL were stained with FITC-Annexin V and propidium iodide, and incubated for 15 minutes at room temperature. After staining, 400 ul of binding buffer was added and the cells were kept on ice until analyzed on a BD FACSCanto flow cytometer. THP-1 cells treated with LOR-253 showed elevated Annexin V staining, indicating induction of apoptosis. Increasing concentration of LOR-253 used to treat the cells resulted in an increase in the early apoptotic population (Q3: Annexin V+/PI−). The results indicate treatment with LOR-253 induces apoptosis in AML cell lines (FIG. 6).

Figure 7:
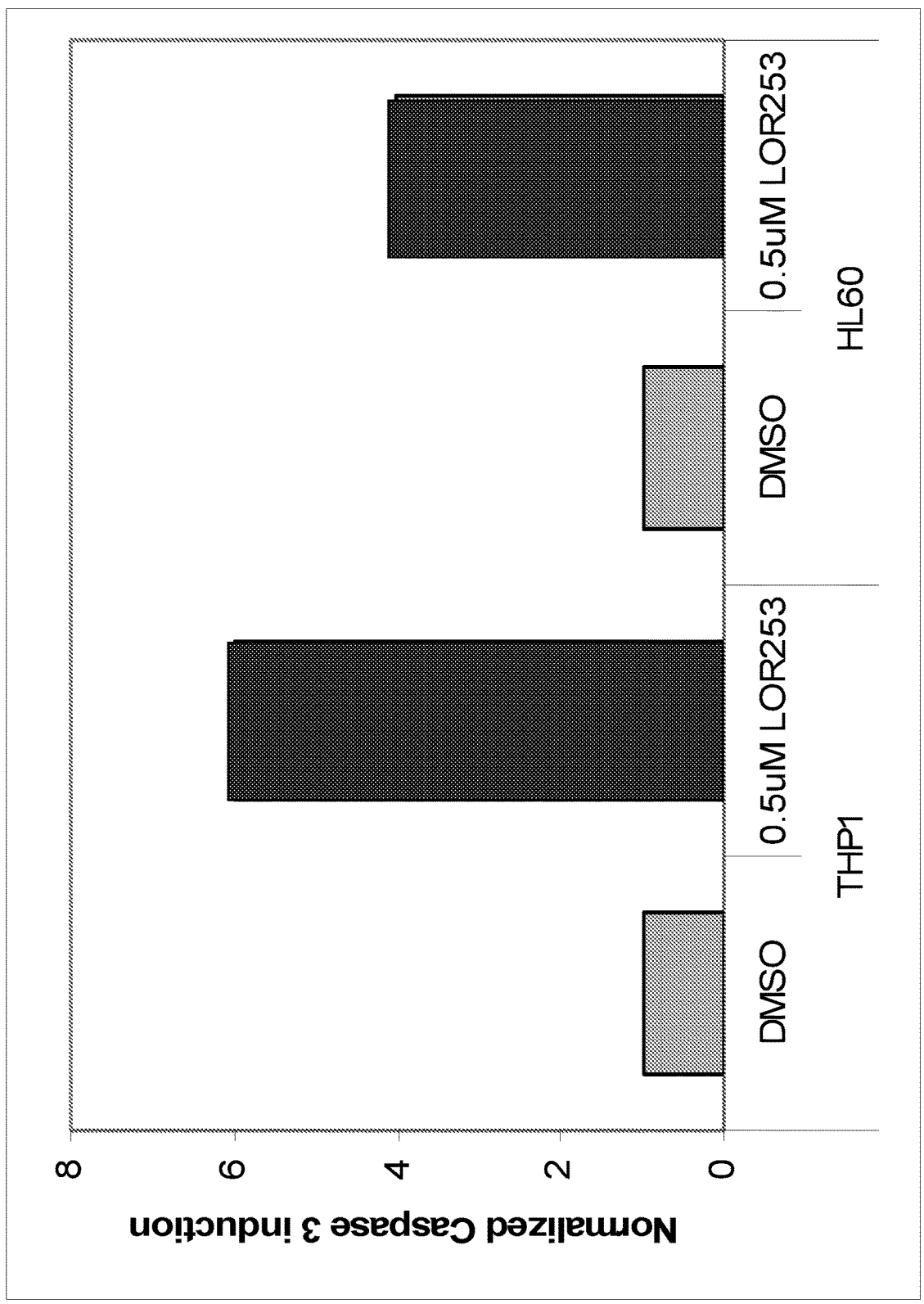
FIG. 7 depicts Caspase 3 expression level in THP1 and HL-60 AML cell lines treated with DMSO or LOR-253.

THP1 and HL-60 cells were treated with DMSO (vehicle control) or 0.5 µM LOR-253 for 48 hours. Cell lysates were collected using a 1% Triton-X100 lysis. Caspase 3 activity was measured using EnzChek Caspase-3 Assay Kit #1 (Life Technologies) with 5 µg of cell lysates according to manufacturer's protocol. Treatment of THP1 and HL-60 cells with LOR-253 results in elevated Caspase 3 activity, indicating induction of apoptosis (FIG. 7).

Figure 8:
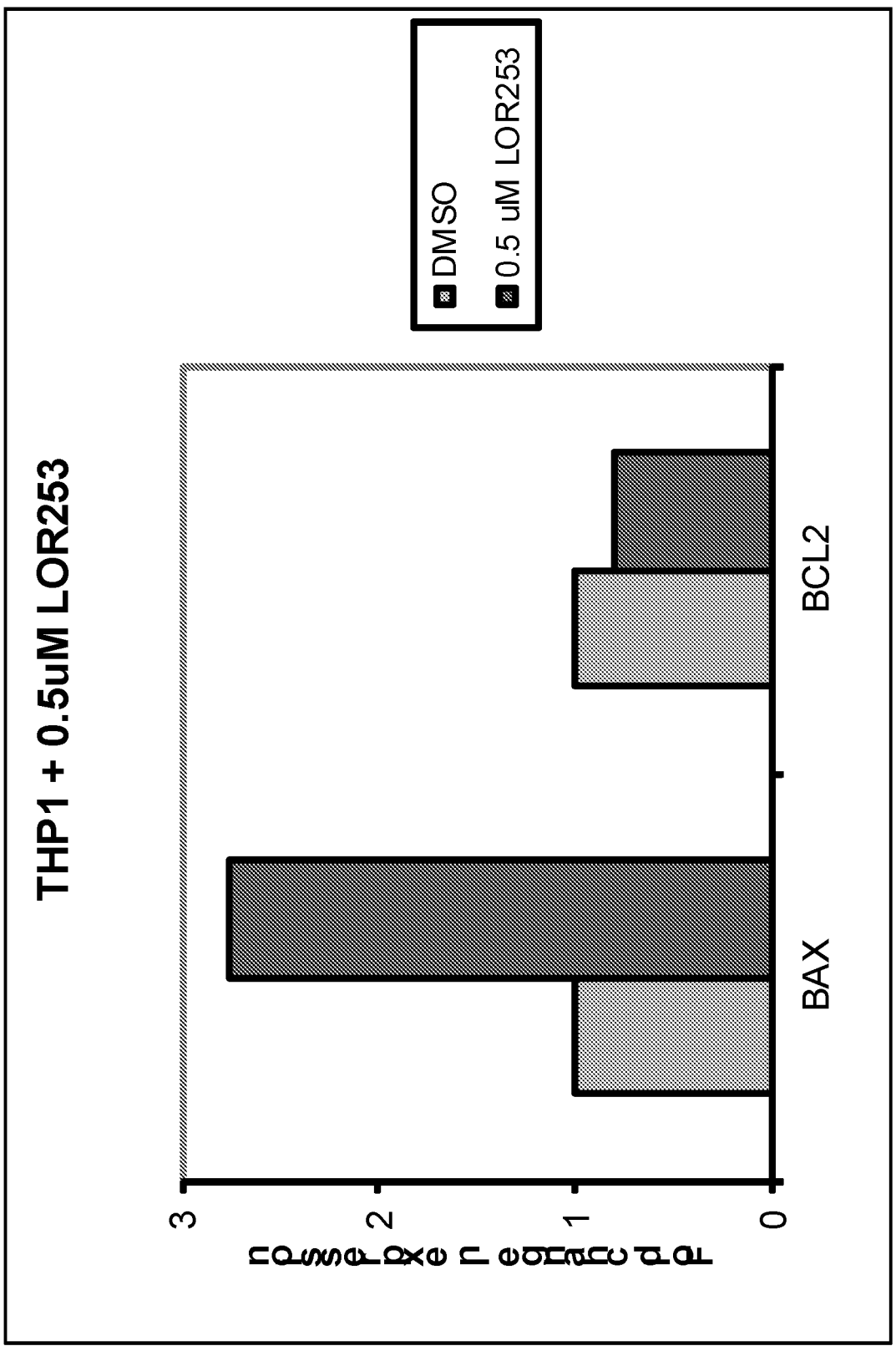
FIG. 8 depicts fold change in expression of BAX and BCL2 in THP1 cells treated with DMSO or 0.5 µM LOR-253

THP1 cells were treated with DMSO (vehicle control) or 0.5 µM LOR-253 for 48 hours. Total RNA was extracted using the TRIzol Plus RNA Purification kit (Ambion, Life Technologies), according to the manufacturer's instructions. First strand cDNA was synthesized from 1-2 ug total RNA using random hexamer primers (Invitrogen) and the Super- Script II Reverse Transcriptase kit (Invitrogen). Quantitative RT-PCR was performed in the ABI Prism 7000 Sequence Detection System using cDNAs and human TaqMan Gene Expression Assay primer/probe sets for BCL2-associated X protein (BAX), B-cell CLL/Lymphoma 2 (BCL2) and the ABI TaqMan Universal PCR master mix protocol. Gene expression was normalized with β-actin gene expression in the same sample, and fold changes in BAX or BCL2 were expressed relative to the corresponding expression level in the DMSO treated samples using the comparative CT method. Elevation of BAX and repression of BCL2 upon treatment of THP1 cells with LOR-253 indicates induction of apoptosis (FIG. 8).

Example 5

In Vivo Efficacy of LOR-253 HCL in H226 Xenograft Model—Dose and Schedule

H226 model mice were treated according to several administration schedules as shown in the table below.

| Group | Dose level | Administration Schedule/cycle (days) | Treatment (1 cycle = 28 day) |
|---|---|---|---|
| 1 | n = 8 | 10 mg/kg-iv | 2T-12B-2T | 2 cycles |
| 2 | n = 8 | 10 mg/kg-iv | 3T-12B-3T | 2 cycles |
| 3 | n = 8 | 10 mg/kg-iv | 2T-5B-2T | 2 cycles |
| 4 | n = 8 | 10 mg/kg-iv | 3T-5B-3T | 2 cycles |
| 5 | n = 8 | Vehicle alone | 3T-5B-3T | 2 cycles |

T = consecutive days treatment
B = break for one

Figure 9:
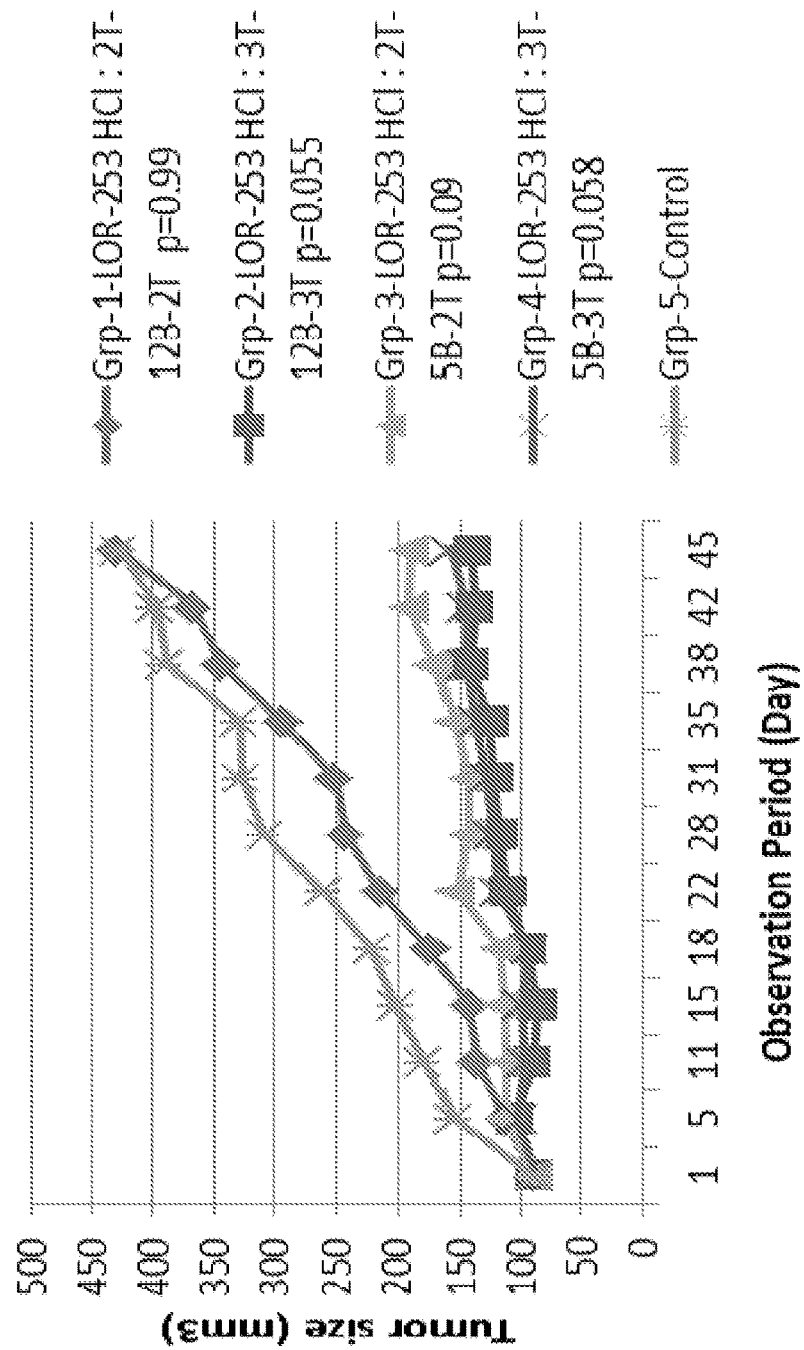
FIG. 9 depicts in vivo efficacy of LOR-253 HCL in H226 xenograft model mice. Tumor sizes of H226 xenograft mice treated with LOR-253 HCL or negative control measured on the indicated days are shown.

The results show that groups 2, 3, and 4 are effectively treated by LOR-253 (FIG. 9). The results indicates that schedule with one week gap is superior to two-week gap, and suggests weekly administration schedule is preferred.

Example 6

Figure 10:
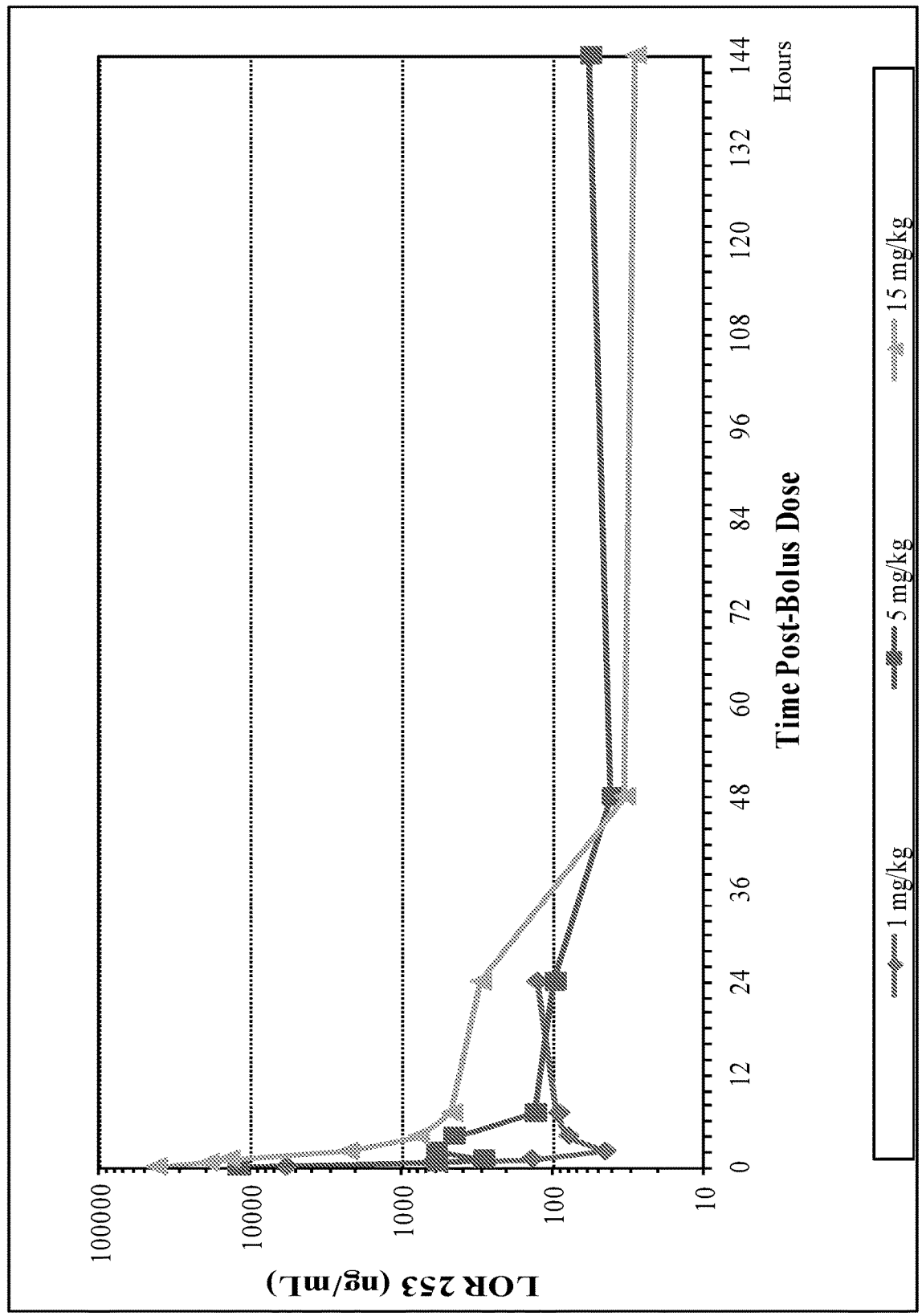
FIG. 10 depicts the pharmacokinetic (PK) in CD-1 nude mice treated by LOR-253 at a dosage of 1, 5, or 15 mg/kg. The serum level of LOR-253 has a dose related increase.

In Vivo Dose-Dependent Pharmacokinetic (PK) and Pharmacodynamic (PD) Responses in Xenograft CD-1 Nude Mice Treated by LOR-253 HCL To study the pharmacokinetic (PK) in tumor cells treated by LOR-253, CD-1 nude mice were treated by i.v. bolus injections of LOR-253 HCl at 1, 5, and 15 mg/kg. The serum level of LOR-253 was measured. The result indicates that the serum level of LOR-253 has a dose related increase (FIG. 10).

Figure 11:
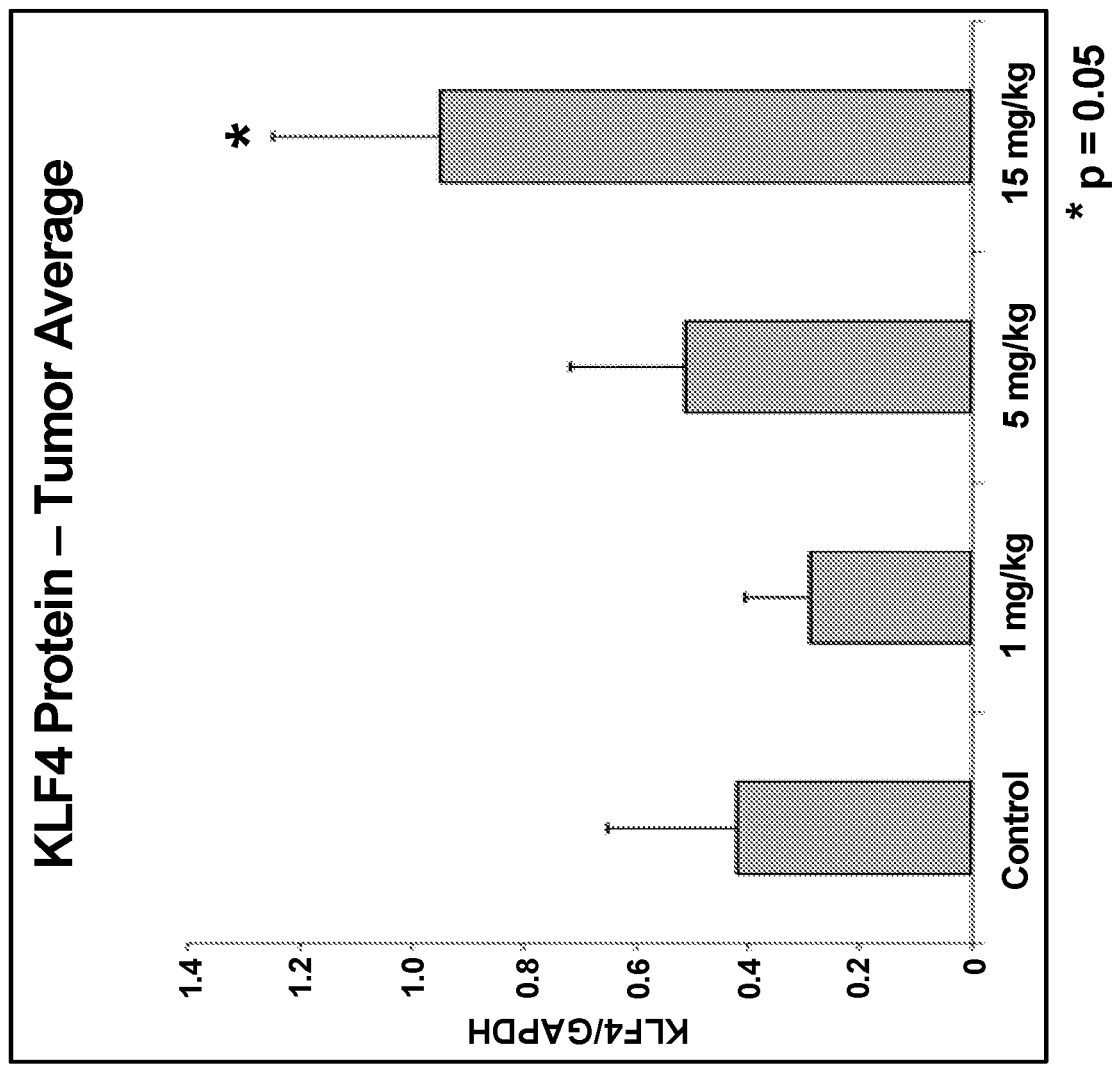
FIG. 11 depicts the pharmacodynamic (PD) responses in mice treated for 5 consecutive days with 1, 5, and 15 mg/kg LOR-253. The KLF4 protein level was measured 16 hours after the last dose.

To study the pharmacodynamic (PD) responses, mice were treated for 5 consecutive days with 1, 5, and 15 mg/kg LOR-253. Tumors were measured 16 hours after the last dose, and the KLF-4 protein level was measured. Average KLF4 protein levels increased in a dose-dependent manner, correlating with tumor biodistribution and dose-response antitumor activity (FIG. 11).

Example 7

LOR-253 for Treating AML, Phase I Clinical Trial

Preclinical testing established a broad therapeutic index for LOR-253: efficacy of LOR-253 was demonstrated in xenograft models against multiple tumor types; extensive GLP safety and PK studies were performed in rats and dogs; no treatment-related cardiovascular effects were observed in repeat-dose toxicity study of dogs at highest dose tested (data not shown); no significant inhibition of hERG tail current density or CYP450 enzymes; and GLP blood compatibility studies confirmed the suitability of IV formulation.

Figure 12:
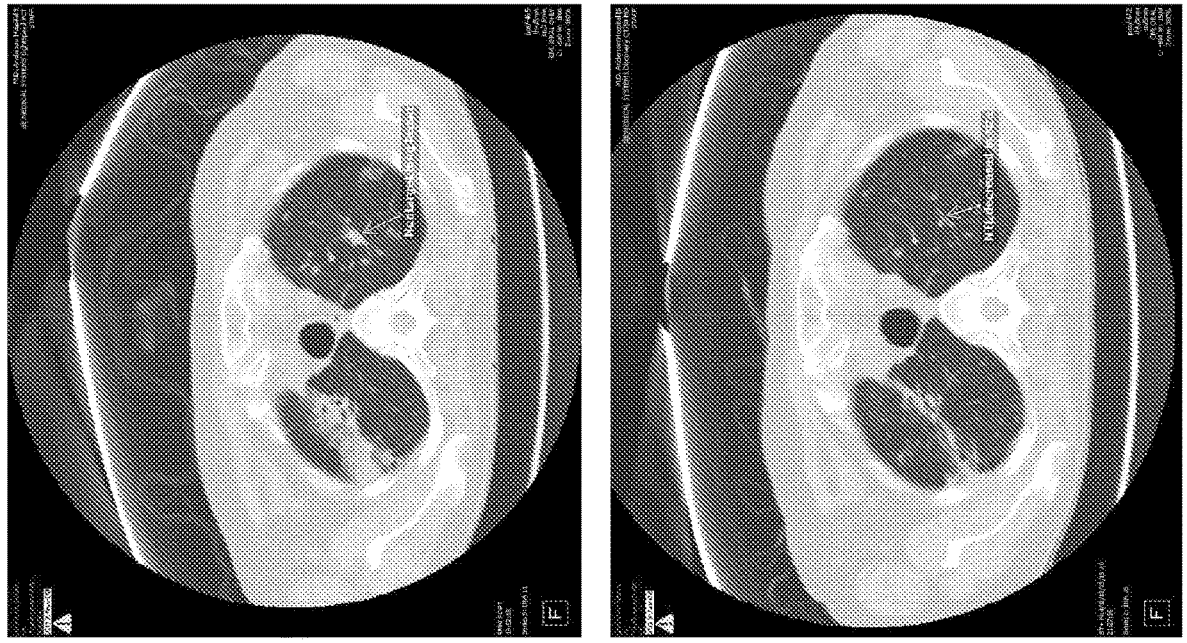
FIG. 12 depicts tumor shrinkage in patient with NSCLC (poorly differentiated adenocarcinoma) before the treatment (see the upper panel) and after the treatment (see the lower panel).

Phase I: This was an open-label, phase 1 study to determine the maximum tolerated dose (MTD) or appropriate target dose if MTD not reached to identify the recommended phase 2 dose of LOR-253 HCl in patients with advanced or metastatic solid tumours. In the first set of doses, LOR-253 HCl was given in ascending doses until the maximum administered dose or appropriate target dose is reached. In the other set of doses, LOR-253 HCl was given in ascending doses starting from 20 mg/m2 until the maximum administered dose or appropriate target dose is reached. Patient as treated on LOR-253 HCl for 2 cycles for the evaluation.
Other Name: No other names are used.
Study Type: Interventional
Study Design: Endpoint Classification: Safety Study
  Intervention Model: Single Group Assignment
  Masking: Open Label
  Primary Purpose: Treatment
Official Title: Open-Label, Phase 1 Study of LOR-253 HCl in Patients With Advanced or Metastatic Solid Tumours
Primary Outcome Measures:
  To determine the maximum tolerated dose (MTD) or appropriate target dose if MTD not reached to identify the recommended phase 2 dose of LOR-253 HCl in patients with advanced or metastatic solid tumours. [Time Frame: 8 weeks]
Secondary Outcome Measures:
  To characterize the safety profile of LOR-253 HCl when administered to patients with advanced or metastatic solid tumours. [Time Frame: 8 weeks]
Inclusion Criteria:
  1. Male or female 18 years of age or older.
  2. Histologically confirmed diagnosis of solid tumor for which no effective therapy is available or that is unresponsive to conventional therapy.
  3. Meet laboratory parameter requirements at study entry.
Exclusion Criteria:
  1. Chemotherapy, radiotherapy, biologic therapy, immunotherapy or any other investigational drugs within 21 days of beginning study treatment with LOR-253 HCl.
  2. A hematologic malignancy.
  3. A history of brain or other central nervous system metastases.
  4. Have a presence of a significant infection.
  5. Clinically significant autoimmune disease.
  6. Uncontrolled intercurrent illness.
  7. With iron or copper overload syndromes.
  8. Pregnancy or breast feeding.
Safety and Antitumor Activity Demonstrated in Phase I Trial:
  Dose-Escalating Study in Patients with Advanced Solid Tumors
  Excellent Safety Profile (N=27 Patients) across 7 dose levels
  Most common AE and SAE: Fatigue and 1 case of reversible hypophosphatemia
  Stable Disease achieved in 41% of evaluable patients; No RECIST PR
  Tumor shrinkage (FIG. 12) in patient with NSCLC (poorly differentiated adenocarcinoma) and extensive metastases refractory to prior standard and investigational therapies
The phase I trial results demonstrated that LOR-253 is a safe and active drug for treating solid tumors.

Example 8

In Vitro Antiproliferative Activity of LOR-253 in Myelodysplastic Syndromes (MDS), Acute Lymphocytic Leukemia (ALL), Chronic Myelogenous Leukemia (CML), Adult T-Cell Leukaemia (ATLL), Lymphoma, Gastric Cancer, and Multiple Myeloma Cell Lines Antiproliferative activity of LOR-253 in MDS, ALL, CML, ATLL, lymphoma, gastric cancer, and multiple myeloma cell lines are determined by XTT assay as described in Example 1.

MDS cell lines tested in the assay include, but are not limited to, TER-3 (Mishima et al., New human myelodysplastic cell line, TER-3: G-CSF specific downregulation of Ca2+/calmodulin-dependent protein kinase IV, J Cell Physiol. 2002 May; 191(2):183-90), MDS92 (Tohyama et al., A novel factor-dependent human myelodysplastic cell line, MDS92, contains haemopoietic cells of several lineages, Br J Haematol. 1995 December; 91(4):795-9), and SKM-1 (Kimura et al., Antiproliferative and Antitumor Effects of Azacitidine Against the Human Myelodysplastic Syndrome Cell Line SKM-1, Anticancer Research 32:795-798, 2002), each of which is herein incorporated by reference in its entirety.

ALL cell lines tested in the assay include, but are not limited to, CCRF-CEM (Foley et al., Continuous culture of human lymphoblasts from peripheral blood of a child with acute leukemia. Cancer 1965 18:522-529), MOLT-4 (Minowada et al., Rosette-forming human lymphoid cell lines. I. Establishment and evidence for origin of thymus-derived lymphocytes. Journal of the National Cancer Institute 1972 49 (3): 891-895), and Jurkat (Schneider et al., Characterization of EBV-genome negative "null" and "T" cell lines derived from children with acute lymphoblastic leukemia and leukemic transformed non-Hodgkin lymphoma. Int J Cancer. 1977 May 15; 19(5):621-6).

CML cell lines tested in the assay include, but are not limited to, K562 (Drexler, Leukemia cell lines: in vitro models for the study of chronic myeloid leukemia. Leuk Res. 1994 December; 18(12):919-27).

Lymphoma cell lines tested in the assay include, but are not limited to, Ramos, Raji, CA46, Toledo, DB, Mino, and RL.

Gastric cancer cell lines tested in the assay include, but are not limited to, AGS (ATCC Accession No. CRL-1739TM), SNU-1 (ATCC Accession No. CRL-5971TM), SNU-5 (ATCC Accession No. CRL-5973TM), SNU-16 (ATCC Accession No. CRL-5974TM), Hs 746T (ATCC Accession No. HTB-135TM), NCI-N87 (N87; ATCC Accession No. CRL-5822TM), KATO III (ATCC Accession No. HTB-103TM), SNU-520, SNU-719, NUGC-4, STKM-2, MKN-45, MKN-74, 20M, AKG, ECC4, G42LATE, GCIY, GCIY, GT3TKB, H-111, H-162, H-30, H-55, HGC-27, HSC-39, HUG-1N, JR1, KWS, MKN-1, MKN-28, MKN-7, MKN-74, MKN-74, MKN-74, NCI-N87, NUGC-3, OKAJIMA, SK-GT-1, SK-GT-2, SK-GT-5, SNU-16, SNU-216, SNU-484, SNU-55, SNU-601, SNU-638, SNU-668, TGBC11TKB, TGBC11TKB, TMK-1, and YCC-3

Multiple myeloma cell lines tested in the assay include, but are not limited to, HMCLs described in Lombardi et al. (Molecular characterization of human multiple myeloma cell lines by integrative genomics: insights into the biology of the disease. Genes Chromosomes Cancer. 2007 March; 46(3):226-38.), XGs, NANs, BCN, MDN, SBN HMCLs, U266, RPMI8226, RPMI1640, ANBL-6, KMS-11, KMS12-BM, KMS12-PE, KMM1, LP1, L363, OPM2, NCI-H929, JIM3, MO-1, LP1, L363, NCIH929, OPM2, UHKT-89, SKMM2, U266B1 (Nilsson et al., Established immunoglobulin producing myeloma (IgE) and lymphoblastoid (IgG) cell lines from an IgE myeloma patient. Clin Exp Immunol. 1970 October; 7(4):477-89), MM.1R (Greenstein et al., Characterization of the MM.1 human multiple myeloma (MM) cell lines: a model system to elucidate the characteristics, behavior, and signaling of steroid-sensitive and -resistant MM cells. Exp Hematol. 2003 April; 31(4): 271-82), and HuNS1 (Winkelhake, Myelomas for producing human/human hybridomas. U.S. Pat. No. 4,720,459 dated Jan. 19, 1988).

The in vitro essay results indicate that one or more cell lines of MDS, ALL, CML, ATLL, lymphoma, gastric cancer, or multiple myeloma cell lines are sensitive to LOR-253.

Example 9

KLF4/p21 Induction in Myelodysplastic Syndromes (MDS), ALL, CML, ATLL, Lymphoma, Gastric Cancer, and Multiple Myeloma Cell Lines In Vitro To determine if KLF4 and/or p21 expressions are induced by LOR-253, myelodysplastic syndromes (MDS), ALL, CML, ATLL, lymphoma, gastric cancer, and multiple myeloma cell lines described in Example 8 are treated with DMSO (vehicle control) or 0.1, 0.2, 0.5 or 1 µM LOR-253 for 16 hours. Total RNA is extracted using the TRIzol Plus RNA Purification kit (Ambion, Life Technologies), according to the manufacturer's instructions. First strand cDNA is synthesized from 1-2 ug total RNA using random hexamer primers (Invitrogen) and the SuperScript II Reverse Transcriptase kit (Invitrogen). Quantitative RT-PCR is performed in the ABI Prism 7000 Sequence Detection System using cDNAs and human TaqMan Gene Expression Assay primer/probe sets for Krüppel-like factor 4 (KLF4), cyclin-dependent kinase inhibitor 1A (p21) and the ABI TaqMan Universal PCR master mix protocol. Gene expression is normalized with β-actin gene expression in the same sample, and fold changes in KLF4 or p21 are expressed relative to the corresponding expression level in the DMSO treated samples using the comparative CT method. Treatment of one or more myelodysplastic syndromes (MDS), ALL, CML, ATLL, lymphoma, gastric cancer, or multiple myeloma cell lines with LOR-253 results in increased expression KLF4 and/or p21.

Example 10

Treatment with LOR-253 Results in G1/S Cell Cycle Arrest in Myelodysplastic Syndromes (MDS), ALL, CML, ATLL, Lymphoma, Gastric Cancer, and Multiple Myeloma Cell Lines Myelodysplastic syndromes (MDS), ALL, CML, ATLL, lymphoma, gastric cancer, and multiple myeloma cell lines described in Example 8 are treated with DMSO (vehicle control) or 0.1, 0.2, 0.5 or 1 µM LOR-253 for 16 hours. Cells are washed once in PBS+1% FCS and fixed using ice cold 70% ethanol overnight. Fixed cells are washed twice, resuspended in PI/RNaseA solution, containing 20 µg/mL propidium iodide and 250 µg/mL RNaseA, and stained for 30 minuets at 37° C. Stained cells are analyzed using a BD FACSCalibur flow cytometer. The results indicate treatment with LOR-253 results in G1/S cell cycle arrest in one or more myelodysplastic syndromes (MDS), ALL, CML, ATLL, lymphoma, gastric cancer, or multiple myeloma cell lines.

Example 11

Treatment with LOR-253 Induces Apoptosis in Myelodysplastic Syndromes (MDS), ALL, CML, ATLL, Lymphoma, Gastric Cancer, and Multiple Myeloma Cell Lines

Myelodysplastic syndromes (MDS), ALL, CML, ATLL, lymphoma, gastric cancer, and multiple myeloma cell lines described in Example 8 are treated with DMSO, 0.1, 0.2, 0.5 or 1 µM of LOR-253 for 16 hours. Cells are washed twice with cold PBS and resuspended Annexin V binding buffer. $1 \times 10^5$ cells in 100 µL are stained with FITC-Annexin V and propidium iodide, and incubated for 15 minutes at room temperature. After staining, 400 ul of binding buffer is added and the cells are kept on ice until analyzed on a BD FACSCanto flow cytometer. One or more cell lines treated with LOR-253 show elevated Annexin V staining, indicating induction of apoptosis. Increasing concentration of LOR-253 used to treat the cells results in an increase in the early apoptotic population (Q3: Annexin V+/PI−).

Cell lines are also treated with DMSO (vehicle control) or 0.1, 0.2, 0.5 or 1 µM LOR-253 for 48 hours. Cell lysates are collected using a 1% Triton-X100 lysis. Caspase 3 activity is measured using EnzChek Caspase-3 Assay Kit #1 (Life Technologies) with 5 µg of cell lysates according to manufacturer's protocol. Treatment of one or more cell lines with LOR-253 results in elevated Caspase 3 activity, indicating induction of apoptosis.

Total RNA of treated cell lines are extracted using the TRIzol Plus RNA Purification kit (Ambion, Life Technologies), according to the manufacturer's instructions. First strand cDNA is synthesized from 1-2 µg total RNA using random hexamer primers (Invitrogen) and the SuperScript II Reverse Transcriptase kit (Invitrogen). Quantitative RT-PCR is performed in the ABI Prism 7000 Sequence Detection System using cDNAs and human TaqMan Gene Expression Assay primer/probe sets for BCL2-associated X protein (BAX), B-cell CLL/Lymphoma 2 (BCL2) and the ABI TaqMan Universal PCR master mix protocol. Gene expression is normalized with β-actin gene expression in the same sample, and fold changes in BAX or BCL2 are expressed relative to the corresponding expression level in the DMSO treated samples using the comparative CT method. Elevation of BAX and repression of BCL2 upon treatment of one or more myelodysplastic syndromes (MDS), ALL, CML, ATLL, lymphoma, gastric cancer, or multiple myeloma cell lines with LOR-253 indicates induction of apoptosis.

Example 12

In Vivo Efficacy of LOR-253 HCL in Xenograft Model of Myelodysplastic Syndromes (MDS), ALL, CML, ATLL, Lymphoma, Gastric Cancer, and Multiple Myeloma

Model mice of myelodysplastic syndromes (MDS), ALL, CML, ATLL, lymphoma, gastric cancer, and multiple myeloma are created according to standard procedures. The model mice are treated according to several administration schedules as shown in the table below.

| Group | Dose level | Administration Schedule/cycle | Treatment (1 cycle = 7, 14, 21, or 28 days) |
|---|---|---|---|
| 1 | n = 8 | 1 mg/kg-iv | 2T-12B-2T | 1, 2, 3, or 4 cycles |
| 2 | n = 8 | 1 mg/kg-iv | 3T-12B-3T | 1, 2, 3, or 4 cycles |
| 3 | n = 8 | 1 mg/kg-iv | 2T-5B-2T | 1, 2, 3, or 4 cycles |
| 4 | n = 8 | 1 mg/kg-iv | 3T-5B-3T | 1, 2, 3, or 4 cycles |
| 5 | n = 8 | 5 mg/kg-iv | 2T-12B-2T | 1, 2, 3, or 4 cycles |
| 6 | n = 8 | 5 mg/kg-iv | 3T-12B-3T | 1, 2, 3, or 4 cycles |
| 7 | n = 8 | 5 mg/kg-iv | 2T-5B-2T | 1, 2, 3, or 4 cycles |
| 8 | n = 8 | 5 mg/kg-iv | 3T-5B-3T | 1, 2, 3, or 4 cycles |
| 9 | n = 8 | 10 mg/kg-iv | 2T-12B-2T | 1, 2, 3, or 4 cycles |
| 10 | n = 8 | 10 mg/kg-iv | 3T-12B-3T | 1, 2, 3, or 4 cycles |
| 11 | n = 8 | 10 mg/kg-iv | 2T-5B-2T | 1, 2, 3, or 4 cycles |
| 12 | n = 8 | 10 mg/kg-iv | 3T-5B-3T | 1, 2, 3, or 4 cycles |
| 13 | n = 8 | 20 mg/kg-iv | 2T-12B-2T | 1, 2, 3, or 4 cycles |
| 14 | n = 8 | 20 mg/kg-iv | 3T-12B-3T | 1, 2, 3, or 4 cycles |
| 15 | n = 8 | 20 mg/kg-iv | 2T-5B-2T | 1, 2, 3, or 4 cycles |
| 16 | n = 8 | 20 mg/kg-iv | 3T-5B-3T | 1, 2, 3, or 4 cycles |
| 17 | n = 8 | Vehicle alone | 3T-5B-3T | 1, 2, 3, or 4 cycles |

T = consecutive days treatment
B = break for one

The results show that one or more groups are effectively treated by LOR-253.

Example 13

In Vivo Dose-Dependent Pharmacokinetic (PK) and Pharmacodynamic (PD) Responses in Xenograft Model Mice Treated by LOR-253 HCL with Myelodysplastic Syndromes (MDS), ALL, CML, ATLL, Lymphoma, Gastric Cancer, and Multiple Myeloma

To study the pharmacokinetic (PK) in myelodysplastic syndromes (MDS), ALL, CML, ATLL, lymphoma, gastric cancer, and multiple myeloma tumor cells treated by LOR-253, CD-1 nude mice are treated by i.v. bolus injections of LOR-253 HCl at 1, 5, and 15 mg/kg. The serum level of LOR-253 in each treatment is measured.

To study the pharmacodynamic (PD) responses, mice are treated for 5 consecutive days with 1, 5, and 15 mg/kg LOR-253. Tumors are measured 16 hours after the last dose, and the KLF-4 protein level is measured. This results show that average KLF4 protein levels in one or more treatment increase in a dose-dependent manner, correlating with tumor biodistribution and dose-response antitumor activity.

Example 14

In Vivo Efficacy of LOR-253 HCL in a Kasumi-1 AML Xenograft Model

The anti-tumor activity of LOR-253 HCl was evaluated in another in vivo animal model of human AML. The human AML cell line Kasumi-1 was implanted subcutaneously into athymic nude mice. Some tumor-bearing mice were treated with LOR-253 HCl at 30 mg/kg (15 mg/kg twice per day) for two consecutive days per week for four weeks (the "LOR-253 treatment group"). LOR-253 was administered by intravenous (i.v.) bolus injection as the hydrochloric salt form (LOR-253-HCl) formulated in 20% Polyethylene Glycol 400, 10% Propylene Glycol, and 10% Solutol HS in 60% water. Other tumor-bearing mice were treated with a formulation that did not have LOR-253 (the "vehicle control group").

Figure 15:
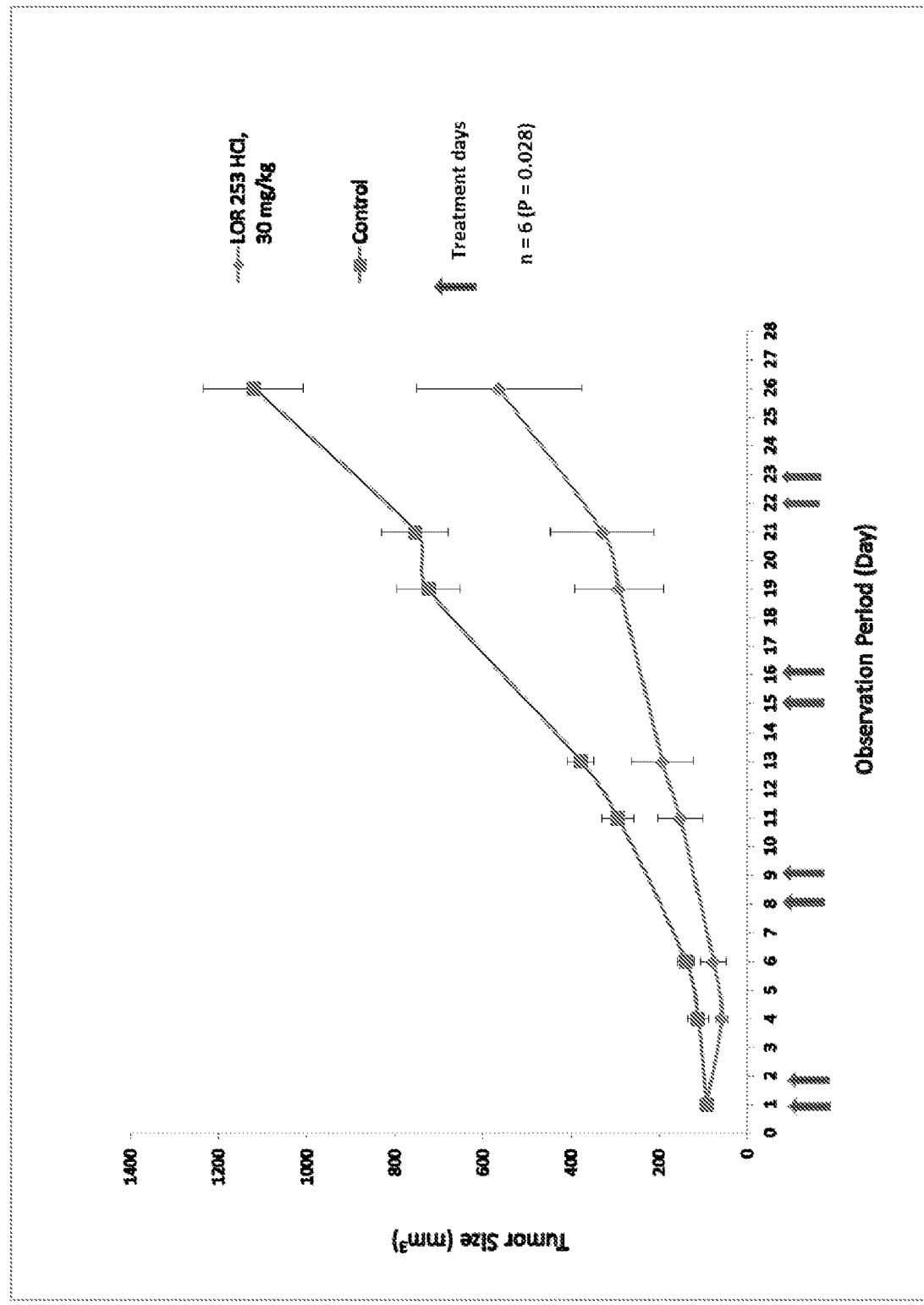
FIG. 15 depicts in vivo efficacy of LOR-253 HCL in Kasumi-1 xenograft model mice. Tumor sizes of Kasumi-1 xenograft mice treated with LOR-253 HCL or negative control measured on the indicated days are shown.
Figure 16:
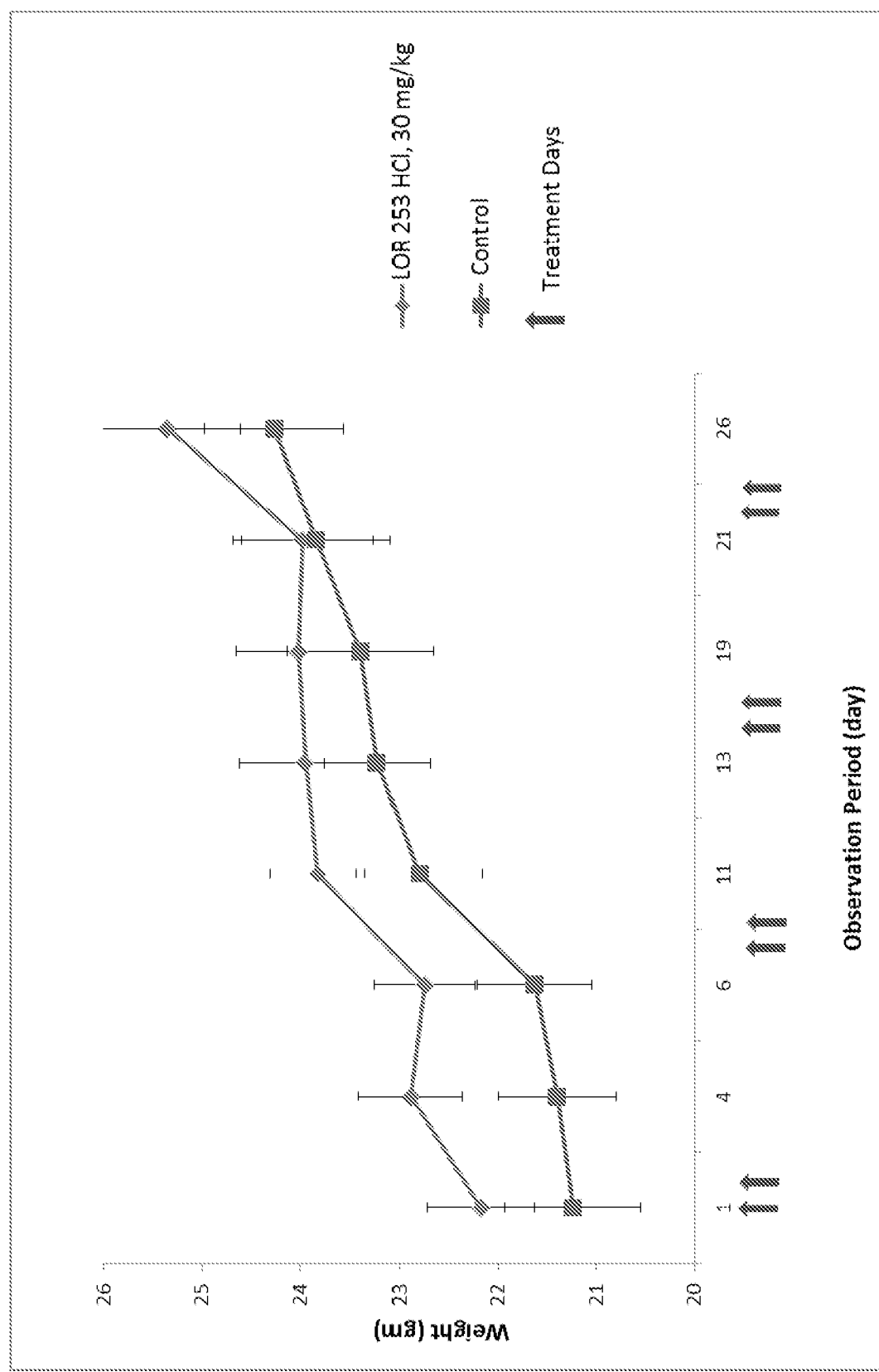
FIG. 16 depicts body weight measurements on the indicated days of Kasumi-1 tumor-bearing Mice treated with LOR-253 HCL or negative control.

The major endpoint was to observe for tumor growth inhibition after treatment with LOR-253 HCl and compare the anti-tumor effects of different dosing schedules. Tumor sizes were measured three times per week from day 10 after the tumor cell inoculation. Tumors were measured in three dimensions using calipers and the volume was expressed in millimeters cubed using the formula: V=0.5 a×b×c, where a, b, and c are the length, width, and height of the tumor, respectively. Mean tumor volumes+/−standard error (SE) were calculated from each measurement and then plotted in a standard graph to compare the anti-tumor efficacy of drug treatment to that of control (FIG. 15). Toxicity was assessed by clinical observations and by measurement of mouse body weight in grams twice per week over the course of the study. Mean body weights were calculated from each measurement and then plotted to compare body weight changes in the drug treatment group to that of control (FIG. 16).

The tumor inhibition results as shown in FIG. 15 demonstrate that the LOR-253 treatment group produced a statistically significantly increased inhibitory effect in this model compared to the vehicle control group (p=0.028 by Student's t-test). In addition, the toxicity results as shown in FIG. 16 demonstrate that the mice in the treatment group did not show body weight loss. The mice in the treatment group also did not show other overt signs of toxicity. These results indicate that this treatment schedule was well tolerated. LOR-253 HCl showed significant tumor growth inhibition as a single agent at twice per week dosing without obvious signs of toxicity, suggesting that LOR-253 HCl has a sufficient therapeutic window and that this agent is a potential chemotherapeutic agent for the treatment of AML.

Example 15

In Vivo Efficacy of LOR-253 HCL in an HL-60 AML Xenograft Model

The anti-tumor activity of LOR-253 HCl, as a single agent and in combination with azacitidine, was evaluated in another in vivo animal model of human AML. The human AML cell line HL-60 was implanted subcutaneously into athymic nude mice. Tumor-bearing mice were treated with LOR-253 HCl alone or in combination with azacitidine, with azacitidine alone, or with a negative control vehicle. The detailed treatment conditions are as follows.

Group 1: Negative control group. LOR-253 HCl control vehicle, 2×/day, 3 cycles of 2 consecutive days, 5 days between cycles, i.v., plus 1% D-mannitol every four days by s.c. injection Group 2: Azacitidine (in 1% D-mannitol) at 10 mg/kg 1× on days 1, 4, 8, 11, 15 and 18 by subcutaneous (s.c.) injection Group 3: LOR-253 HCl at 15 mg/kg bid for 3 cycles, each cycle is 2 consecutive days of dosing per week with 5 days of non-dosing, i.v., n=9 (2T-5B)

Group 4: LOR-253 HCl at 15 mg/kg 2×/day (bid) for 3 cycles, each cycle is 1 day of dosing per week with 6 days of non-dosing, i.v., n=9 (1T-6B)

Group 5: Combination of LOR-253 (2T-5B) and azacitidine. LOR-253 HCl at 15 mg/kg bid for 3 cycles, each cycle is 2 consecutive days of dosing per week with 5 days of non-dosing, i.v., n=9 (2T-5B) plus azacitidine at 10 mg/kg 1× every four days by s.c. injection Group 6: Combination of LOR-253 (1T-6B) and azacitidine. LOR-253 HCl at 15 mg/kg bid for 3 cycles, each cycle is 1 day of dosing per week with 6 days of non-dosing, i.v., n=9 (1T-6B) plus azacitidine at 10 mg/kg 1× every four days by s.c. injection The major endpoint was to observe for tumor growth inhibition after treatment with LOR-253 HCl in combination with azacitidine. Tumor sizes were measured three times per week. Tumors were measured in three dimensions using calipers and the volume was expressed in millimeters cubed using the formula: V=0.5 a×b×c, where a, b, and c are the length, width, and height of the tumor, respectively. Mean tumor volumes+/−standard error (SE) were calculated from each measurement and then plotted in a standard graph to compare the anti-tumor efficacy of drug treatment to that of control (FIG. 17).

Figure 17:
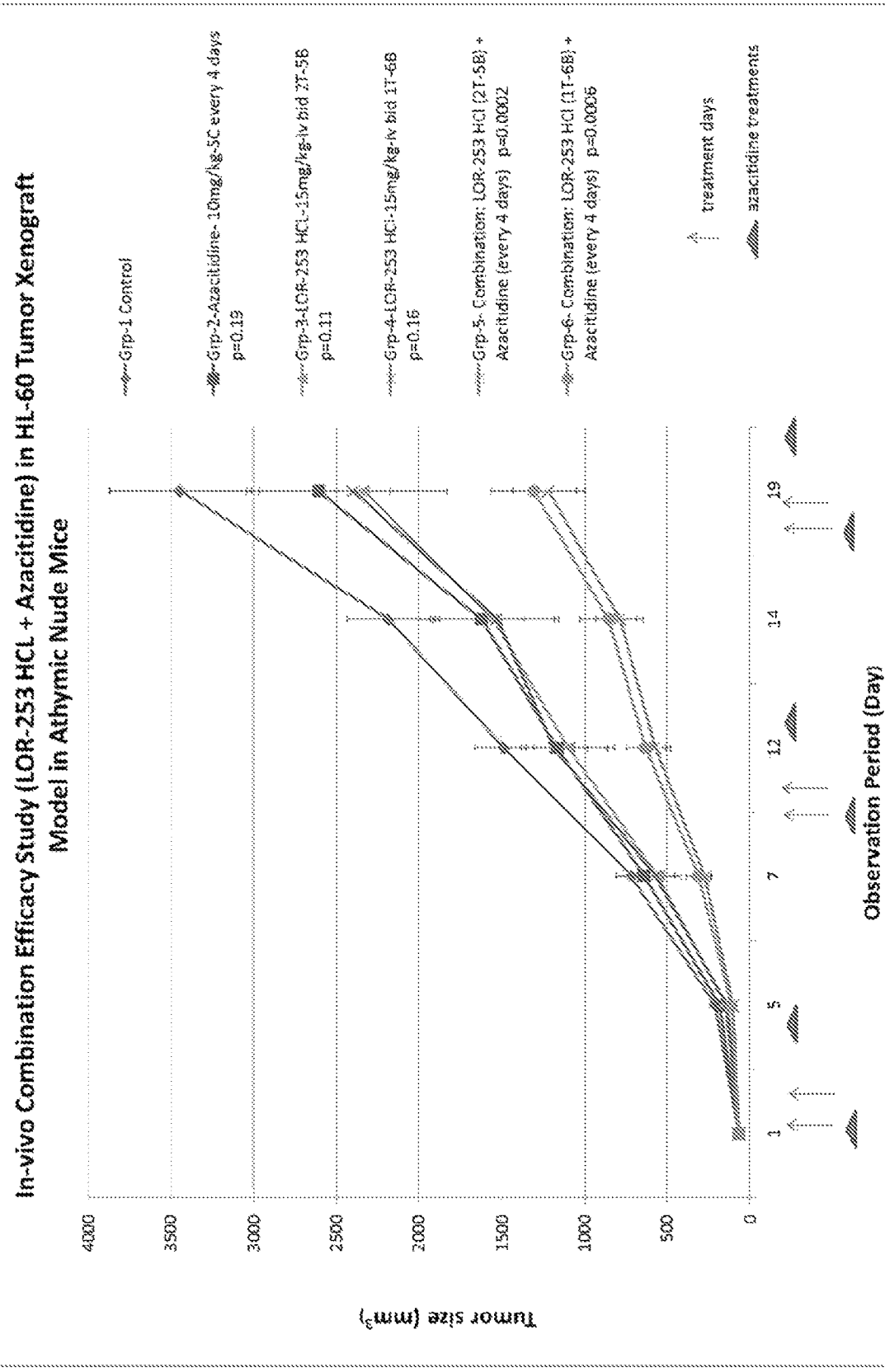
FIG. 17 depicts in vivo efficacy of LOR-253 HCL as a single agent or in combination with azacitidine in HL-60 xenograft model mice. Tumor sizes of HL-60 xenograft mice treated with the indicated conditions measured on the indicated days are shown.
Figure 18:
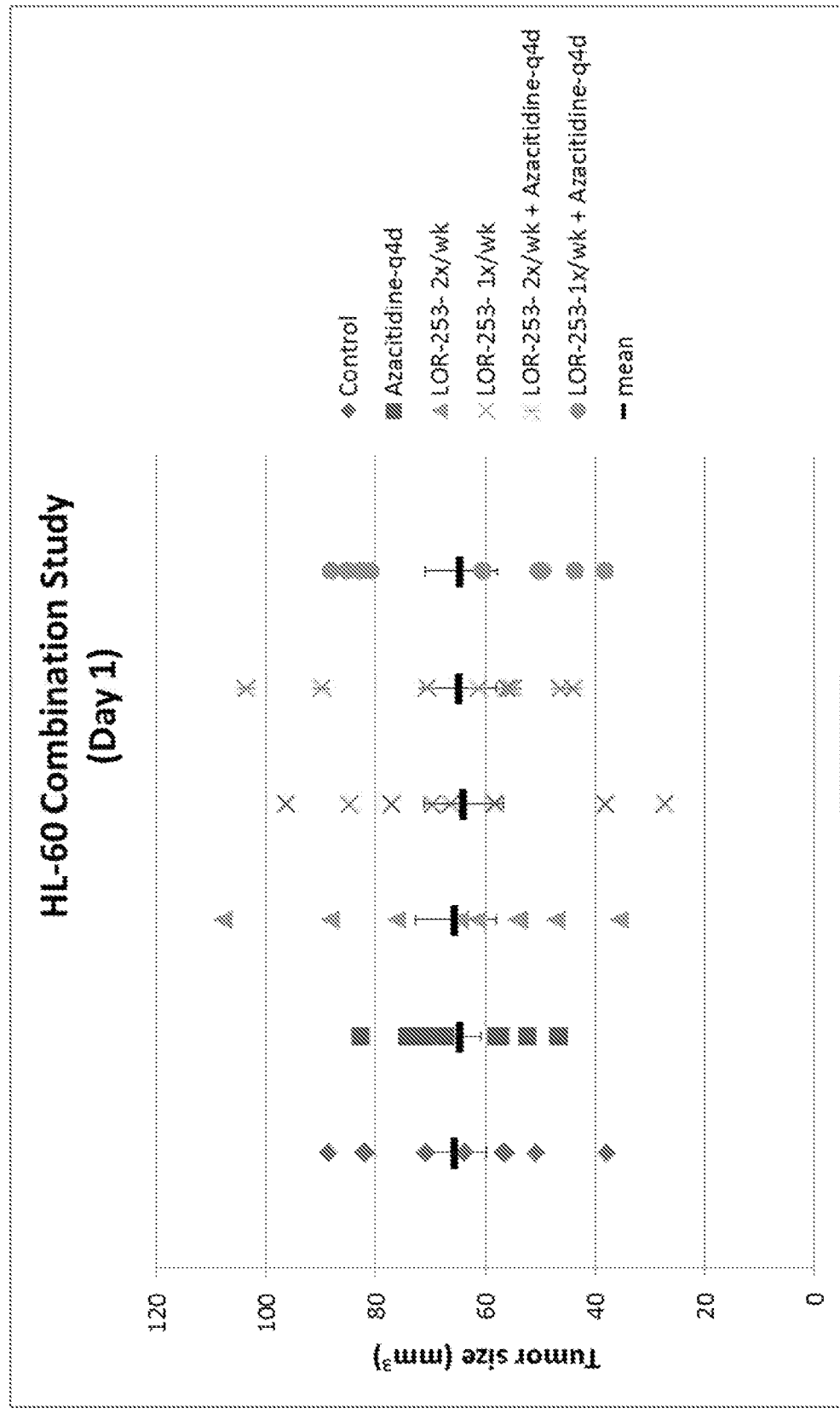
FIG. 18 and FIG. 19 depict the tumor sizes of individual animals at the beginning (Day 1) and end (Day 19) of the study of FIG. 17, respectively.
Figure 19:
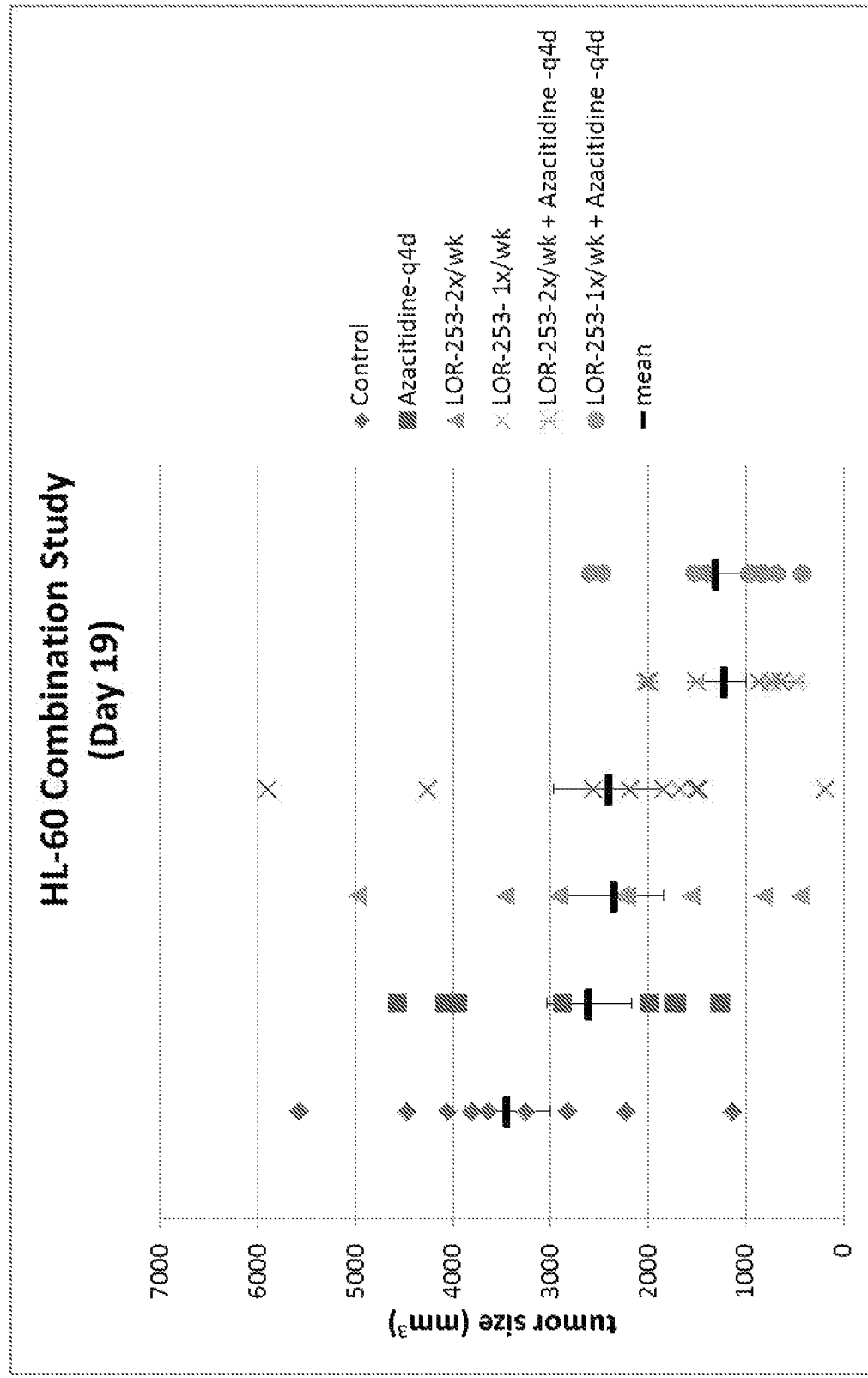

The tumor inhibition results as shown in FIG. 17 demonstrate that LOR-253 HCl administered alone at 15 mg/kg twice per day for either one (Group 4) or two (Group 3) consecutive days per week inhibited growth of HL-60 tumors to approximately the same extent as or slightly more than azacitidine alone. Both once and twice weekly dosing of LOR-253 HCl in combination with azacitidine (Group 6 and Group 5, respectively) resulted in significantly higher levels of tumor growth inhibition compared to either single agent alone (p=0.0002 and p=0.0006 for 1× and 2×LOR-253 HCl treatment, respectively; compared to control, as determined by Student's t-test). FIG. 18 and FIG. 19 show the tumor size data from individual animals at the beginning (Day 1) and end (Day 19) of this study.

Because LOR-253 HCl in combination with azacitidine resulted in even higher levels of tumor growth inhibition than either single agent alone, LOR-253 HCl may also provide additive anticancer efficacy to a standard of care chemotherapeutic for hematological malignancies.

Example 16

In Vivo Efficacy of LOR-253 HCL in a KG-1 AML Xenograft Model

The anti-tumor activity of LOR-253 HCl was evaluated in yet another in vivo animal model of human AML. Xenograft model mice for AML cell line KG-1 was generated with the same method as in Examples 14 and 15, and were treated with LOR-253 HCl or control according to the following regime.

Control-IV-Day 1
LOR-253-15 mg/kg-iv, bid, 2T/wk-Day 1
Control-IV-Day 8
LOR-253-15 mg/kg-iv, bid, 2T/wk-Day 8
Control-IV-Day 13
LOR-253-15 mg/kg-iv, bid, 2T/wk-Day 13
Control-IV-Day 16
LOR-253-15 mg/kg-iv, bid, 2T/wk-Day 16
Control-IV-Day 20
LOR-253-15 mg/kg-iv, bid, 2T/wk-Day 20
Control-IV-Day 26
LOR-253-15 mg/kg-iv, bid, 2T/wk-Day 26

Figure 20:
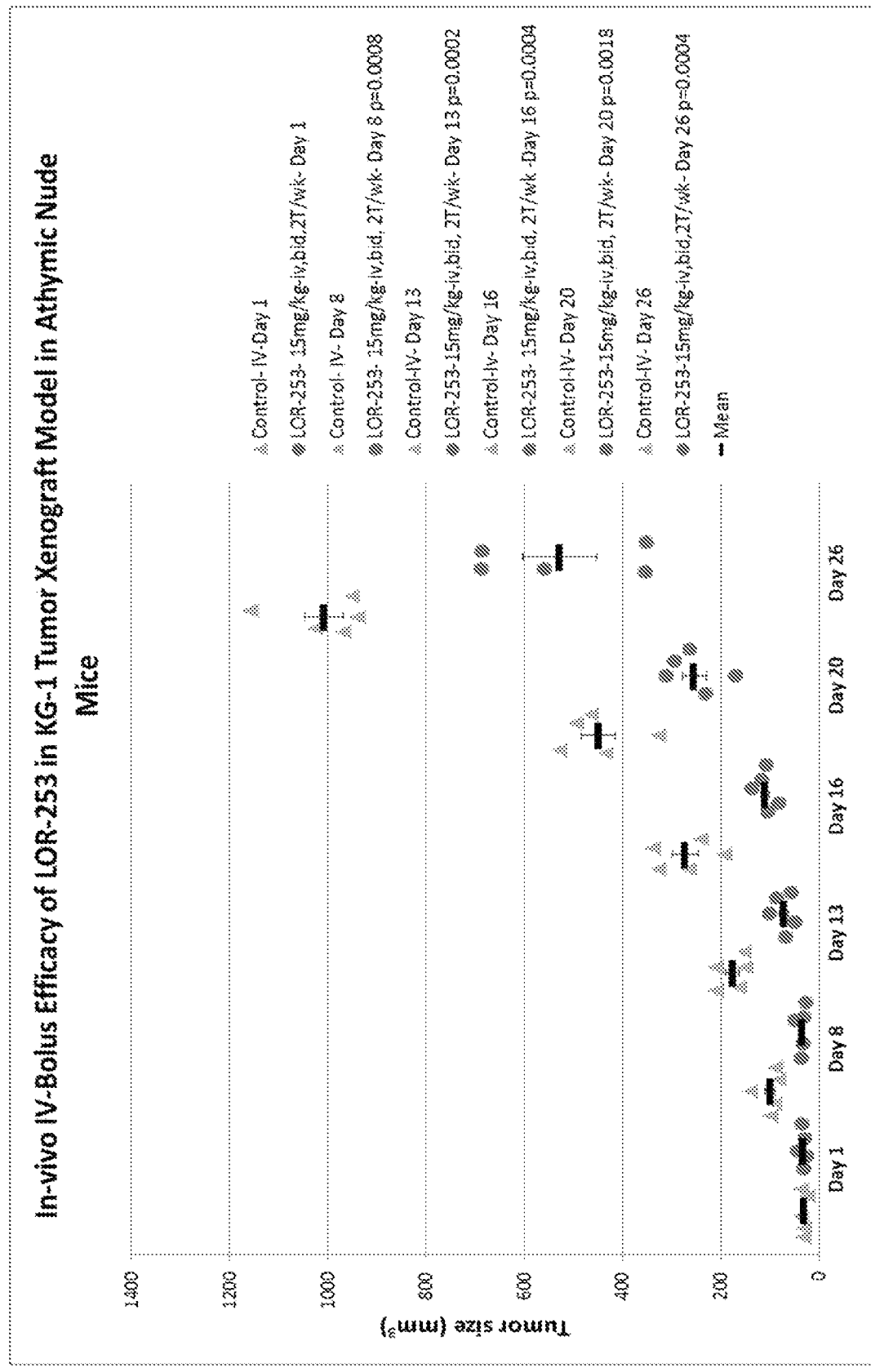
FIG. 20 depicts in vivo efficacy of LOR-253 HCL in KG-1 xenograft model mice. Tumor sizes of KG-1 xenograft mice treated with LOR-253 HCL or negative control measured on the indicated days are shown.

Tumor sizes were measure as described in Examples 14 and 15, and the results are shown in FIG. 20. LOR-253 HCl showed significant tumor growth inhibition as a single agent in this AML animal model as well.

Example 17

In Vivo Efficacy of LOR-253 HCL in a THP-1 AML Xenograft Model

Figure 21:
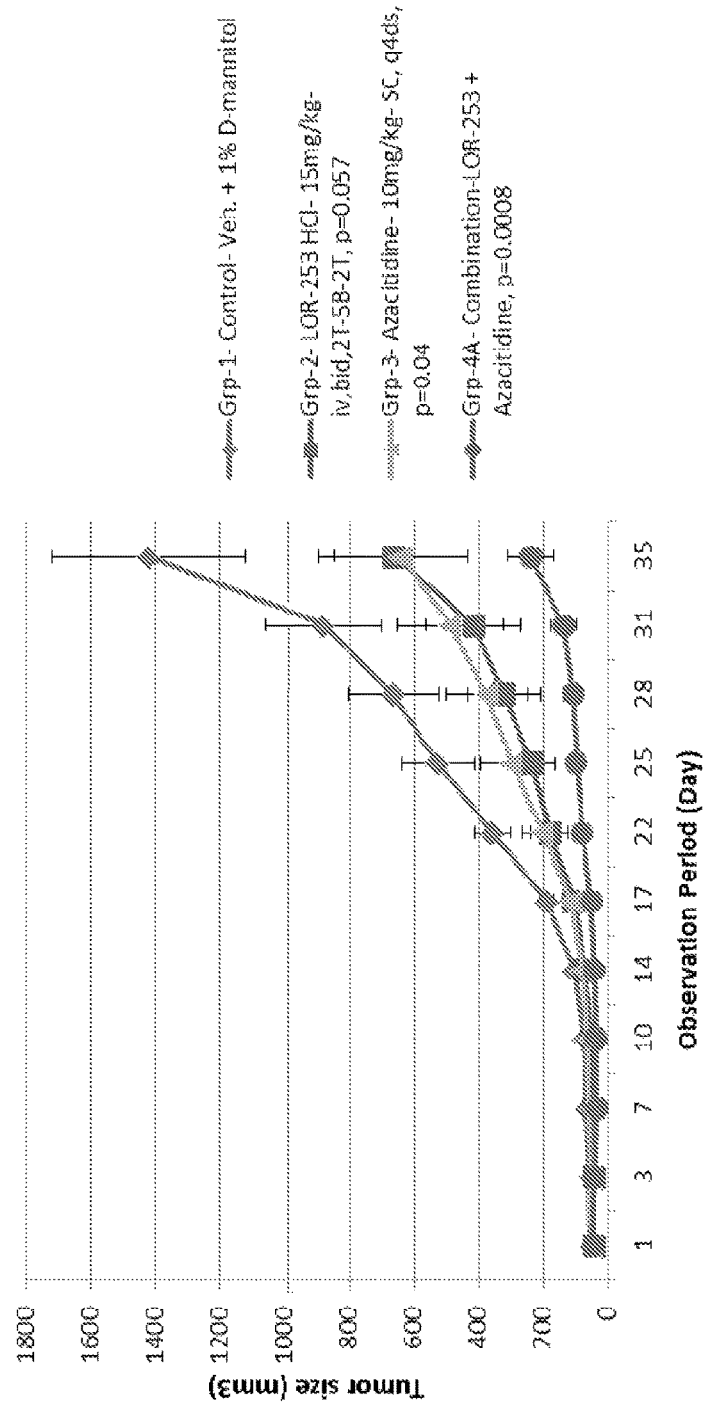
FIG. 21 depicts in vivo efficacy of LOR-253 HCL as a single agent or in combination with azacitidine in THP-1 xenograft model mice. Tumor sizes of THP-1 xenograft mice treated with the indicated conditions measured on the indicated days are shown.

The anti-tumor activity of LOR-253 HCl, as a single agent and in combination with azacitidine, was evaluated in yet another in vivo animal model of human AML. Xenograft model mice for AML cell line THP-1 was generated with the same method as in Examples 14 and 15, and were treated with LOR-253 HCl alone or in combination with azacitidine, with azacitidine alone, or with a negative control vehicle, and tumor sizes were measured as described in Examples 14 and 15. The detailed treatment conditions are shown as follows, and the results are shown in FIG. 21.

Group 1 Control: received i.v. treatments with LOR-253 control vehicle (CV) on Days 1, 2, 8, 9, 15 & 16; received subcutaneous (SC) treatments with Azacitidine control vehicle on Days 1, 4, 8, 11, 15, 18, 22, 25, 29 & 32; and received intraperitoneal (IP) treatments with LOR-253-CV on Days 22, 23, 24, 25, 29& 30.

Group-2-LOR-253: received i.v. treatments on Days 1, 2, 8, 9, 15 & 16; received IP treatments on Days 22, 23, 24, 25, 29 & 30

Group-3-Azacitidine: received SC treatments on Days 1, 4, 8, 11, 15, 18, 22, 25, 29 & 32.

Group-4-Combination: received i.v. treatments with LOR-253 on Days 1, 2, 8, 9, 15 & 16; received IP treatments with LOR-253 on Days 22, 23, 24 & 25; and received SC-treatment with Azacitidine on Days 1, 4, 8, 11, 15, 18, 22 & 25

The tumor inhibition results of this Example demonstrate that LOR-253 HCl administered alone inhibited growth of THP-1 tumors to about the same extent as or slightly more than azacitidine alone. When used in combination with azacitidine, LOR-253 HCl again resulted in significantly higher levels of tumor growth inhibition.

The disclosures, including the claims, figures and/or drawings, of each and every patent, patent application, and publication cited herein are hereby incorporated herein by reference in their entireties.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed:

1. A method of treating cancer in a human subject in need thereof, comprising administering to the subject in need of such treatment an effective amount of a compound of formula II, or a pharmacologically acceptable salt or solvate thereof:

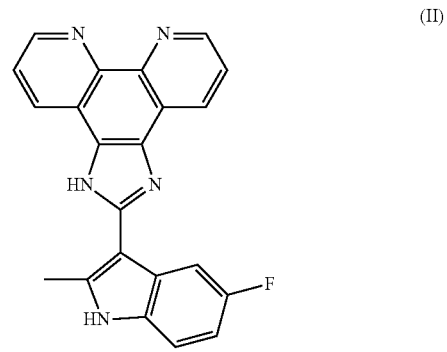 [SMILES: Cc1[nH]c2ccc(F)cc2c1-c1nc2c3cccnc3c3ncccc3c2[nH]1]

wherein the human subject has an abnormal level of Myc activity and the Myc activity in the human subject is decreased after the treatment, and wherein the cancer is acute myeloid leukemia, or myelodysplastic syndrome (MDS).

2. The method of claim 1, wherein the cancer is myelodysplastic syndrome (MDS).

3. The method of claim 1, wherein the cancer is acute myeloid leukemia.

4. A method of treating a myelodysplastic syndrome (MDS) in a human subject, comprising administering to a human subject identified as suffering from a MDS an effective amount of a compound capable of decreasing the Myc activity in the human subject, or a pharmacologically acceptable salt or solvate thereof, wherein the compound has formula II:

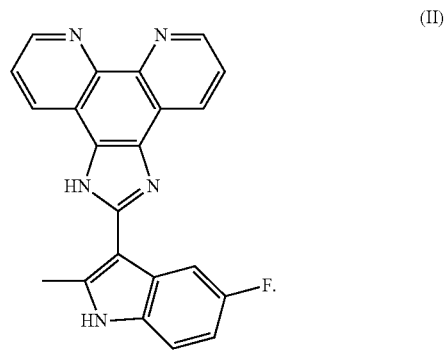 [SMILES: Cc1[nH]c2ccc(F)cc2c1-c1nc2c3cccnc3c3ncccc3c2[nH]1]

5. The method of claim 4, wherein the compound is administered to a human patient identified as having abnormally high level of Myc activity.

6. The method of claim 4, wherein said compound is administered as part of a combination therapy.

7. The method of claim 6, wherein the combination therapy comprises radiotherapy.

8. The method of claim 6, wherein the combination therapy comprises chemotherapy.

9. The method of claim 4, wherein said compound is administered with a dosage of about 125 mg/m$^2$.

10. The method of claim 4, wherein said compound is administered two times per week for four weeks.

* * * * *